United States Patent
Abrams et al.

(10) Patent No.: US 10,842,811 B2
(45) Date of Patent: Nov. 24, 2020

(54) INULIN FOR PREVENTING ANTIBIOTIC RESISTANT INFECTION AND PATHOGEN COLONIZATION

(71) Applicant: The Trustees of Columbia University in the City of New York, New York, NY (US)

(72) Inventors: Julian Abrams, New York, NY (US); Daniel Freedberg, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 16/287,716

(22) Filed: Feb. 27, 2019

(65) Prior Publication Data
US 2020/0030366 A1    Jan. 30, 2020

Related U.S. Application Data

(60) Provisional application No. 62/636,497, filed on Feb. 28, 2018.

(51) Int. Cl.
| | | |
|---|---|---|
| *A61K 31/733* | (2006.01) | |
| *A61P 39/00* | (2006.01) | |
| *A61K 9/00* | (2006.01) | |

(52) U.S. Cl.
CPC ............ *A61K 31/733* (2013.01); *A61P 39/00* (2018.01); *A61K 9/0053* (2013.01)

(58) Field of Classification Search
None
See application file for complete search history.

(56) References Cited

U.S. PATENT DOCUMENTS

| 7,101,565 B2 | 9/2006 | Monte | |
| 7,431,939 B1 * | 10/2008 | Buddington | ......... A61K 31/715 424/439 |
| 9,795,579 B1 | 10/2017 | Han | |
| 9,808,481 B2 | 11/2017 | Ritter et al. | |
| 9,808,497 B2 | 11/2017 | Goel | |
| 9,839,657 B2 | 12/2017 | Deaton et al. | |

OTHER PUBLICATIONS

Guarner, J. Nutr. 137: 2568S-2571S, 2007. (Year: 2007).*
Majid, Clinical Nutrition 33 (2014) 966-972. (Year: 2014).*
Johnson et al., Prebiotics Modulate the Effects of Antibiotics on Gut Microbial Diversity and Functioning in Vitro, Nutrients, vol. 7 / Issue 6, pp. 4480-4497, 2015.
De Souza de Azevedo PO, et al., Stimulating Effects of Sucrose and Inulin on Growth, Lactate, and Bacteriocin Productions by Pediococcus pentosaceus. Probiotics Antimicrobial Proteins, vol. 9 / Issue 4, pp. 466-472, 2017. Abstract.
McDonald et al., Extreme Dysbiosis of the Microbiome in Critical Illness, mSphere, vol. 1 / Issue 4, pp. 1-6, 2016.
Vieira et al., The Role of Probiotics and Prebiotics in Inducing Gut Immunity, Frontiers in Immunology, vol. 4 / Issue 445, pp. 1-12, 2013.
Kolida et al., Prebiotic effects of inulin and oligofructose, British Journal of Nutrition, vol. 87 / Issue S2, pp. 193-197, 2002.
Roller et al., Prebiotic Inulin Enriched with Oligofructose in Combination with the Probiotics Lactobacillus rhamnosus and Bifidobacterium lactis Modulates Intestinal Immune Functions in Rats, The Journal of Nutrition, vol. 134 / Issue 1, pp. 153-156, 2004.
Defoirdt et al., Alternatives to antibiotics to control bacterial infections: luminescent vibriosis in aquaculture as an example., Trends Biotechnology, vol. 25 / Issue 10, pp. 472-479, 2007.
Preiser et al., Metabolic and nutritional support of critically ill patients: consensus and controversies, Critical Care, vol. 19 / Issue 1, pp. 35, 2015.
Knight et al., Effect of synbiotic therapy on the incidence of ventilator associated pneumonia in critically ill patients: a randomised, double-blind, placebo-controlled trial, Intensive Care Med. vol. 35 / Issue 5, pp. 854-861, 2008.

* cited by examiner

*Primary Examiner* — Layla D Berry
(74) *Attorney, Agent, or Firm* — Leason Ellis LLP

(57) ABSTRACT

The present disclosure provides for methods and compositions for the treatment and prevention of antibiotic-resistant infections or pathogen colonization in critically ill patients in the intensive care unit (ICU) or in other populations at high risk for such infections.

20 Claims, 10 Drawing Sheets
(6 of 10 Drawing Sheet(s) Filed in Color)

| | No Antibiotics | | Antibiotics |
|---|---|---|---|
| Aminoglycoside | +56 | +21 | +118 |
| Beta-lactamase | - | +74 | +552 |
| Macrolide | - | - | +110 |
| Tetracycline | +200 | +92 | +422 |
| Vancomycin | - | - | +136 |

INULIN FOR PREVENTING ANTIBIOTIC RESISTANT INFECTION AND PATHOGEN COLONIZATION

CROSS REFERENCE TO RELATED APPLICATIONS

This application claims the benefit of U.S. Provisional Application No. 62/636,497 filed on Feb. 28, 2018, the entire content of which is herein incorporated by reference.

FIELD OF THE INVENTION

The present invention relates to methods and compositions for the treatment and prevention of bacterial infections. In particular, the present disclosure relates to methods of using dietary fibers such as an inulin for the treatment and/or prevention of antibiotic-resistant infections and/or pathogen colonization, e.g., in the intensive care unit (ICU) or in other populations at high risk for such infections.

BACKGROUND OF THE INVENTION

Infection is the single most common cause of death in the intensive care unit (ICU). Patients in the ICU are 3 times more likely to acquire antibiotic-resistant infections compared to non-ICU patients and 5-10 times more likely to die of them. Antibiotic resistance in the ICU is fundamentally a problem of the human gastrointestinal microbiome, the critical reservoir for the bacteria and plasmids that encode antibiotic resistance genes. The normal gut microbiota prevents colonization and subsequent infection with multi-drug resistant (MDR) organisms through competition for resources and other mechanisms. In critical illness, normal colonization resistance is lost; there are no currently available therapies to prevent loss of gut colonization resistance and subsequent proliferation of MDR organisms.

Specific gut bacteria that produce beneficial short-chain fatty acids (SCFAs) are key to colonization resistance. SCFAs moderate colonic inflammation, enlarge the pool of regulatory T cells, and contribute to defense from pathogens. During critical illness, SCFA-producing bacteria and SCFAs are depleted, and proliferation of vancomycin-resistant *Enterococcus* and other pathogens occurs in the setting of diminished colonization resistance and loss of SCFA-producing bacteria.

A wide variety of prebiotics and probiotics are being energetically tested in the ICU and in other settings where patients are at high risk for infection. Most of these substances are derived from *Lactobacillus* or *Bifidobacteria*, organisms that are generally thought to be beneficial, although there is little data to suggest that they would be particularly useful or effective in the ICU. Several companies have been testing synbiotics which are a combination of a fiber-derived prebiotic and viable bacteria. One of the most widely tested is 2000 FORTE (MediPharm, Sweden) which was studied in several European trials (see e.g., Knight D J et al., Intensive Care Med 2009).

The prebiotic fiber inulin is a non-digestible polysaccharide and is a key nutrient source for beneficial SCFA-producing bacteria that live in the human gut. In animals and humans, inulin increases gut SCFA content, induces bacteriocin production, and improves gut barrier function. It has been observed that loss of SCFA-producing bacteria in the ICU associates with a loss of gastrointestinal colonization resistance and in subsequent colonization with pathogens. Inulin has been studied extensively in humans, including critically ill patients, and appears safe and well tolerated. Inulin can be readily made from chicory and other sources. Dehydrated (powder) inulin is easily manufactured and is widely available as an unregulated dietary supplement, taken by individuals to improve digestive health. An intravenous form of inulin (in solution) was formerly used to measure creatinine clearance but is no longer widely used for that purpose.

There remains an unmet and urgent need for new therapies for treating or preventing antibiotic-resistant bacterial infections or gastrointestinal pathogen colonization, including in those patients who are critically ill and/or in a specialized care facility such as an ICU.

SUMMARY

The present disclosure provides for a method of treating or preventing a bacterial infection, or decreasing antibiotic resistance of gastrointestinal microbiome, in a critically ill patient or an immunosuppressed (or immunocompromised) patient, comprising administering at least one dietary fiber (e.g., an inulin) to the patient.

Also encompassed by the present disclosure is a method of treating or preventing pathogen colonization, or increasing an abundance of short-chain fatty acids (SCFA)-producing bacteria, in a critically ill patient or an immunosuppressed (or immunocompromised) patient, comprising administering at least one dietary fiber (e.g., an inulin) to the patient.

The present disclosure provides for a method of treating or preventing pathogen colonization in a critically ill patient or an immunosuppressed (or immunocompromised) patient, comprising administering one or more dietary fibers to the patient at an amount of at least 10 g/day.

The one or more dietary fibers may comprise inulin, resistant maltodextrin, resistant starch, polydextrose, soluble corn (gluco) fiber, fructo-oligosaccharides, fiber dextrin, pullulan, hemicellulose, galacto-oligosaccharides, arabinoxylan-oligosaccharides, lactulose, tagatose, prebiotic agents, or combinations thereof. The one or more dietary fibers may be any dietary fiber or combinations described herein.

The critically ill patient may be in an intensive care unit (ICU). The immunosuppressed patient may be a transplant recipient.

The bacterial infection may be an antibiotic-resistant infection, such as a vancomycin-resistant infection.

In certain embodiments, at least 10 g/day (such as about 16 g/day, or about 32 g/day) of the one or more dietary fibers (e.g., the inulin) is administered to the subject.

The one or more dietary fibers (e.g., the inulin) may be administered to the subject in 1 dose/day, 2 doses/day, 3 doses/day, 4 doses/day, etc. The one or more dietary fibers (e.g., the inulin) may be administered to the subject every other day, every other two days, every other three days, etc.

The one or more dietary fibers (e.g., the inulin) may be administered to the subject for about 3 days to about 2 weeks, e.g., for about 7 days.

The one or more dietary fibers (e.g., the inulin) may be administered orally.

The pathogen colonization may comprise gastrointestinal pathogen colonization, such as multidrug-resistant (MDR) bacterial colonization. The pathogen colonization may comprise colonization by antibiotic-resistant pathogens. The pathogen colonization may comprise colonization by vancomycin-resistant Enterobacteriaceae (VRE), beta-lactamase (ESBL) producing Gram-negative bacteria, *Klebsiella*

*pneumonia* carbapenemase (KPC)-producing bacteria, methicillin-resistant *Staphylococcus aureus* (MRSA), or combinations thereof. The pathogen colonization may comprise colonization by Enterobacteriaceae, *Staphylococcus*, *Pseudomonas*, or combinations thereof.

The SCFA-producing bacteria may comprise Clostridial Clusters IV/XIVa. The SCFA-producing bacteria may comprise *Faecalibacterium prausnitzii*, *Eubacterium* rectale, Ruminococcus, Blautia, *Coprococcus, Roseburia*, or combinations thereof.

The SCFA may comprise butyrate, propionate, acetate, or combinations thereof.

The present method may further comprise administering one or more antibiotics to the subject.

The present method may further comprise administering one or more probiotics to the subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1A:
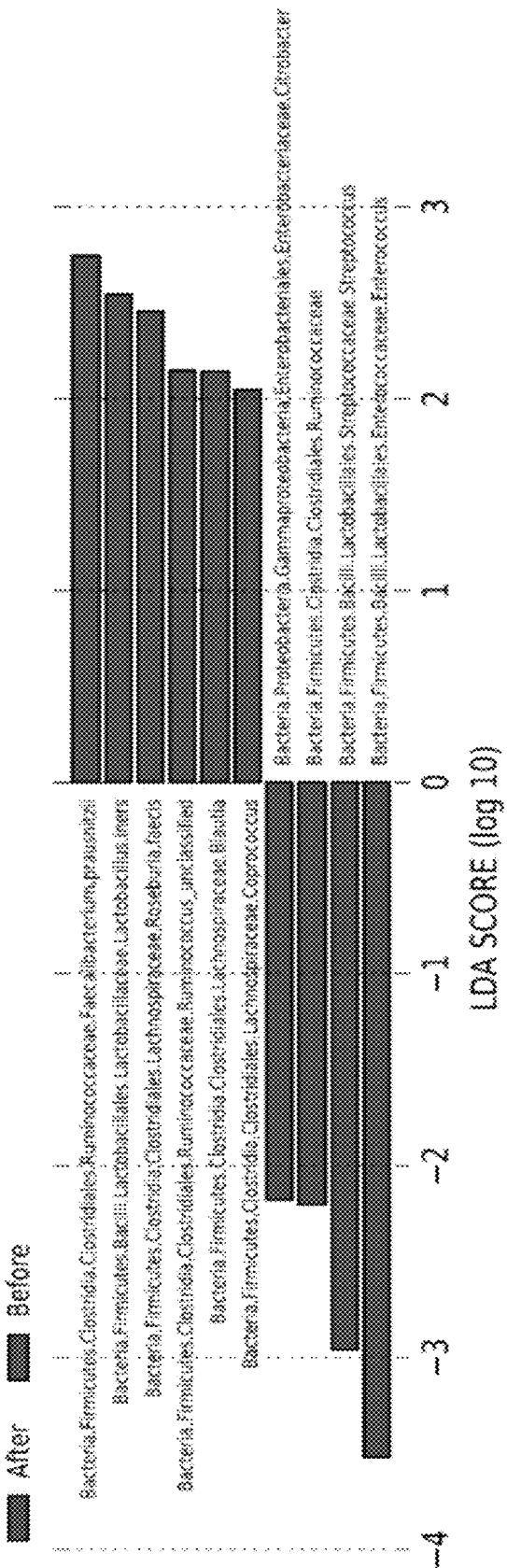
FIGS. 1A-1C. Changes within specific bacterial taxa, comparing ICU admission and 72 hours later. Using a linear discriminant analysis (LDA)-based algorithm, significant declines were identified in the short chain fatty acid-producing Clostridial Clusters IV (*Faecalibacterium prausnitzii*) and XIVa (Blautia, *Coprococcus, Roseburia*, and Ruminococcus) with an expansion in *Enterococcus*. Changes within specific bacterial taxa are shown as (a) LDA scores, (b) a cladogram, and (c) relative abundance. For (c) only taxa with a pooled minimum of 0.05% median relative abundance are depicted.

The present disclosure provides for methods of using dietary fibers (e.g., an inulin) to restore colonization resistance and prevent or decrease colonization/infection. Inulin supplementation in a patient (e.g., a critically ill patient) may result in higher levels of SCFA-producing bacteria (e.g., Clostridia), which in turn decreases gastrointestinal pathogen colonization and lowers risks for multidrug resistant (MDR) bacterial infections. Dietary fibers (e.g., an inulin) may be used in a critically ill patient (e.g., in an ICU). Dietary fibers may also be used in other populations who are at high risks for colonization/infection, such as a transplant recipient (e.g., a bone marrow transplant recipient, a solid organ transplant recipient, a tissue transplant recipient, etc.), or other patients who are immunosuppressed or immunocompromised.

The present method may reduce the spread of antimicrobial resistance and prevent infections with MDR organisms to improve outcomes in critically ill patients.

The present disclosure provides methods for treatment and/or prevention of antibiotic-resistant infections and pathogen colonization in a subject (who may be a critically ill patient, and/or an immunosuppressed or immunocompromised patient).

The present composition may be administered to a critically ill patient, a patient recovering from critical illness, an acutely ill patient, an immunosuppressed patient, an immunocompromised patient, a postoperative patient, a patient needing surgery, a patient suffering from sepsis or septic shock, a patient in an acute care facility or a patient in a chronic care facility.

The present methods and compositions may improve gastrointestinal health. The present methods and compositions may provide important therapeutic benefits, such as an increased likelihood of survival, shorter duration of ICU stay, lower total cost for ICU stay or full hospitalization, and/or shorter duration of (and/or lower total cost of) follow-up care, or some combination of these benefits or others. The present methods and compositions may prevent spread of antibiotic resistance in critically ill patients.

The present composition comprises (consists essentially of, or consists of) a prebiotic. In one embodiment, the present composition comprises (consists essentially of, or consists of) a single type of prebiotic (such as a single type of a dietary fiber, e.g., an inulin), rather than a mixture of prebiotics (e.g., dietary fibers). In another embodiment, the present composition is substantially free of, or does not contain, a probiotic (e.g., bacteria).

The present methods and compositions may promote the growth of beneficial SCFA-producing bacteria, and/or decrease pathogen colonization or infection (or decrease risk for pathogen colonization or infection).

The present methods and compositions may increase the levels of gastrointestinal (gut) short chain fatty acids (SCFAs) in a subject, induce bacteriocin production, and/or improve gut barrier function.

The present methods and compositions may increase gastrointestinal microbial diversity, and/or prevent multidrug-resistant (MDR) bacterial colonization in a subject.

The present disclosure provides for a method of treating or preventing a bacterial infection, or decreasing antibiotic resistance of gastrointestinal microbiome, in a subject (e.g., a critically ill patient or an immunosuppressed/immunocompromised patient), comprising administering a dietary fiber (e.g., an inulin) to the subject/patient.

The critically ill patient may be in an intensive care unit (ICU). The immunosuppressed/immunocompromised patient may be a transplant recipient (e.g., an organ or tissue transplant recipient, such as a bone marrow transplant recipient, a solid organ transplant recipient, etc.).

The bacterial infection may be an antibiotic-resistant infection, such as a vancomycin-resistant infection.

The present disclosure provides for a method of treating or preventing pathogen colonization, or increasing an abundance of short-chain fatty acids (SCFA)-producing bacteria in a subject (e.g., a critically ill patient or an immunosuppressed/immunocompromised patient), comprising administering a dietary fiber (e.g., an inulin) to the subject/patient.

The pathogen colonization may comprise gastrointestinal pathogen colonization. The pathogen colonization may be multidrug-resistant (MDR) bacterial colonization. The pathogen colonization may comprise colonization by antibiotic-resistant pathogens. The pathogen colonization may comprise colonization by vancomycin-resistant Enterobacteriaceae (VRE), beta-lactamase (ESBL) producing Gram-negative bacteria, *Klebsiella pneumonia* carbapenemase (KPC)-producing bacteria, methicillin-resistant *Staphylococcus aureus* (MRSA), or combinations thereof. The pathogen colonization may comprise colonization by Enterobacteriaceae, *Staphylococcus, Pseudomonas*, or combinations thereof.

The SCFA-producing bacteria may comprise Clostridial Clusters IV/XIVa. The SCFA-producing bacteria may comprise *Faecalibacterium prausnitzii, Eubacterium* rectale, Ruminococcus, Blautia, *Coprococcus, Roseburia*, or combinations thereof.

As used herein, the term "short chain fatty acid" or "SOFA" refers to a subgroup of fatty acids with aliphatic tails of no greater than six carbons. They include, but are not limited to, butyrate, propionate, acetate, acetic acid, propionic acid, isobutyric acid, butyric acid, isovaleric acid, valeric acid, caproic acid, lactic acid, succinic acid, or combinations thereof.

The present disclosure provides for a method of treating or preventing pathogen colonization in a critically ill patient or an immunosuppressed patient, comprising administering one or more dietary fibers to the patient at an amount of at least 10 g/day.

The present composition (e.g., a dietary fiber such as an inulin) may be administered orally.

The present method may further comprise administering one or more antibiotics to the subject.

The present method may further comprise administering one or more probiotics to the subject.

The present disclosure provides for compositions and methods for the treatment or prophylaxis of bacterial infections.

The present pharmaceutical composition may comprise, or consist essentially of (or consist of), one or more dietary fibers.

The present pharmaceutical composition may comprise, or consist essentially of (or consist of), one or more antibiotics and one or more dietary fibers.

The present disclosure provides methods of using a combination of an antibiotic and a dietary fiber. In one embodiment, a subject having a bacterial infection is administered an antibiotic and a dietary fiber.

Methods and compositions of the present invention can be used for prophylaxis as well as treating bacterial infections (e.g., amelioration of signs and/or symptoms of bacterial infections).

For prophylaxis, the present composition can be administered to a subject in order to prevent the onset of one or more symptoms of a bacterial infection. In one embodiment, the subject can be asymptomatic. The subject may have been, or have not been, exposed to the bacterium. A prophylactically effective amount of the agent or composition is administered to such a subject. A prophylactically effective amount is an amount which prevents the onset of one or more symptoms of the bacterial infection.

The present composition can be administered to a subject to treat a bacterial infection. In one embodiment, the subject is symptomatic. In another embodiment, the subject can be asymptomatic. A therapeutically effective amount of the composition is administered to such a subject. A therapeutically effective amount is an amount effective to ameliorate one or more symptoms of the disorder.

The bacterial infections may be a nosocomial infection, and/or an opportunistic infection.

The bacterial infections may be a respiratory tract infection, a pulmonary tract infection, respiratory pneumonia, a urinary tract infection, a blood infection, an ear infection, an eye infection, a central nervous system infection, a surgical site wound infection, bacteremia, a gastrointestinal tract infection, a bone infection, a joint infection, a skin infection, a burn infection, a wound infection, dental plaque, gingivitis, chronic sinusitis, endocarditis, or combinations thereof. The infection may be of the pulmonary tract and may be pneumonia.

The subject may have cystic fibrosis, and/or primary ciliary dyskinesia. The subject may be immunocompromised or immunosuppressed. The subject may be undergoing, or has undergone, surgery, implantation of a medical device, and/or a dental procedure. For example, the medical device can be a catheter, a joint prosthesis, a prosthetic cardiac valve, a ventilator, a stent, an intrauterine device, or combinations thereof. The treatment may be therapeutic or prophylactic. In certain embodiments, the present compositions and methods are used prophylactically when the subject is undergoing surgery, a dental procedure or implantation of a medical device.

The present compositions may be used in vitro or administered to a subject. The administration may be oral, topical, intravenous, intranasal, or any other suitable route as described herein.

Dietary fibers may include the edible parts of plants or analogous carbohydrates that are resistant to digestion and absorption in the human small intestine, with complete or partial fermentation in the large intestine. Dietary fibers may be edible carbohydrates, which are neither digested nor absorbed in the human small intestine. Dietary fibers may be obtained from food material by physical, enzymatic or chemical means and which have a beneficial physiological effect. In general, dietary fibers pass through much of the digestive system intact and may be totally or partially fermented by the intestinal microbiota.

Dietary fibers may include soluble fibers and insoluble fibers. Dietary fibers may include polysaccharides, oligosaccharides, lignin, and associated plant substances. Dietary fibers may include, but are not limited to, inulin, sinistrin, resistant maltodextrin, resistant dextrin, resistant starch, polydextrose, soluble corn (gluco) fiber, fructo-oligosaccharides, fiber dextrin, pullulan, cellulose, hemicellulose, galactans (e.g., galacto-oligosaccharides), arabinoxylan-oligosaccharides, lactulose, tagatose, lignins, chitins, pectins, beta-glucans, xylo-oligosaccharides, oligosaccharides, non-starch polysaccharides, prebiotic agents, or combinations thereof.

The benefit to a subject to be treated is either statistically significant or at least perceptible to the patient or to the physician. In certain embodiments, the present composition is administered for at least 7 days, but the time frame for such treatment can be any desired time frame. In certain embodiments, the present treatment is continued until a desirable gastrointestinal microbiome is achieved.

The present compositions and methods may additionally confer benefits to a subject. These additional benefits are generally known to those skilled in the art and may include managing lactose intolerance, prevention of colon cancer, lowering cholesterol, lowering blood pressure, improving immune function and preventing infections, reducing inflammation and/or improving mineral absorption.

The term "critically ill", herein also acutely ill, may include any condition rendering the patient in need for intensive care therapy. Intensive care therapy may include, but is not limited to, one or more of the following: induction of homeostasis (medical intervention to achieve homeostasis), ventilation (e.g., mechanical ventilation), hemodialysis, vasopressor support, fluid support, parenteral nutrition, administration of red blood cell concentrates, fresh frozen plasma, platelet concentrates, whole blood, systemic antibiotic and/or antiviral and/or antifungal and/or antiprotozoic therapy, granulocyte infusion, T cell infusion, stem cell infusion, and anticoagulant therapy including, but not limited to, administration of activated protein C and/or anti-thrombin and/or tissue factor pathway inhibitor (TFPI) and/or heparins, including low molecular weight heparins, and/or thrombin inhibitors, administration of corticosteroids, tight glycemic control.

A critically ill patient may be a patient with one or more of the following: a condition requiring mechanical ventilation, trauma, sepsis, cardiopulmonary disease, neoplasm, pneumonia, and a gastrointestinal disease. A critically ill patient may be a patient who is being treated in an intensive care unit (ICU); a patient who is being administered large volumes of blood products (e.g., packed red cells); a patient who is undergoing dialysis (e.g., continuous veno-venous hemofiltration); a patient who is receiving multiple antibiotics; a patient who has a pulmonary artery catheter or an arterial blood pressure catheter inserted; and combinations of any of the foregoing. In some embodiments, a critically ill patient is a patient receiving vasopressor support, and/or mechanical ventilation. A patient receiving vasopressor support may refer to a patient unable to maintain a sufficient blood pressure who is consequently being treated with a vasopressor (e.g., norepinephrine) to raise the patient's blood pressure.

These criteria for critically ill patients are exemplary only, and one skilled in the art will understand that other indicia of a patient in a critically ill state are possible and are considered to be encompassed by the term "critically ill" as it is used herein.

"Sepsis" as used herein refers to whole-body inflammatory state (called a systemic inflammatory response syndrome or SIRS) and the presence of a known or suspected infection. Severe sepsis occurs when sepsis leads to organ dysfunction, low blood pressure (hypotension), or insufficient blood flow (hypoperfusion) to one or more organs (causing, for example, lactic acidosis, decreased urine production, or altered mental status). Sepsis can lead to septic shock, multiple organ dysfunction syndrome/multiple organ failure, and death. Organ dysfunction results from sepsis-induced hypotension and diffuse intravascular coagulation, among other things.

As used herein, a composition is "substantially free" of a probiotic or microbes when microbes are absent or undetectable as determined by the use of standard genomic and microbiological techniques.

The composition and abundance of the established microbiota (e.g., the (relative) abundance of SCFA-producing bacteria) can be studied by sequencing the 16S ribosomal RNA (or 16S rRNA) gene of a sample. 16S rRNA is a component of the 30S small subunit of prokaryotic ribosomes.

The abundance of short-chain fatty acids (SCFA)-producing bacteria may be a relative abundance. In one embodiment, the relative abundance of SCFA-producing bacteria may be defined as the sum total of the relative abundance of the following taxa within Clostridial Clusters IV/XIVa, with all taxa specified at the lowest possible hierarchical level: *Faecalibacterium prausnitzii, Eubacterium rectale, Ruminococcus, Blautia, Coprococcus*, and *Roseburia*. Sequencing data is available in the short-read archive section of the National Center for Biotechnology Information (accession number SRP149563).

The bacteria can be studied by bacterial culture of, e.g., MDR bacteria.

Antibiotic resistance genes may be assayed qualitatively and/or quantitatively. For example, DNA is extracted from samples (e.g., rectal swabs, stool samples, etc.). DNA is then assessed for the presence of antibiotic resistance genes using, e.g., quantitative PCR (qPCR), including multiplex quantitative PCR (qPCR). The microbial DNA array assay may test for a plurality of antibiotic resistance genes (see, e.g., Table 9) and facilitate testing for highly prevalent bacterial antibiotic resistance genes in a single reaction with both resistance gene identification (present vs absent) and quantitative profiling (expression relative to an internal standard).

Fecal SCFA levels (such as levels of butyrate, acetate, and propionate etc.) may be assayed using, e.g., mass spectrometry.

In one embodiment, changes in mammalian gut bacterial populations are assessed by fluorescent in situ hybridization (FISH) with 16S rRNA probes. These 16S rRNA probes, specific for predominant classes of the gut microflora (*Bacteroides, Bifidobacteria, Clostridia*, and *Lactobacilli/Enterococci*), are tagged with fluorescent markers. For example, the probes can include Bif164 (Langendijk et al., Appl. Environ. Microbiol., 61: 3069-3075 (1995)), Bac303 (Manz, Microbiology, 142: 1097-1106 (1996)), His150 (Franks, Appl. Environment. Microbiol., 64: 3336-3345 (1998)), and Lab158 (Harmsen et al., Microbial Ecology Health Disease, 11: 3-12 (1996)). The nucleic acid stain 4'6-diamidino-2-phenylindole (DAPI) may be used for total bacterial counts. Fermentation samples are diluted and fixed in paraformaldehyde. These cells are then washed and re-suspended. The cell suspension is then added to the hybridization mixture and filtered. Hybridization is carried out at appropriate temperatures for the probes. Subsequently, the hybridization mix is vacuum filtered, and the filter mounted on a microscope slide and examined using fluorescence microscopy, such that the bacterial groups could be enumerated (Ryecroft et al., J. Appl. Microbiol., 91: 878 (2001)). U.S. Pat. No. 8,313,789. Specific changes in microbiome or microbiota discussed herein can be detected using various methods, including without limitation quantitative PCR or high-throughput sequencing methods which detect over- and under-represented genes in the total bacterial population (e.g., 454-sequencing for community analysis; screening of microbial 16S ribosomal RNAs (16S rRNA), etc.), or transcriptomic or proteomic studies that identify lost or gained microbial transcripts or proteins within total bacterial populations. See, e.g., U.S. Patent Publication No. 2010/0074872; Eckburg et al., Science, 2005, 308:1635-8; Costello et al., Science, 2009, 326:1694-7; Orrice et al., Science, 2009, 324:1190-2; Li et al., Nature, 2010, 464: 59-65; Bjursell et al., Journal of Biological Chemistry, 2006, 281:36269-36279; Mahowald et al., PNAS, 2009, 14:5859-5864; Wikoff et al., PNAS, 2009, 10:3698-3703.

The amount or dose of the dietary fiber (e.g., an inulin) may range from about 1 g to about 100 g, from about 1 g to about 50 g, from about 2 g to about 45 g, from about 3 g to about 40 g, from about 4 g to about 35 g, from about 5 g to about 32 g, from about 6 g to about 30 g, from about 5 g to about 28 g, from about 6 g to about 25 g, from about 7 g to about 22 g, from about 1 g to about 30 g, from about 2 g to about 25 g, from about 3 g to about 20 g, from about 4 g to about 19 g, from about 5 g to about 18 g, from about 6 g to about 17 g, from about 7 g to about 16 g, from about 8 g to about 15 g, from about 5 g to about 20 g, from about 5 g to about 10 g, from about 10 g to about 20 g, from about 15 g to about 20 g, at least or about 1 g, at least or about 2 g, at least or about 3 g, at least or about 4 g, at least or about 5 g, at least or about 6 g, at least or about 7 g, at least or about 8 g, at least or about 9 g, at least or about 10 g, at least or about 11 g, at least or about 12 g, at least or about 13 g, at least or about 14 g, at least or about 15 g, at least or about 16 g, at least or about 17 g, at least or about 18 g, at least or about 19 g, at least or about 20 g, at least or about 21 g, at least or about 22 g, at least or about 23 g, at least or about 24 g, at least or about 25 g, at least or about 26 g, at least or about 27 g, at least or about 28 g, at least or about 29 g, at least or about 30 g, at least or about 31 g, at least or about 32 g, at least or about 33 g, at least or about 34 g, at least or about 35 g, at least or about 36 g, at least or about 37 g, at least or about 38 g, at least or about 39 g, at least or about 40 g, at least or about 41 g, at least or about 42 g, at least or about 43 g, at least or about 44 g, at least or about 45 g, at least or about 46 g, at least or about 47 g, at least or about 48 g, at least or about 49 g, at least or about 50 g, at least or about 55 g, at least or about 60 g, at least or about 65 g, at least or about 70 g, at least or about 75 g, at least or about 80 g, at least or about 85 g, at least or about 90 g, at least or about 95 g, at least or about 100 g, or more, e.g., in the composition.

The dose of the dietary fiber (e.g., an inulin) may range from about 1 g/day to about 50 g/day, from about 2 g/day to about 45 g/day, from about 3 g/day to about 40 g/day, from about 4 g/day to about 35 g/day, from about 5 g/day to about 32 g/day, from about 6 g/day to about 30 g/day, from about 5 g/day to about 28 g/day, from about 6 g/day to about 25 g/day, from about 7 g/day to about 22 g/day, from about 1 g/day to about 30 g/day, from about 2 g/day to about 25 g/day, from about 3 g/day to about 20 g/day, from about 4 g/day to about 19 g/day, from about 5 g/day to about 18 g/day, from about 6 g/day to about 17 g/day, from about 7 g/day to about 16 g/day, from about 8 g/day to about 15 g/day, from about 5 g/day to about 20 g/day, from about 5 g/day to about 10 g/day, from about 10 g/day to about 20 g/day, from about 15 g/day to about 20 g/day, at least or about 1 g/day, at least or about 2 g/day, at least or about 3 g/day, at least or about 4 g/day, at least or about 5 g/day, at least or about 6 g/day, at least or about 7 g/day, at least or about 8 g/day, at least or about 9 g/day, at least or about 10 g/day, at least or about 11 g/day, at least or about 12 g/day, at least or about 13 g/day, at least or about 14 g/day, at least or about 15 g/day, at least or about 16 g/day, at least or about 17 g/day, at least or about 18 g/day, at least or about 19 g/day, at least or about 20 g/day, at least or about 21 g/day, at least or about 22 g/day, at least or about 23 g/day, at least or about 24 g/day, at least or about 25 g/day, at least or about 26 g/day, at least or about 27 g/day, at least or about 28 g/day, at least or about 29 g/day, at least or about 30 g/day, at least or about 31 g/day, at least or about 32 g/day, at least or about 33 g/day, at least or about 34 g/day, at least or about 35 g/day, at least or about 36 g/day, at least or about 37 g/day, at least or about 38 g/day, at least or about 39 g/day, at least or about 40 g/day, at least or about 41 g/day, at least or about 42 g/day, at least or about 43 g/day, at least or about 44 g/day, at least or about 45 g/day, at least or about 46 g/day, at least or about 47 g/day, at least or about 48 g/day, at least or about 49 g/day, at least or about 50 g/day, at least or about 55 g/day, at least or about 60 g/day, at least or about 65 g/day, at least or about 70 g/day, at least or about 75 g/day, at least or about 80 g/day, at least or about 85 g/day, at least or about 90 g/day, at least or about 95 g/day, at least or about 100 g/day, or more.

Different treatment regimens may be used. In some embodiments, a daily dosage of the dietary fiber (e.g., an inulin), such as any of the exemplary dosages described above, is administered once, twice, three times, or four times a day, for at least or about 2 days, at least or about 3 days, at least or about 4 days, at least or about 5 days, at least or about 6 days, at least or about 7 days, at least or about 8 days, at least or about 9 days, at least or about 10 days, at least or about 11 days, at least or about 12 days, at least or about 13 days, at least or about 2 weeks, at least or about 3 weeks, at least or about 4 weeks, at least or about 1 month, at least or about 2 months, at least or about 3 months, at least or about 4 months, at least or about 5 months, at least or about 6 months, at least or about 7 months, at least or about 8 months, at least or about 9 months, at least or about 10 months, at least or about 11 months, at least or about 1 year, or longer. Depending on the stage and severity of the condition, a shorter treatment time (e.g., up to five days) may be employed along with a high dosage, or a longer treatment time (e.g., ten or more days, or weeks, or a month, or longer) may be employed along with a low dosage. In some embodiments, a once- or twice-daily dosage is administered every other day.

In certain embodiments, at least or about 10 g/day, at least or about 16 g/day, at least or about 32 g/day, of the dietary fiber (e.g., an inulin) is administered to the subject.

In certain embodiments, the dietary fiber (e.g., an inulin) is administered to the subject in 2 doses/day.

In certain embodiments, the dietary fiber (e.g., an inulin) is administered to the subject for about 3 days to about 2 weeks, or for about 7 days.

The present methods and compositions may result in an abundance of SCFA-producing bacteria ranging from about 1% to about 5%, from about 1% to about 4%, from about 1% to about 3%, from about 1% to about 2%, from about 2% to about 5%, from about 2% to about 4%, from about 2% to about 3%, from about 3% to about 5%, from about 3% to about 5%, from about 4% to about 5%, at least or about 1%, at least or about 1.5%, at least or about 2%, at least or about 2.5%, at least or about 3%, at least or about 3.5%, at least or about 4%, at least or about 4.5%, at least or about 5%, at least or about 5.5%, at least or about 6%, at least or about 6.5%, at least or about 7%, at least or about 7.5%, at least or about 8%, at least or about 8.5%, at least or about 9%, at least or about 9.5%, or at least or about 10%, about 12 hours, about 24 hours, about 36 hours, about 48 hours, about 60 hours, about 72 hours, about 1 day, about 2 days, about 3 days, about 4 days, about 5 days, about 6 days, about 7 days, about 1 week, about 2 weeks, about 3 weeks, or about 4 weeks after the start (or end) of the administration of the dietary fiber (e.g., an inulin).

The abundance of SCFA-producing bacteria may be about 1.1 fold, about 1.2 fold, about 1.3 fold, about 1.4 fold, about 1.5 fold, about 1.6 fold, about 1.7 fold, about 1.8 fold, about 1.9 fold, about 2 fold, about 2.5 fold, about 3 fold, about 3.5 fold, about 4 fold, about 4.5 fold, about 5 fold, about 5.5 fold, about 6 fold, about 6.5 fold, about 7 fold, about 8 fold, about 9 fold, about 10 fold, about 12 fold, about 15 fold, about 20 fold, about 25 fold, about 30 fold, about 50 fold, about 100 fold, at least or about 1.2 fold, at least or about 1.5 fold, at least or about 2 fold, at least or about 2.5 fold, at least or about 3 fold, at least or about 3.5 fold, at least or about 4 fold, at least or about 4.5 fold, at least or about 5 fold, at least or about 5.5 fold, at least or about 6 fold, at least or about 6.5 fold, at least or about 7 fold, at least or about 8 fold, at least or about 9 fold, at least or about 10 fold, at least or about 15 fold, at least or about 20 fold, at least or about 25 fold, at least or about 30 fold, at least or about 35 fold, at least or about 40 fold, at least or about 45 fold, at least or about 50 fold, or at least or about 55 fold, of the abundance of the SCFA-producing bacteria in a control subject(s) with low fiber (e.g., less than 7 g/day, less than 6 g/day, less than 5 g/day, or less than 4 g/day fiber or inulin) or no fiber (or no inulin) intake, about 12 hours, about 24 hours, about 36 hours, about 48 hours, about 60 hours, about 72 hours, about 1 day, about 2 days, about 3 days, about 4 days, about 5 days, about 6 days, about 7 days, about 1 week, about 2 weeks, about 3 weeks, or about 4 weeks after the start (or end) of the administration of the dietary fiber (e.g., an inulin).

The level of fecal SCFAs (as described herein, e.g., butyrate, propionate, acetate, or combinations thereof) may be about 1.1 fold, about 1.2 fold, about 1.3 fold, about 1.4 fold, about 1.5 fold, about 1.6 fold, about 1.7 fold, about 1.8 fold, about 1.9 fold, about 2 fold, about 2.5 fold, about 3 fold, about 3.5 fold, about 4 fold, about 4.5 fold, about 5 fold, about 5.5 fold, about 6 fold, about 6.5 fold, about 7 fold, about 8 fold, about 9 fold, about 10 fold, about 12 fold, about 15 fold, about 20 fold, about 25 fold, about 30 fold, about 50 fold, about 100 fold, at least or about 1.2 fold, at least or about 1.5 fold, at least or about 2 fold, at least or about 2.5 fold, at least or about 3 fold, at least or about 3.5 fold, at least or about 4 fold, at least or about 4.5 fold, at least or about 5 fold, at least or about 5.5 fold, at least or about 6 fold, at least or about 6.5 fold, at least or about 7 fold, at least or about 8 fold, at least or about 9 fold, at least or about 10 fold, at least or about 15 fold, at least or about 20 fold, at least or about 25 fold, at least or about 30 fold, at least or about 35 fold, at least or about 40 fold, at least or about 45 fold, at least or about 50 fold, or at least or about 55 fold, of the level of fecal SCFAs in a control subject(s) with low fiber (e.g., less than 7 g/day, less than 6 g/day, less than 5 g/day, or less than 4 g/day fiber or inulin) or no fiber (or no inulin), about 12 hours, about 24 hours, about 36 hours, about 48 hours, about 60 hours, about 72 hours, about 1 day, about 2 days, about 3 days, about 4 days, about 5 days, about 6 days, about 7 days, about 1 week, about 2 weeks, about 3 weeks, or about 4 weeks after the start (or end) of the administration of the dietary fiber (e.g., an inulin).

Antibiotic resistance gene burden may be assessed by multiplex qPCR, and/or culture of the predominant and clinically-relevant antibiotic-resistant bacterial classes (e.g., vancomycin-resistant Enterobacteriaceae (VRE), extended-spectrum beta-lactamase (ESBL) producing Gram-negative bacteria, *Klebsiella pneumonia* carbapenemase (KPC)-producing bacteria, methicillin-resistant *Staphylococcus aureus* (MRSA), or combinations thereof).

MDR infections may be defined as: (a) infections with an organism cultured from any fluid or human body site that shows non-susceptibility in 3 or more major antibiotic classes based on standard CLSI cut-offs ((CLSI) CaLSI. Performance standards for antimicrobial susceptibility testing. CLSI Supplement M100. 2017 (27th Ed.), and (b) delivery or intent to deliver appropriate antibiotics against that infection, defined as antibiotics either received or ordered within no more than 24 hours after culture result. For this definition, appropriate molecular testing (e.g., PCR for MRSA) will be considered equivalent to a positive culture. In one embodiment, MDR infection is defined as culture-proven infection followed by receipt of appropriate antibiotics. Culture-proven infections may be operationalized as those with positive bacterial culture results from any site or fluid collected between 48 hours and 30 days after ICU admission and showing intermediate susceptibility or non-susceptibility across ≥3 antibiotic classes using the clinical breakpoints from the CLSI breakpoints in effect at the time when the culture was performed. Magiorakos et al. Multidrug-resistant, extensively drug-resistant and pandrug-resistant bacteria: an international expert proposal for interim standard definitions for acquired resistance. *Clinical microbiology and infection: the official publication of the European Society of Clinical Microbiology and Infectious Diseases.* 2012; 18(3):268-281.

Classes of antibiotics may be: amikacin, aminoglycosides, carbapenems, cephalosporins (classified based on generation), glycopeptides, fluoroquinolones, lincosamides, macrolides, monobactams, nitroimidazoles, penicillins, penicillins with beta-lactamase inhibitors, polymixin, sulfa-based, rifamycin, tetracyclines, and combinations thereof.

Bacterial antibiotic resistance may be assessed by the following one or more outcomes that represent risk for development of infections with MDR organisms: (1) The total burden of antibiotic resistance genes within the gut microbiome. Antibiotic resistance genes are often harbored by non-pathogenic bacteria and subsequently transferred to and acquired by gut pathogens via plasmids and other mechanisms. Recent data indicates that the thresholds for such lateral gene transfers are lower than was previously believed. Gumpert et al. Transfer and Persistence of a Multi-Drug Resistance Plasmid in situ of the Infant Gut Microbiota in the Absence of Antibiotic Treatment. *Front Microbiol.* 2017; 8:1852. The presence of these genes is therefore important, regardless of the organism that houses the gene. (2) The presence and amount of specific MDR organisms in the gut microbiome known to cause ICU-acquired infections. These organisms are directly responsible for the most difficult-to-treat ICU infections and for the majority of sepsis-related deaths in the ICU. (3) The within-individual change in bacterial antibiotic resistance, as assessed by change in resistance within antibiotic resistance gene categories (Table 9) from baseline to the assessment point. In one embodiment, within-individual changes summing all of the antibiotic resistance genes (87 total) may be considered as the primary outcome assessment.

The composition may further comprise at least one probiotic.

Probiotics may be microorganisms, or processed compositions of microorganisms, which beneficially affect a host. Salminen et al., Probiotics: how should they be defined, *Trends Food* Sci. Technol. 1999: 10 107-10. U.S. Pat. No. 8,216,563.

The present composition may be administered enterally, such as oral, sublingual and rectal administration.

The present probiotic composition can be a food composition, a beverage composition, a pharmaceutical composition, or a feedstuff composition.

The present composition may be a liquid. The composition may be lyophilized, pulverized or powdered. As a powder it can be provided in a palatable form for reconstitution for drinking or for reconstitution as a food additive. The composition can be provided as a powder in combination with a food or drink. The food or drink may be a dairy-based product or a soy-based product. The disclosure also provides a food or food supplement containing the present composition. The composition may be milk-powder based products; instant drinks; ready-to-drink formulations; nutritional powders; milk-based products, such as yogurt or ice cream; cereal products; beverages such as water, coffee, malt drinks; culinary products and soups.

The dietary fiber may be a fructan. Fructans are soluble dietary fibers. Fructans are polymers of fructose residues, ending or not with a glucose unit at what would otherwise be the reducing end. A fructan may end with one or more saccharide residues other than fructose. The linkage position of the fructose residues determines the type of the fructan. Linkage normally occurs at one of the two primary hydroxyls (OH-1 or OH-6), and there are two basic types of simple fructan: inulin (the fructosyl residues are linked by beta-2,1-linkages) and levan (the fructosyl residues are linked by beta-2,6-linkages). The fructan may be a graminian or mixed fructans which have both beta-2,1 and beta-2,6 linkage bonds between the fructose units, and thus contain branches. Fructan may be derived from plants, algae and microorganisms (e.g., bacteria).

Fructans may be linear or branched. The fructans may be products obtained directly from a plant or microbial source, or alternatively products whose chain length has been modified (increased or reduced) by fractionation, synthesis or hydrolysis, in particular enzymatic. Fructans may have a degree of polymerization from 2 to about 1000, e.g., from 2 to about 60. In particular, the inulin may have a degree of polymerization from 2 to about 1000, e.g., from to about 60.

The dietary fiber may be a fructo-oligosaccharide (FOS) which is the degradation product of inulin. Fructo-oligosaccharides can also be enzymatically synthesized from sucrose.

Inulin

Inulin is a non-digestible polysaccharide or oligosaccharides which is a polymer of fructose residues linked by β(2,1) bonds. It may contain one or more chain-terminal glucosyl moieties. The degree of polymerization (DP) of inulin may range from 2 to 1000. In one embodiment, Inulin has a PubChem SID of 329758326. In one embodiment, the chemical formula of inulin is $C_{6n}H_{10n+2}O_{5n+1}$.

In one embodiment, for production of inulins, the chicory roots are sliced and washed, then soaked in a solvent; the inulin is then isolated, purified, and spray dried. Inulin may also be synthesized from sucrose. Niness, K R (July 1999). "Inulin and oligofructose: what are they?". The Journal of Nutrition. 129 (7 Suppl): 1402S-6S. In another embodiment, production of inulin from chicory root involves extraction by hot water. This method produces an extract rich in inulin. In yet another embodiment, the method for purifying an inulin-rich extract contains several steps, including for instance solid/liquid separation, ion exchange, activated carbon filtration, etc. in which the majority of impurities are removed, and inulin-rich composition is obtained. U.S. Pat. No. 10,111,455.

Inulins may encompass inulins with a terminal glucose which are also referred as alpha-D-glucopyranosyl-[beta-D-fructofuranosyl](n-1)-D-fructofuranosides, as well as inulins without glucose which are also referred as beta-D-fructopyranosyl-[D-fructofuranosyl](n-1)-D-fructofuranosides. Inulins can also encompass branched inulin. Inulins can also encompass the hydrolysis products of inulins such as fructo-oligosaccharides (FOS), also called oligofructoses, and they can also encompass fructo-oligosaccharides ending with a terminal glucose with a DP of 3-5 synthesized from sucrose. Inulin can be a liquid or a powder product.

As used herein, the terms "degree of polymerization" or "DP" relates to the number of monosaccharide residues present in an oligosaccharide or polysaccharide. The DP may be calculated as the ratio of the total MW of the polymer or oligomer and the MW of the repeating units.

In an embodiment, the fructan as described herein, e.g., inulin, has an average DP of at least 3. In an embodiment, the fructan as described herein, preferably inulin, has an average DP of at most 500. In an embodiment, said fructan, preferably inulin, has an average DP of at least 3, for example of at least 5, for example of at least 7, for example of at least 10, for example at least 15, for example at least 20, for example at least 25, for example at least 70. In an embodiment, the fructan as described herein, preferably inulin, has an average DP of at least 3 and of at most 500, at least 3 and at most 100, at least 3 and at most 30. The DP may be at least or about 2, at least or about 3, at least or about 4, at least or about 5, at least or about 6, at least or about 7, at least or about 8, at least or about 9, at least or about 10, at least or about 11, at least or about 12, at least or about 13, at least or about 14, at least or about 15, at least or about 16, at least or about 17, at least or about 18, at least or about 19, at least or about 20, at least or about 21, at least or about 22, at least or about 23, at least or about 24, at least or about 25, at least or about 26, at least or about 27, at least or about 28, at least or about 29, at least or about 30, at least or about 35, at least or about 40, at least or about 45, at least or about 50, at least or about 55, at least or about 60, or more. In a further preferred embodiment, the fructan as described herein, preferably inulin, comprises or consists of fructooligosaccharides (FOS). In a further preferred embodiment, the fructan as described herein has an average DP of at least 3 and at most 20, at least 3 and at most 15, such as of at least 3 and at most 10. In yet another preferred embodiment, the fructan as described herein, preferably inulin, comprises or consists of hydrolyzed or partially hydrolyzed fructan, preferably inulin. Hydrolyzed fructan, such as hydrolyzed inulin, may for instance be obtained enzymatically (e.g. by inulinases) or may alternatively be obtained by acid and/or thermal hydrolysis.

Inulin may be derived from any source, including, but not limited to, plants, algae and microorganisms (e.g., bacteria). In certain embodiments, the fructan, preferably inulin, is derived from or isolated from plants, including, but not limited to, chicory (*Cichorium intybus*), agave (*Agave* spp.), banana/plantain (*Musa* spp.), burdock (*Arctium lappa*), camas (*Camassia* spp.), coneflower (*Echinacea* spp.), costus (*Saussurea Costus, Saussurea lappa*), dandelion (*Taraxacum officinale, Taraxacum ruderalia*), elecampane (*Inula helenium*), garlic (*Allium sativum*), Jerusalem artichoke (*Helianthus tuberosus*), globe artichoke (*Cynara scolymus, Cynara cardunculus* var. *scolymus*), jicama (*Pachyrhizus erosus*), leopard's-bane (*Arnica montana*), Mugwort (*Artemisia vulgaris*), onion (*Allium cepa*), wild yam (*Dioscorea* spp.), yacon (*Smallanthus sonchifolius* spp.), leek (*Allium porum*), asparagus, *Scorzonera hispanica*, salsify (*Tragopogon porrifolius*), wheat (*Tritichum aestivum*), dahlia (*Dahlia* spp.). In a specific embodiment, the Inulin is obtained from chicory (*Clchorium intybus*). U.S. Pat. No. 10,086,078.

The present composition may be a dry composition or a liquid composition (such as an aqueous composition). The compositions may be obtained by homogenizing, e.g., plant material. The compositions may refer to extracts, which are enriched in fructan, preferably inulin, compared to the source material it is derived from. Inulin extraction may for instance involve putting plant material in hot water followed by concentration (e.g. evaporation). U.S. Pat. Nos. 10,015, 978 and 9,943,559.

In an embodiment, the compositions comprising fructan, preferably inulin, at an amount of at least or about 1.5 wt %, at least or about 5.0 wt %, at least or about 8.0 wt %, at least or about 10 wt %, at least or about 20 wt %, at least or about 30 wt %, at least or about 40 wt %, at least or about 50 wt %, at least or about 60 wt %, at least or about 70 wt %, at least or about 80 wt %, at least or about 90 wt %, of fructan, preferably inulin, based on the total dry matter weight of the composition.

Prebiotics

The term "prebiotic" refers to an agent that increases the number and/or activity of one or more desired bacteria. A prebiotic may be an agent that allows specific changes both in the composition and/or activity in the gastrointestinal microbiota that may (or may not) confer benefits upon the host. In some embodiments, a prebiotic can be a comestible food or beverage or ingredient thereof.

Prebiotics may be dietary fibers. Prebiotics include, but are not limited to, oligosaccharides and optionally contains fructose, galactose, mannose, soy and/or inulin; and/or dietary fibers. Dietary fibers include, but are not limited to, inulin, inulin-type fructans, fructo-oligosaccharides, oligofructose, galacto-oligosaccharides, xylo-oligosaccharides, isomalto-saccharides, soya oligosaccharides, pyrodextrins, transgalactosylated oligosaccharides, N-acetylglucosamine, N-acetylgalactosamine, glucose, other five- and six-carbon sugars (such as arabinose, maltose, lactose, sucrose, cellobiose, etc.), amino acids, alcohols, sugar alcohols, resistant starch, lactulose, beta-glucan, raffinose, stachyose, raffinose family oligosaccharides (RFO), and mixtures thereof. See, e.g., Ramirez-Farias et al., Br J Nutr (2008) 4:1-10; Pool-Zobel and Sauer, J Nutr (2007), 137:2580S-2584S.

Prebiotics may include complex carbohydrates, amino acids, peptides, minerals, or other essential nutritional components for the survival of the bacterial composition. Prebiotics include, but are not limited to, amino acids, biotin, fructooligosaccharide, galactooligosaccharides, hemicelluloses (e.g., arabinoxylan, xylan, xyloglucan, and glucomannan), inulin, chitin, lactulose, mannan oligosaccharides, oligofructose-enriched inulin, gums (e.g., guar gum, gum arabic and carregenaan), oligofructose, oligodextrose, tagatose, resistant maltodextrins (e.g., resistant starch), transgalactooligosaccharide, pectins (e.g., xylogalactouronan, citrus pectin, apple pectin, and rhamnogalacturonan-I), dietary fibers (e.g., soy fiber, sugarbeet fiber, pea fiber, corn bran, and oat fiber) and xylooligosaccharides. Non-limiting examples of prebiotics include a monomer or polymer of arabinoxylan, xylose, soluble fiber dextran, soluble corn fiber, polydextrose, lactose, N-acetyl-lactosamine, glucose, and combinations thereof. Non-limiting examples of prebiotics also include a monomer or polymer of galactose, fructose, rhamnose, mannose, uronic acids, 3'-fucosyllactose, 3'-sialyllactose, 6'-sialyllactose, lacto-N-neotetraose, 2'-2'-fucosyllactose, and combinations thereof. Non-limiting examples of prebiotics include a monosaccharide selected from the group consisting of arabinose, fructose, fucose, galactose, glucose, mannose, D-xylose, xylitol, ribose, and combinations thereof. In one embodiment, the prebiotic comprises a disaccharide selected from the group consisting of xylobiose, sucrose, maltose, lactose, lactulose, trehalose, cellobiose, and combinations thereof. In another embodiment, the prebiotic comprises a polysaccharide, wherein the polysaccharide is xylooligosaccharide. In one embodiment, the prebiotic comprises a sugar selected from the group consisting of arabinose, fructose, fucose, lactose, galactose, glucose, mannose, D-xylose, xylitol, ribose, xylobiose, sucrose, maltose, lactose, lactulose, trehalose, cellobiose, xylooligosaccharide, and combinations thereof. In one embodiment, the sugar is xylose.

Conditions

The present compositions and methods may be used for the treatment and/or prophylaxis of a disorder associated with the presence in the gastrointestinal tract of a mammalian host of abnormal (or an abnormal distribution of) microbiota. The method comprises administering an effective amount of the present composition.

Such disorders include, but are not limited to, gastrointestinal disorders including irritable bowel syndrome (IBS, or spastic colon), and intestinal inflammation, functional bowel disease (FBD), including constipation predominant FBD, pain predominant FBD, upper abdominal FBD, non-ulcer dyspepsia (NUD), gastro-oesophageal reflux, inflammatory bowel disease including Crohn's disease, ulcerative colitis, indeterminate colitis, collagenous colitis, microscopic colitis, chronic *Clostridium difficile* infection, pseudomembranous colitis, mucous colitis, antibiotic associated colitis, idiopathic or simple constipation, diverticular disease, AIDS enteropathy, small bowel bacterial overgrowth, coeliac disease, polyposis coli, colonic polyps, chronic idiopathic pseudo obstructive syndrome; chronic gut infections with specific pathogens including bacteria, viruses, fungi and protozoa (e.g., *Clostridum difficile* infection (CDI)); viral gastrointestinal disorders, including viral gastroenteritis, Norwalk viral gastroenteritis, rotavirus gastroenteritis, AIDS related gastroenteritis; liver disorders such as primary biliary cirrhosis, primary sclerosing cholangitis, fatty liver or cryptogenic cirrhosis; rheumatic disorders such as rheumatoid arthritis, non-rheumatoid arthritidies, non rheumatoid factor positive arthritis, ankylosing spondylitis, Lyme disease, and Reiter's syndrome; immune mediated disorders such as glomerulonephritis, haemolytic uraemic syndrome, type 1 or type 2 diabetes mellitus, mixed cryoglobulinaemia, polyarteritis, familial Mediterranean fever, amyloidosis, scleroderma, systemic lupus erythematosus, and Behcets syndrome; autoimmune disorders including systemic lupus, idiopathic thrombocytopenic purpura, Sjogren's syndrome, haemolytic uremic syndrome or scleroderma; neurological syndromes such as chronic fatigue syndrome, migraine, multiple sclerosis, amyotrophic lateral sclerosis, myasthenia gravis, Gillain-Barre syndrome, Parkinson's disease, Alzheimer's disease, Chronic Inflammatory Demyelinating Polyneuropathy, and other degenerative disorders; psychiatric disorders including chronic depression, schizophrenia, psychotic disorders, manic depressive illness; regressive disorders including Asperger's syndrome, Rett syndrome, autism, attention deficit hyperactivity disorder (ADHD), and attention deficit disorder (ADD); anorexia nervosa; and dermatological conditions such as chronic urticaria, acne, dermatitis herpetiformis and vasculitic disorders.

Other metabolic disorders include obesity, insulin resistance, hyperglycemia, hepatic steatosis, and small intestinal bacterial overgrowth (SIBO).

Antibiotics

An antibiotic refers to a substance that is used to treat and/or prevent bacterial infection by killing bacteria, inhibiting the growth of bacteria, or reducing the viability of bacteria. The antibiotic may target one or more of the following pathways in bacteria: DNA replication and cell growth; protein biosynthesis; cell wall biosynthesis; transport and membrane function or biosynthesis; metabolism; redox homeostasis, stress response, cell signaling; transcription; translation; tetrahydrofolic acid synthesis; and DNA modification, repair, and maintenance. Non-limiting examples of antibiotics include, penicillin (e.g. flucloxacillin, amoxicillin, ampicillin, carbenicillin, mezlocillin, penicillin), cephalosporine (e.g. cefazolin, cefuroxim, cefotaxim, cefaclor, cefalexin, cefepime), beta-lactamase inhibitor (e.g. sulbactam, tazobactam), tetracycline (e.g. doxycyclin, minocyclin, tetracyclin, oxytetracyclin), aminoglycoside (e.g. gentamicin, neomycin, streptomycin, kanamycin), makrolid antibiotics (e.g. azithromycin, clarithromycin, erythromycin, roxithromycin, spiramycin, clindamycin), lincosamide (e.g. lincomycin), gyrase inhibitor (e.g. ciprofloxacin, ofloxacin, norfloxacin), sulfonamides (such a Bactrim), trimethoprim, glycopeptides (e.g. vancomycin), polypeptide antibiotics (e.g. colistin, polymyxin), carbapenems (such as meropenem); quinolines (such a levaquin); carbacephems; cephamycins; monobactams; quinolones; macrolides; fluoroquinolones; and amphenicole (e.g. chloramphenicol). In one embodiment, the antibiotic is an antisense antibiotic oligomer.

Non-limiting examples of antibiotics also include amoxicillin, tetracycline, metronidazole, rifabutin, clarithromycin, clofazimine, vancomycin, rifampicin, nitroimidazole, chloramphenicol, and a combination thereof. In certain aspects, an antibiotic may be selected from the group consisting of rifaximin, rifamycin derivative, rifampicin, rifabutin, rifapentine, rifalazil, bicozamycin, aminoglycoside, gentamycin, neomycin, streptomycin, paromomycin, verdamicin, mutamicin, sisomicin, netilmicin, retymicin, kanamycin, aztreonam, aztreonam macrolide, clarithromycin, dirithromycin, roxithromycin, telithromycin, azithromycin, bismuth subsalicylate, vancomycin, streptomycin, fidaxomicin, amikacin, arbekacin, neomycin, netilmicin, paromomycin, rhodostreptomycin, tobramycin, apramycin, daptomycin, and a combination thereof.

Additional examples of antibiotics include, but are not limited to, Penicillin G (CAS Registry No.: 61-33-6); Methicillin (CAS Registry No.: 61-32-5); Nafcillin (CAS Registry No.: 147-52-4); Oxacillin (CAS Registry No.: 66-79-5); Cloxacillin (CAS Registry No.: 61-72-3); Dicloxacillin (CAS Registry No.; 3116-76-5); Ampicillin (CAS Registry No.: 69-53-4); Amoxicillin (CAS Registry No.: 26787-78-0); Ticarcillin (CAS Registry No.: 34787-01-4); Carbenicillin (CAS Registry No.: 4697-36-3); Mezlocillin (CAS Registry No.: 51481-65-3); Azlocillin (CAS Registry No.: 37091-66-0); Piperacillin (CAS Registry No.: 61477-96-1); Imipenem (CAS Registry No.: 74431-23-5); Aztreonam (CAS Registry No.: 78110-38-0); Cephalothin (CAS Registry No.: 153-61-7); Cefazolin (CAS Registry No.: 25953-19-9); Cefaclor (CAS Registry No.: 70356-03-5); Cefamandole formate sodium (CAS Registry No.: 42540-40-9); Cefoxitin (CAS Registry No.: 35607-66-0); Cefuroxime (CAS Registry No.: 55268-75-2); Cefonicid (CAS Registry No.: 61270-58-4); Cefinetazole (CAS Registry No.: 56796-20-4); Cefotetan (CAS Registry No.: 69712-56-7); Cefprozil (CAS Registry No.: 92665-29-7); Lincomycin (CAS Registry No.: 154-21-2); Linezolid (CAS Registry No.: 165800-03-3); Loracarbef (CAS Registry No.: 121961-22-6); Cefetamet (CAS Registry No.: 65052-63-3); Cefoperazone (CAS Registry No.: 62893-19-0); Cefotaxime (CAS Registry No.: 63527-52-6); Ceftizoxime (CAS Registry No.: 68401-81-0); Ceftriaxone (CAS Registry No.: 73384-59-5); Ceftazidime (CAS Registry No.: 72558-82-8); Cefepime (CAS Registry No.: 88040-23-7); Cefixime (CAS Registry No.: 79350-37-1); Cefpodoxime (CAS Registry No.: 80210-62-4); Cefsulodin (CAS Registry No.: 62587-73-9); Fleroxacin (CAS Registry No.: 79660-72-3); Nalidixic acid (CAS Registry No.: 389-08-2); Norfloxacin (CAS Registry No.: 70458-96-7); Ciprofloxacin (CAS Registry No.: 85721-33-1); Ofloxacin (CAS Registry No.: 82419-36-1); Enoxacin (CAS Registry No.: 74011-58-8); Lomefloxacin (CAS Registry No.: 98079-51-7); Cinoxacin (CAS Registry No.: 28657-80-9); Doxycycline (CAS Registry No.: 564-25-0); Minocycline (CAS Registry No.: 10118-90-8); Tetracycline (CAS Registry No.: 60-54-8); Amikacin (CAS Registry No.: 37517-28-5); Gentamicin (CAS Registry No.: 1403-66-3); Kanamycin (CAS Registry No.: 8063-07-8); Netilmicin (CAS Registry No.: 56391-56-1); Tobramycin (CAS Registry No.: 32986-56-4); Streptomycin (CAS Registry No.: 57-92-1); Azithromycin (CAS Registry No.: 83905-01-5); Clarithromycin (CAS Registry No.: 81103-11-9); Erythromycin (CAS Registry No.: 114-07-8); Erythromycin estolate (CAS Registry No.: 3521-62-8); Erythromycin ethyl succinate (CAS Registry No.: 41342-53-4); Erythromycin glucoheptonate (CAS Registry No.: 23067-13-2); Erythromycin lactobionate (CAS Registry No.: 3847-29-8); Erythromycin stearate (CAS Registry No.: 643-22-1); Vancomycin (CAS Registry No.: 1404-90-6); Teicoplanin (CAS Registry No.: 61036-64-4); Chloramphenicol (CAS Registry No.: 56-75-7); Clindamycin (CAS Registry No.: 18323-44-9); Trimethoprim (CAS Registry No.: 738-70-5); Sulfamethoxazole (CAS Registry No.: 723-46-6); Nitrofurantoin (CAS Registry No.: 67-20-9); Rifampin (CAS Registry No.: 13292-46-1); Mupirocin (CAS Registry No.: 12650-69-0); Metronidazole (CAS Registry No.: 443-48-1); Cephalexin (CAS Registry No.: 15686-71-2); Roxithromycin (CAS Registry No.: 80214-83-1); Co-amoxiclavuanate; combinations of Piperacillin and Tazobactam; and their various salts, acids, bases, and other derivatives.

The beta-lactam antibiotic agent may be any antibiotic agent which comprises a beta-lactam and is therefore susceptible to degradation by beta-lactamases. Examples include carbapenems (e.g. meropenem, faropenem, imipenem, ertapenem, doripenem, panipenem/betamipron and biapenem as well as razupenem, tebipenem, lenapenem and tomopenem), ureidopenicillins (e.g. piperacillin), carbacephems (e.g. loracarbef) and cephalosporins (e.g. cefpodoxime, ceftazidime, cefotaxime, ceftriaxone, ceftobiprole, and ceftaroline). Specific examples of beta-lactam antibiotic agents include temocillin, piperacillin, cefpodoxime, ceftazidime, cefotaxime, ceftriaxone, meropenem, faropenem, imipenem, loracarbef, ceftobiprole, ceftaroline. Drawz, Clin Microbiol Rev. January 2010; 23(1): 160-201.

Non-limiting examples of penicillins include, Amdinocillin, Amoxicillin (e.g. NOVAMOX, AMOXIL); Ampicillin (e.g. PRINCIPEN); Azlocillin; Carbenicillin (e.g. GEOCILLIN); Cloxacillin (e.g. TEGOPEN); Cyclacillin, Dicloxacillin (e.g. DYNAPEN); Flucloxacillin (e.g. FLOXAPEN); Mezlocillin (e.g. MEZLIN); Methicillin (e.g. STAPHCILLIN); Nafcillin (e.g. UNIPEN); Oxacillin (e.g. PROSTAPHLIN); Penicillanic Acid, Penicillin G (e.g. PENTIDS or PFIZERPEN); Penicillin V (e.g. VEETIDS (PEN-VEE-K)); Piperacillin (e.g. PIPRACIL); Sulbactam, Temocillin (e.g. NEGABAN); and Ticarcillin (e.g. TICAR).

Non-limiting examples of cephalosporins include, a first generation cephalosporin (e.g. Cefadroxil (e.g. DURICEF); Cefazolin (e.g. ANCEF); Ceftolozane, Cefalotin/Cefalothin (e.g. KEFLIN); Cefalexin (e.g. KEFLEX); a second generation cephalosporin (e.g. Cefaclor (e.g. DISTACLOR); Cefamandole (e.g. MANDOL); Cefoxitin (e.g. MEFOXIN); Cefprozil (e.g. CEFZIL); Cefuroxime (e.g. CEFTIN, ZINNAT)); a third generation cephalosporin (e.g. Cefixime (e.g. SUPRAX); Cefdinir (e.g. OMNICEF, CEFDIEL); Cefditoren (e.g. SPECTRACEF); Cefoperazone (e.g. CEFOBID); Cefotaxime (e.g. CLAFORAN); Cefpodoxime (e.g. VANTIN); Ceftazidime (e.g. FORTAZ); Ceftibuten (e.g. CEDAX) Ceftizoxime (e.g. CEFIZOX); and Ceftriaxone (e.g. ROCEPHIN)); a fourth generation cephalosporin (e.g. Cefepime (e.g. MAXIPIME)); or a fifth generation cephalosporin (e.g. Ceftaroline fosamil (e.g. TEFLARO); Ceftobiprole (e.g. ZEFTERA)). Also included is Latamoxef (or moxalactam). In a specific embodiment, cephalosporins include, for example, cefoperazone, ceftriaxone or cefazolin.

Non-limiting examples of monobactams include, aztreonam (e.g. AZACTAM, CAYSTON), tigemonam, nocardicin A, and tabtoxin.

Non-limiting examples of carbapenems include, meropenem, imipenem (by way of non-limiting example, imipenem/cilastatin), ertapenem, doripenem, panipenem/betamipron, biapenem, razupenem (PZ-601), tebipenem, lenapenem, thienamycins, and tomopenem.

Bacterial Infections

The present compositions and methods may be used to treat, or treat prophylactically, bacterial infection. The bacterial infection may be caused by, or associated with, Gram-negative or Gram-positive bacteria. For example, the bacterial infection may be caused by, or associated with, bacteria from one or more of the families *Clostridium, Pseudomonas, Escherichia, Klebsiella, Enterococcus, Enterobacter, Serratia, Morganella, Yersinia, Salmonella, Proteus, Pasteurella, Haemophilus, Citrobacter, Burkholderia, Brucella, Moraxella, Mycobacterium, Streptococcus* or *Staphylococcus*. Particular examples include *Clostridium, Pseudomonas, Escherichia, Klebsiella, Enterococcus, Enterobacter, Streptococcus* and *Staphylococcus*. The bacterial infection may be caused by, or associated with, one or more bacteria selected from *Moraxella catarrhalis, Brucella abortus, Burkholderia cepacia, Citrobacter species, Escherichia coli, Haemophilus Pneumonia, Klebsiella Pneumonia, Pasteurella multocida, Proteus mirabilis, Salmonella typhimurium, Clostridium difficile, Yersinia enterocolitica Mycobacterium tuberculosis, Staphylococcus aureus*, group B streptococci, *Streptococcus Pneumonia*, and *Streptococcus pyogenes*, e.g., from *E. coli* and *K. pneumoniae*.

Gram-negative bacteria are typically free-living organisms often found in soil and water, and play an important role in decomposition, biodegradation, and the C and N cycles. However, many gram-negative bacteria are pathogenic.

For example, the bacterial infection may be caused by, or associated with, gram-negative bacteria including, but not limited to, *Pseudomonas* (including, but not limited to *Pseudomonas aeruginosa*), *Burkholderia cepaci, C. violaceum, V harveyi, Neisseria gonorrhoeae, Neisseria meningitidis, Bordetell pertussis, Haemophilus influenzae, Legionella pneuinophila, Brucella, Francisella, Xanthomonas, Agrobacterium*, enteric bacteria, such as *Escherichia coli* and its relatives, the members of the family Enterobacteriaceae, such as *Salmonella* and *Shigella, Proteus*, and *Yersinia pestis*. U.S. Pat. No. 9,751,851.

Gram-negative bacteria that can be inhibited by the present compositions include, but are not limited to, *Pseudomonas* (including, but not limited to *Pseudomonas aeruginosa*), *Burkholderia cepaci, C. violaceum, V harveyi, Neisseria gonorrhoeae, Neisseria meningitidis, Bordetell pertussis, Haemophilus influenzae, Legionella pneuinophila, Brucella, Francisella, Xanthomonas, Agrobacterium*, enteric bacteria, such as *Escherichia coli* and its relatives, the members of the family Enterobacteriaceae, such as *Salmonella* and *Shigella, Proteus*, and *Yersinia pestis*.

The present compositions and methods can be used to treat, or treat prophylactically, infections of the pulmonary tract, urinary tract, burns, and wounds, caused by, or associated with, gram negative bacteria such as *P. aeruginosa*. The present compositions and methods can be used to treat, or treat prophylactically, catheter-associated infections, blood infections, middle ear infections, formation of dental plaque, gingivitis, chronic sinusitis, endocarditis, coating of contact lenses, and infections associated with implanted devices (e.g., catheters, joint prostheses, prosthetic cardiac valves and intrauterine devices), caused by, or associated with, gram negative bacteria such as *P. aeruginosa*. The present compositions and methods can be used to treat, or treat prophylactically, infections of the central nervous system, gastrointestinal tract, bones, joints, ears and eyes, caused by, or associated with, gram negative bacteria such as *P. aeruginosa*.

The present compositions and methods can be used to treat, or treat prophylactically, inhibit, and/or ameliorate infections including opportunistic infections and/or antibiotic resistant bacterial infections caused by gram negative bacteria. Examples of such opportunistic infections, include, but are not limited to *P. aeruginosa*. or poly-microbial infections of *P. aeruginosa* with, for example, *Staphylococcus aureus* or *Burkholderia cepacia*. Examples of patients who may acquire such opportunistic and/or resistant infections include, but are not limited to, patients who are immunocompromised or immunosuppressed, who have cystic fibrosis or HIV, who have implanted medical devices, subcutaneous devices or who are on ventilators, patients who have been intubated, patients who have catheters, patients who have nosocomial infections, patients who are undergoing bone marrow transplant or other types of surgery, including, but not limited to dental surgery, and patients who are IV drug users, especially with regard to heart valve infection.

The present compositions and methods can be used to treat, or treat prophylactically, burns and/or other traumatic wounds as well as common or uncommon infections. Examples of such wounds and infection disorders include, but are not limited to puncture wounds, radial keratotomy, ecthyma gangrenosum, osteomyelitis, external otitis, and/or dermatitis.

In one embodiment, the present compositions and methods can be used to treat, treat prophylactically, prevent, and/or ameliorate pulmonary infections. In one embodiment, the present compositions and methods can be used to treat, treat prophylactically, prevent, and/or ameliorate pneumonia. Pneumonia can be caused by colonization of medical devices, such as ventilator-associated pneumonia, and other nosocomial pneumonia. In one embodiment, the present compositions and methods can be used to treat, treat prophylactically, prevent, and/or ameliorate lung infections, such as pneumonia, in cystic fibrosis patients. In one embodiment, the present compositions and methods can be used to treat, treat prophylactically, prevent, and/or ameliorate an infection caused by, or associated with, gram negative bacteria (such as by *P. aeruginosa*) in cystic fibrosis patients.

The present compositions and methods can be used to treat, treat prophylactically, prevent, and/or ameliorate septic shock. The present compositions and methods can be used to treat, treat prophylactically, prevent, and/or ameliorate septic shock in neutropenic, immunocompromised, and/or immunosuppressed patients or patients infected with antibiotic resistant bacteria, such as, for example, antibiotic resistant *P. aeruginosa*.

The present compositions and methods can be used to treat, treat prophylactically, prevent, and/or ameliorate urinary tract or pelvic infections. The present compositions and methods can be used to treat, treat prophylactically, prevent, and/or ameliorate gastrointestinal infections, such as necrotizing enterocolitis, often seen in premature infants and/or neutropenic cancer patients.

The present compositions and methods can be used to treat, treat prophylactically, prevent, and/or ameliorate urinary dysentery (for example, dysentery caused by bacillary dysentery), food poisoning and/or gastroenteritis (for example, caused by *Salmonella enterica*), typhoid fever (for example, caused by *Salmonella typhi*), whooping cough (or pertussis) as is caused by *Bordetella pertussis*, Legionnaires' pneumonia, caused by *Legionella pneumophila*, sexually transmitted diseases, such as gonorrhea, caused by *Neisseria gonorrhoeae*, or meningitis, caused by, for example, *Neisseria meningitidis* or *Haemophilus influenzae*, brucellosis which is caused by brucellae, and more specifically, *Brucella abortus*.

The present compositions and methods may be used to attenuate bacterial virulence.

In one embodiment, the present compositions are administered to a subject who is free of bacterial disease. Administration may be in advance of an anticipated health-related procedure known to increase susceptibility to gram-negative bacteria (e.g., *P. aeruginosa*) pathogenicity, for example, in advance of a surgical procedure, including dental procedures, procedures involving implants, and/or insertion of catheters or other devices.

In other embodiments, the present compositions may be present in suspensions, syrups, elixirs, solutions, pills, capsules, suppositories and tablets for oral systemic use.

Combination Therapy

The present composition may be administered alone or in combination with other compounds, such as an antibiotic, an antimicrobial agent, a probiotic, and/or an anti-inflammatory agent. In certain embodiments, the present composition may be administered in combination with one or more antibiotics. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

The present method for treating a bacterial infection may comprise the step of administering to a subject an antibiotic and a dietary fiber (e.g., inulin).

This may be achieved by administering a composition that includes both agents (e.g., an antibiotic and a dietary fiber (e.g., inulin), or an antimicrobial agent and a dietary fiber (e.g., inulin), or by administering two compositions, at the same time or within a short time period, wherein one composition comprises an antibiotic, and the other composition includes a dietary fiber (e.g., inulin).

Antimicrobial agents include, but are not limited to, triclosan, metronidazole, tetracyclines, quinolones, plant essential oils, camphor, thymol, carvacrol, menthol, eucalyptol, methyl salicylate, tobramycin, cetylpyridinium chloride, neomycin, polymyxin, bacitracin, clindamycin, ciprofloxacin, rifampin, oxfloxacin, macrolides, penicillins, cephalosporins, amoxicillin/clavulanate, quinupristin/dalfopristin, amoxicillin/sulbactum, fluoroquinolones, ketolides, aminoglycosides and mixtures thereof.

Antimicrobial agents also include, but are not limited to, Aerucin (AR-105), LST007, and phosphorodiamidate morpholino oligomers (PPMOs). Aerucin (AR-105) is a broadly active, fully human IgG1 monoclonal antibody targeting *P. aeruginosa* alginate, a widely distributed cell surface polysaccharide involved in surface adhesion, biofilm formation, and protection against the human immune system. LST007 is a monoclonal antibody that targets the exposed virulence factor flagellin type b on *P. aeruginosa* cells. Peptide-conjugated phosphorodiamidate morpholino oligomers (PPMOs) inhibit translation of complementary mRNA from specific, essential genes in *P. aeruginosa*.

Anti-inflammatory agents include, but are not limited to, steroidal anti-inflammatory actives, non-steroidal anti-inflammatory actives and mixtures thereof. Suitable steroidal anti-inflammatory agents include, but are not limited to, hydrocortisone, fluocinolone acetonide, halcinonide, halobetasol propionate, clobetasol propionate, betamethasone dipropionate, betamethasone valerate, triamcinolone acetonide and mixtures thereof. Suitable non-steroidal anti-inflammatory actives include, but are not limited to, salicylic acid derivatives such as aspirin, sodium salicylate, choline magnesium salicylate, salsalate, diflunisal, salicylsalicylic acid, sulfasalazine, and olsalazine; para-aminophenol derivatives such as acetaminophen; indole and indene acetic acids such as indomethacin, sulindac, and etodolac; heteroaryl acetic acids such as tolmetin, diclofenac, and ketorolac; arylpropionic acids such as ibuprofen, naproxen, flurbiprofen, ketoprofen, fenoprofen, and oxaprozin; anthranilic acids (fenamates) such as oxicams (piroxicam, tenoxicam), pyrazolidineones (phenylbutazone, oxyphenthatrazone); alkanones such as nabumetone; apazone (azapropazone); nimesulide; and mixtures thereof.

The antibiotic (or the probiotic, or the antimicrobial agent, or the anti-inflammatory agent) and the dietary fiber (e.g., inulin) may be administered simultaneously, separately or sequentially. They may exert an advantageously combined effect (e.g., additive or synergistic effects).

For sequential administration, either an antibiotic (or a probiotic, or an antimicrobial agent, and/or an anti-inflammatory agent) is administered first and then a dietary fiber (e.g., inulin), or the dietary fiber (e.g., inulin) is administered first and then an antibiotic (or a probiotic, or an antimicrobial agent, and/or an anti-inflammatory agent). In embodiments where the antibiotic (or a probiotic, or an antimicrobial agent, and/or an anti-inflammatory agent) and a dietary fiber (e.g., inulin) are administered separately, administration of a first agent can precede administration of a second agent by seconds, minutes, hours, days, or weeks. The time difference in non-simultaneous administrations may be greater than 1 minute, and can be, for example, precisely, at least, up to, or less than 5 minutes, 10 minutes, 15 minutes, 30 minutes, 45 minutes, 60 minutes, 2 hours, 3 hours, 6 hours, 9 hours, 12 hours, 24 hours, 36 hours, or 48 hours, or more than 48 hours. The two or more agents can be administered within minutes of each other or within about 0.5, about 1, about 2, about 3, about 4, about 6, about 9, about 12, about 15, about 18, about 24, or about 36 hours of each other or within about 1, 2, 3, 4, 5, 6, 7, 8, 9, 10, 12, 14 days of each other or within about 2, 3, 4, 5, 6, 7, 8, 9, or 10 weeks of each other. In some cases, longer intervals are possible.

Compositions

The present composition may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents, gel forming agents, antioxidants and antimicrobials.

The composition may comprise a source of protein. Any suitable dietary protein may be used, for example animal proteins (such as milk proteins, meat proteins and egg proteins); vegetable proteins (such as soy protein, wheat protein, rice protein, and pea protein); mixtures of free amino acids; or combinations thereof. The proteins may be intact, hydrolyzed, partially hydrolyzed or a mixture thereof.

The composition may also contain another source of carbohydrates and a source of fat.

The compositions can be, e.g., in a solid, semi-solid, or liquid formulation. Compositions can also take the form of tablets, pills, capsules, semisolids, powders, sustained release formulations, emulsions, suspensions, or any other appropriate compositions.

The present composition may be in the form of: an enema composition which can be reconstituted with an appropriate diluent; enteric-coated capsules or microcapsules; powder for reconstitution with an appropriate diluent for naso-enteric infusion, naso-duodenal infusion or colonoscopic infusion; powder for reconstitution with appropriate diluent, flavoring and gastric acid suppression agent for oral ingestion; or powder for reconstitution with food or drink. U.S. Patent Publication No. 20140234260.

The composition may also contain conventional pharmaceutical additives and adjuvants, excipients and diluents, including, but not limited to, water, gelatine of any origin, vegetable gums, ligninsulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like. In all cases, such further components will be selected having regard to their suitability for the intended recipient. U.S. Pat. No. 8,741,622.

Appropriate frequency of administration can be determined by one of skill in the art and can be administered once or several times per day (e.g., twice, three, four or five times daily). The compositions of the invention may also be administered once each day or once every other day. The compositions may also be given twice weekly, weekly, monthly, or semi-annually. U.S. Pat. No. 8,501,686.

The amount of a dietary fiber (e.g., inulin), or an antibiotic (or an antimicrobial agent, and/or an anti-inflammatory agent) that may be used in the combination therapy may be a therapeutically effective amount, a sub-therapeutically effective amount or a synergistically effective amount.

An antibiotic (or a probiotic, or an antimicrobial agent, and/or an anti-inflammatory agent), and/or a dietary fiber (e.g., inulin) may be present in the pharmaceutical composition in an amount ranging from about 0.005% (w/w) to about 100% (w/w), from about 0.01% (w/w) to about 90% (w/w), from about 0.1% (w/w) to about 80% (w/w), from about 1% (w/w) to about 70% (w/w), from about 10% (w/w) to about 60% (w/w), from about 0.01% (w/w) to about 15% (w/w), or from about 0.1% (w/w) to about 20% (w/w).

An antibiotic (or a probiotic, or an antimicrobial agent, and/or an anti-inflammatory agent) and a dietary fiber (e.g., inulin) may be present in two separate pharmaceutical compositions to be used in a combination therapy.

The present agents or pharmaceutical compositions may be administered by any route, including, without limitation, oral, transdermal, ocular, intraperitoneal, intravenous, ICV, intracisternal injection or infusion, subcutaneous, implant, sublingual, subcutaneous, intramuscular, intravenous, rectal, mucosal, ophthalmic, intrathecal, intra-articular, intra-arterial, sub-arachinoid, bronchial and lymphatic administration. The present composition may be administered parenterally or systemically.

The pharmaceutical compositions of the present invention can be, e.g., in a solid, semi-solid, or liquid formulation. Intranasal formulation can be delivered as a spray or in a drop; inhalation formulation can be delivered using a nebulizer or similar device; topical formulation may be in the form of gel, ointment, paste, lotion, cream, poultice, cataplasm, plaster, dermal patch aerosol, etc.; transdermal formulation may be administered via a transdermal patch or iontorphoresis. Compositions can also take the form of tablets, pills, capsules, semisolids, powders, sustained release formulations, solutions, emulsions, suspensions, elixirs, aerosols, chewing bars or any other appropriate compositions.

The composition may be administered locally via implantation of a membrane, sponge, or another appropriate material on to which the desired molecule has been absorbed or encapsulated. Where an implantation device is used, the device may be implanted into any suitable tissue or organ, and delivery of the desired molecule may be via diffusion, timed release bolus, or continuous administration.

To prepare such pharmaceutical compositions, one or more of compound of the present invention may be mixed with a pharmaceutical acceptable excipient, e.g., a carrier, adjuvant and/or diluent, according to conventional pharmaceutical compounding techniques.

Pharmaceutically acceptable carriers that can be used in the present compositions encompass any of the standard pharmaceutical carriers, such as a phosphate buffered saline solution, water, and emulsions, such as an oil/water or water/oil emulsion, and various types of wetting agents. The compositions can additionally contain solid pharmaceutical excipients such as starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Liquid carriers, particularly for injectable solutions, include water, saline, aqueous dextrose, and glycols. For examples of carriers, stabilizers, preservatives and adjuvants, see Remington's Pharmaceutical Sciences, edited by E. W. Martin (Mack Publishing Company, 18th ed., 1990). Additional excipients, for example sweetening, flavoring and coloring agents, may also be present.

The pharmaceutically acceptable excipient may be selected from the group consisting of fillers, e.g. sugars and/or sugar alcohols, e.g. lactose, sorbitol, mannitol, maltodextrin, etc.; surfactants, e.g. sodium lauryle sulfate, Brij 96 or Tween 80; disintegrants, e.g. sodium starch glycolate, maize starch or derivatives thereof; binder, e.g. povidone, crosspovidone, polyvinylalcohols, hydroxypropylmethylcellulose; lubricants, e.g. stearic acid or its salts; flowability enhancers, e.g. silicium dioxide; sweeteners, e.g. aspartame; and/or colorants. Pharmaceutically acceptable carriers include any and all clinically useful solvents, dispersion media, coatings, antibacterial and antifungal agents, isotonic and absorption delaying agents and the like.

The pharmaceutical composition may contain excipients for modifying, maintaining or preserving, for example, the pH, osmolarity, viscosity, clarity, color, isotonicity, odor, sterility, stability, rate of dissolution or release, adsorption or penetration of the composition. Suitable excipients include, but are not limited to, amino acids (such as glycine, glutamine, asparagine, arginine or lysine); antimicrobials; antioxidants (such as ascorbic acid, sodium sulfite or sodium hydrogen sulfite); buffers (such as borate, bicarbonate, Tris HCl, citrates, phosphates, other organic acids); bulking agents (such as mannitol or glycine), chelating agents (such as ethylenediamine tetraacetic acid (EDTA), ethylene glycol tetraacetic acid (EGTA)); complexing agents (such as caffeine, polyvinylpyrrolidone, beta cyclodextrin or hydroxypropyl beta cyclodextrin); fillers; monosaccharides; disaccharides and other carbohydrates (such as glucose, mannose, or dextrins); proteins (such as serum albumin, gelatin or immunoglobulins); coloring; flavoring and diluting agents; emulsifying agents; hydrophilic polymers (such as polyvinylpyrrolidone); low molecular weight polypeptides; salt forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (sucrose or sorbitol); tonicity enhancing agents (such as alkali metal halides (in one aspect, sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company, 1990).

Oral dosage forms may be tablets, capsules, bars, sachets, granules, syrups and aqueous or oily suspensions. Tablets may be formed form a mixture of the active compounds with fillers, for example calcium phosphate; disintegrating agents, for example maize starch, lubricating agents, for example magnesium stearate; binders, for example microcrystalline cellulose or polyvinylpyrrolidone and other optional ingredients known in the art to permit tabletting the mixture by known methods. Similarly, capsules, for example hard or soft gelatin capsules, containing the active compound, may be prepared by known methods. The contents of the capsule may be formulated using known methods so as to give sustained release of the active compounds. Other dosage forms for oral administration include, for example, aqueous suspensions containing the active compounds in an aqueous medium in the presence of a non-toxic suspending agent such as sodium carboxymethylcellulose, and oily suspensions containing the active compounds in a suitable vegetable oil, for example arachis oil. The active compounds may be formulated into granules with or without additional excipients. The granules may be ingested directly by the patient or they may be added to a suitable liquid carrier (e.g. water) before ingestion. The granules may contain disintegrants, e.g. an effervescent pair formed from an acid and a carbonate or bicarbonate salt to facilitate dispersion in the liquid medium. U.S. Pat. No. 8,263,662.

Additional compositions include formulations in sustained or controlled delivery, such as using liposome or micelle carriers, bioerodible microparticles or porous beads and depot injections. The pharmaceutical composition can be prepared in single unit dosage forms.

Appropriate frequency of administration can be determined by one of skill in the art and can be administered once or several times per day (e.g., twice, three, four or five times daily). The compositions of the invention may also be administered once each day or once every other day. The compositions may also be given twice weekly, weekly, monthly, or semi-annually. In the case of acute administration, treatment is typically carried out for periods of hours or days, while chronic treatment can be carried out for weeks, months, or even years.

The amount of an antibiotic (or a probiotic, or an antimicrobial agent, and/or an anti-inflammatory agent) (e.g., a first amount) or the amount of a dietary fiber (e.g., inulin) (e.g., a second amount) that may be used in the combination therapy may be a therapeutically effective amount, a subtherapeutically effective amount or a synergistically effective amount.

Kits

The present invention also provides for a kit for use in the treatment or prevention of a bacterial infection or for other uses as described herein. Kits include package(s) (e.g., vessels) comprising the present agents or compositions. The kit may include the present composition, and optionally an antibiotic and/or a probiotic. The present composition may be present in unit dosage forms.

Examples of pharmaceutical packaging materials include, but are not limited to, bottles, tubes, inhalers, pumps, bags, vials, containers, syringes, bottles, and any packaging material suitable for a selected formulation and intended mode of administration and treatment.

The kit can contain instructions for administering the present agents or compositions to a patient. The kit can comprise instructions for uses of the present agents or compositions. The kit can contain labeling or product inserts for the present agents or compositions. The kits also can include buffers for preparing solutions for conducting the methods.

Subjects, which may be treated according to the present invention include all animals which may benefit from the present invention. Such subjects include mammals, preferably humans (infants, children, adolescents and/or adults), but can also be an animal such as dogs and cats, farm animals such as cows, pigs, sheep, horses, goats and the like, and laboratory animals (e.g., rats, mice, guinea pigs, and the like).

"Treating" or "treatment" of a state, disorder or condition includes: (1) preventing or delaying the appearance of clinical symptoms of the state, disorder, or condition developing in a person who may be afflicted with or predisposed to the state, disorder or condition but does not yet experience or display clinical symptoms of the state, disorder or condition; or (2) inhibiting the state, disorder or condition, i.e., arresting, reducing or delaying the development of the disease or a relapse thereof (in case of maintenance treatment) or at least one clinical symptom, sign, or test, thereof; or (3) relieving the disease, i.e., causing regression of the state, disorder or condition or at least one of its clinical or sub-clinical symptoms or signs.

The benefit to a subject to be treated is either statistically significant or at least perceptible to the patient or to the physician.

The compositions of the invention may include a "therapeutically effective amount" or a "prophylactically effective amount" of a compound described herein. A "therapeutically effective amount" refers to an amount effective, at dosages and for periods of time necessary, to achieve the desired therapeutic result. A therapeutically effective amount of an antibody or antibody portion may vary according to factors such as the disease state, age, sex, and weight of the individual, and the ability of the antibody or antibody portion to elicit a desired response in the individual. A therapeutically effective amount is also one in which any toxic or detrimental effects of the agent are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount may be less than the therapeutically effective amount.

Suitable samples for detecting or determining the presence or level of at least one bacterial strain, may include, but are not limited to, rectal swabs, stool samples, stool (i.e., feces), whole blood, plasma, serum, saliva, urine, tears, and any other bodily fluid, or a tissue sample (i.e., biopsy) such as a small intestine or colon sample.

In one embodiment, the present composition is administered as an oral formulation. Oral dosage forms are well known in the art and include tablets, caplets, gelcaps, capsules, and medical foods. Tablets, for example, can be made by well-known compression techniques using wet, dry, or fluidized bed granulation methods.

Such oral formulations may be presented for use in a conventional manner with the aid of one or more suitable excipients, diluents, and carriers. Pharmaceutically acceptable excipients assist or make possible the formation of a dosage form for a bioactive material and include diluents, binding agents, lubricants, glidants, disintegrants, coloring agents, and other ingredients. Preservatives, stabilizers, dyes and even flavoring agents may be provided in the pharmaceutical composition. Examples of preservatives include sodium benzoate, ascorbic acid and esters of p-hydroxybenzoic acid. Antioxidants and suspending agents may be also used. An excipient is pharmaceutically acceptable if, in addition to performing its desired function, it is non-toxic, well tolerated upon ingestion, and does not interfere with absorption of bioactive materials.

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

As used herein, the term "bacteria" encompasses both prokaryotic organisms and archaea present in mammalian microbiota.

The terms "intestinal microbiota", "gut flora", and "gastrointestinal microbiota" are used interchangeably to refer to bacteria in the digestive tract.

The term "Eubacteria" refers to all bacteria and excludes archaea. In mammals, >90% of all colonic bacteria are in the phyla Firmicutes or Bacteroidetes (Ley et al., Nat Rev Microbiol 2008; 6:776-88).

The following are examples of the present invention and are not to be construed as limiting.

Example 1 Rapid Loss of Clostridial Clusters IV and XIVa in the ICU Associates with an Expansion of Pathogens Commensal gastrointestinal bacteria resist the expansion of pathogens and are lost during initial treatment in the intensive care unit (ICU). A diverse and stable gastrointestinal flora has been associated with decreased risk for colonization with organisms such as vancomycin-resistant *Enterococcus* (VRE) and for subsequent infections. However, which specific bacteria may contribute most to the diversity and stability of the gut microbiome during critical illness is unknown. We performed a prospective, ICU based study to determine within-individual changes in the gut microbiome during initial treatment in the ICU and how these changes associate with overall gut microbiome diversity and stability. Deep rectal swabs were performed on adult ICU patients within 4 hours of ICU admission and exactly 72 hours later, and analyzed using 16S rRNA gene sequencing and bacterial culture for VRE. Microbiome data was visualized using principal coordinate analyses (PCoA) and assessed using a linear discriminant analysis algorithm and logistic regression modeling.

A total of 93 ICU patients were analyzed. At 72 hours following ICU admission, 16S rRNA gene sequencing showed significant within-individual losses in Clostridial Clusters IV and XIVa, bacterial taxa that produce short chain fatty acids (SCFAs). At the same time, there was a significant expansion in *Enterococcus*. Culture results suggested that the expansion in *Enterococcus* was driven by VRE. Decreases in Cluster IV/XIVa Clostridia were associated with reduced microbiome diversity and with decreased community stability over time. In multivariable analysis, both decreased Cluster IV/XIVa Clostridia and increased *Enterococcus* after 72 hours were associated with receipt of broad-spectrum antibiotics. Cluster IV/XIVa Clostridia, although a small fraction of the overall gastrointestinal microbiome, drove distinct clustering on PCoA; levels of these Clostridia were inversely associated with levels of *Enterococcus*.

During initial treatment for critical illness, there was a loss of SCFA-producing Clostridia within the distal gut microbiome which associated with an expansion of VRE and with a loss of microbiome diversity and stability within the gut microbiome. Receipt of broad-spectrum antibiotics was associated with these changes.

Background

The gut microbiome substantially shifts during critical illness, both from critical illness itself and from antibiotics and other interventions common to the intensive care unit (ICU) [1]. The normal gastrointestinal microbiome plays crucial roles in metabolism and nutrition, maintenance of the mucosal barrier, and immunity. All of these roles are likely to be affected during treatment of ICU patients, who often have multi-organ dysfunction, are deprived of enteric nutrition, are often treated with broad-spectrum antibiotics, and experience immune dysfunction from immunosuppressive medications, sepsis, or both.

Loss of colonization resistance, the ability of the normal gut microbiome to resist the expansion of pathogens, is thought to be a risk factor for ICU-acquired infections and may contribute to the organ dysfunction seen during sepsis [2, 3]. Typical hospital pathogens such as Gram-negative bacilli and vancomycin-resistant *Enterococcus* (VRE) are more prevalent in ICU patients compared to healthy adults and the density of Gram-negative colonization correlates with severity of illness [4]. Fecal microbial diversity, a proxy measure for colonization resistance, is low at the time of ICU admission [5] and further declines with treatment; prolonged critical illness and the accompanying antibiotics may lead to a state of ultra-low diversity and near-complete loss of colonization resistance [6]. In bone marrow transplant patients, loss of fecal microbial diversity is followed by domination with enteric pathogens including VRE and increased risk for subsequent infection [7, 8].

The specific changes that lead to loss of normal colonization resistance are uncertain. Loss of obligate anaerobes may facilitate the acquisition of pathogens and has been observed as a consequence of antibiotics [9-11]. In particular, loss of Clostridial Clusters IV and XIVa, which produce butyrate and other short chain fatty acids (SCFA), has been correlated with susceptibility to enteric pathogens [12]. In small ICU-based studies, loss of anaerobes has been associated with increases in *Enterococcus* and *Staphylococcus* [13]. Large shifts away from anaerobic commensals have been seen in the ICU and have been associated with worse clinical outcomes [14, 15]. However, it is unknown exactly which bacteria or combination of bacteria are lost, when, and how they may maintain colonization resistance.

We conducted this study to determine the key fecal microbial changes during the period immediately following ICU admission. Our goal was to identify potentially protective bacterial taxa that might be lost during this initial ICU treatment period, and to test which clinical factors were associated with these changes.

Methods

Patient Population.

Adults ≥18 years old were considered for the study if they were newly admitted to any one of 5 distinct medical or surgical ICUs and could be reached within 4 hours of ICU admission. Patients were excluded for prior *Clostridium difficile* infection (within 90 days), bacterial bloodstream infections (within 30 days), or ICU admissions (within 30 days). Patients were also excluded if both study assessments could not be completed due to death, discharge, or patient refusal. Informed consent was obtained from all subjects or from appropriate surrogates. This study was approved by the institutional review board of Columbia University.

Study Design.

This was a prospective, ICU-based study consisting of two assessments. The initial study assessment was made within 4 hours of ICU admission and the second and final study assessment was performed 72 hours later (+/−4 hours).

Study Assessments.

At each study assessment, samples were taken and information was gathered. Two duplicate deep rectal flocked nylon swabs [16] (Copan Diagnostics, Murrieta, Calif.) were performed and the following information was gathered at the bedside: vital signs, use of life support devices (e.g., mechanical ventilation, hemodialysis), and the Glasgow Coma Scale [17]. Demographic information, laboratory data, and data related to interventions performed in the ICU between study visits was extracted from the electronic medical record. For laboratory data, test results were used from the first venous blood draw in the ICU (corresponding to the first study assessment) and from a venous blood draw either at or immediately preceding the 72-hour mark (corresponding to the second study assessment). ICU interventions were recorded including antibiotics (any dose or duration), proton pump inhibitors, mechanical ventilation, hemodialysis (either intermittent or continuous), and enteral feeding (by mouth or by naso-enteric tube). Clinical and laboratory data were used to estimate acute severity of illness (APACHE IV) [18].

16S rRNA Gene Sequencing.

The first of each pair of duplicate swabs was frozen at −80° C. for batched DNA extraction at the end of the study (PowerFecal, MoBio, Carlsbad, Calif.). Polymerase chain reaction was performed targeting the V4 hypervariable region of the 16S ribosomal RNA gene with primers derived from the human microbiome project [19]. Samples were pooled and purified with the QIAquick PCR kit (Qiagen, Valencia, Calif.) and library quantification performed using a KAPA Library Quantification Kit (Kapa Biosystems, Wilmington, Mass.). Sequencing of the 16S ribosomal RNA gene V4 region was performed using the Illumina HiSeq 4000 platform (Illumina, San Diego, Calif.). The QIIME pipeline [20] was used to calculate $\alpha$- and $\beta$-diversity indices and to generate principal coordinate analysis (PCoA) plots.

16S rRNA Sequencing Analysis.

Singleton reads were discarded and read pairs were merged, trimmed, and filtered for quality using mothur (52). Subsequently singleton contigs were discarded. Greengenes (53) was used as a reference database with additional sequences of interest retrieved from the National Center for Biotechnology as needed. Clustering of taxonomic units was made at 97% sequence similarity using USEARCH (54) and taxonomic assignments were made using mothur (1). FastTree2 (55) was used to generate a phylogenetic tree of the contigs and QIIME (56) was used to calculate α- and β-diversity indices including weighted and unweighted UniFrac distances (57), and to generate principal coordinate analysis (PCoA) plots.

VRE-Selective Stool Culture.

At both study assessments, duplicate rectal swabs were performed and were inoculated into soy broth with 20% glycerol media at the bedside. After gentle mixing, these swabs were plated on VRE-selective chromogenic media (Remel, Lenexa Kans.) and incubated aerobically at 33-37° C. After 24 hours, colonies were inspected for characteristics, morphology, and color. Results were classified categorically according to the manufacturer's instructions as VRE present (including *E. 154 faecalis* or *E. faecium*) versus VRE absent.

Statistical Approach.

Comparisons of clinical data were performed using chi-squared tests, Fisher's exact test (when expected cell counts were ≤5), or paired t tests for continuous variables.

Analysis of gut microbiome data was performed using a stepwise approach. First, an untargeted hierarchical linear discriminant analysis (LDA) effect size algorithm (LEfSe) [21] was used to identify significant within-individual changes, comparing the time of ICU admission versus 72 hours later. LEfSe tests for non-parametric differences in features (Kruskal-Wallis) and uses these results for paired testing for a difference between pre-specified classes (Wilcoxon rank-sum). A LDA cut-off of ≥2.0 was applied and all taxa were specified at the lowest possible hierarchical level. LEfSe can exaggerate the importance of scarce taxa, so this analysis was limited to taxa that had both significantly changed and that had a relative abundance ≥0.005 in any sample. Second, the univariable relationships between clinical data and taxa identified as significantly changed by LEfSe were examined. For this analysis, LEfSe taxa were divided into quartiles based on relative abundance after 72 hours. Third, a multivariable model was constructed for these relationships using ordered logistic regression. Variables considered for this model had an unadjusted relationship with LEfSe taxa at the p<0.10 level. To further explore the data, sensitivity analyses were performed testing for relationships between dynamic clinical changes and altered 176 LEfSe taxa within the final model (e.g., worsening APACHE IV).

Post hoc clustering analyses were performed selecting cut-offs based on the observed data. To test for differences in alpha diversity, the Wilcoxon U test and was used with GraphPad Prism 7 (La Jolla, Calif.). To test for differences in beta diversity, unweighted UniFrac distances were used with QIIME after a Bonferroni-adjusted Monte Carlo simulation [20]. STATA 14 (StataCorp, College Station, Tex.) was used for multivariable modeling and other significance testing. All tests were performed 2-sided at the alpha 0.05 level.

Results

Clinical Characteristics

A total of 192 patients were approached to enroll 109 subjects including 93 who completed both study assessments and were analyzed (16 subjects died or refused the second assessment). For two subjects, there were <1,000 16S reads obtained from the swabs performed at ICU admission and these samples were excluded; the median sequence depth per sample for the remainder of the samples exceeded 1,000,000. Sequencing data from this study has been made available in the short read archive section of the National Center for Biotechnology Information.

Many subjects had evidence of hemodynamic instability at the time of ICU admission and most had anemia, leukocytosis, or renal insufficiency (Table 4). Most patients were clinically improving during treatment in the ICU with a median decline of 12 points in the APACHE IV score (p<0.01) representing decreased severity of illness. However, over the 72 hours following ICU admission, patients were also significantly more likely to develop new fever, anemia, or hypoalbuminemia (Table 4). During this initial 72-hour period, 77% of subjects received broad-spectrum antibiotics including 25% who received vancomycin (Table 1).

Within-Individual Changes in the Gut Microbiome

Figure 1B:
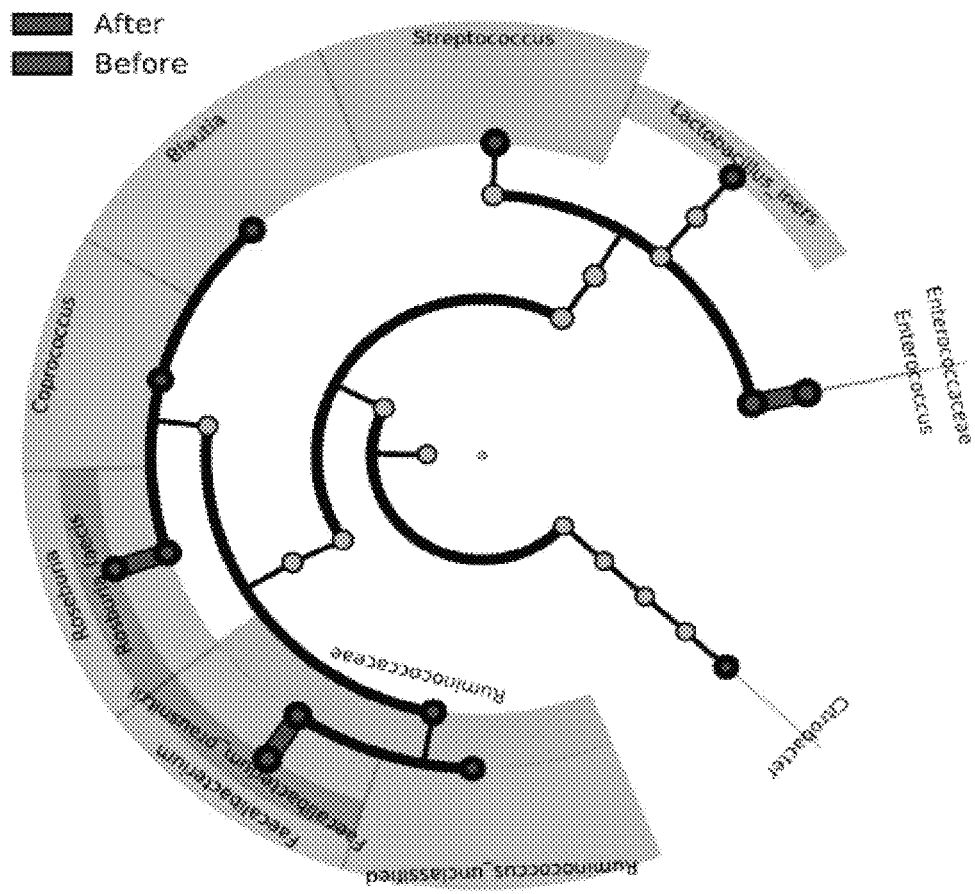
Figure 1C:
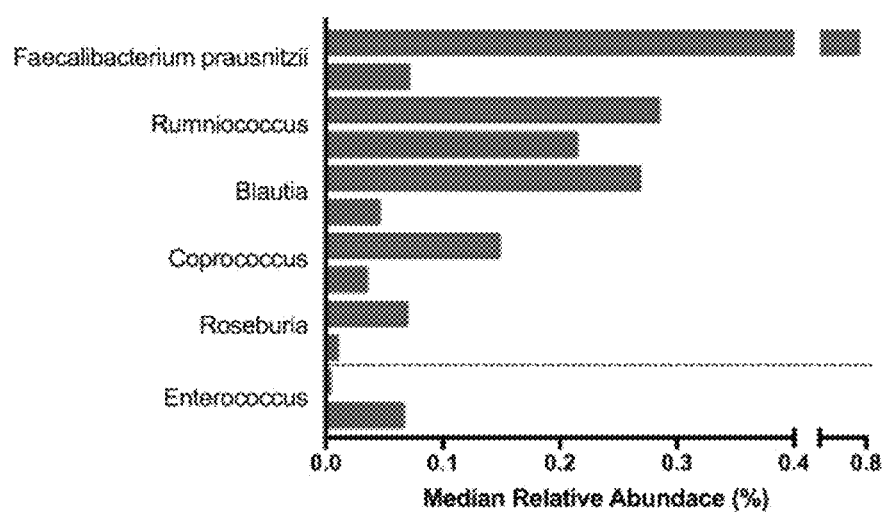

Over 72 hours, there was a modest within-individual decline in fecal microbial diversity that was not statistically significant (Shannon index, median change −3.5%, p=0.06) and a significant decline in fecal microbial richness (operational taxonomic units, median change −7.1%, p<0.01). There were no major phylum-level shifts. LEfSe was used to assess for within-individual changes in specific bacterial taxa over these initial 72 hours. There was a significant decline in the Clostridial Clusters IV (*Faecalibacterium prausnitzii*) and XIVa (*Blautia, Coprococcus, Roseburia*, and *Ruminococcus*) with an expansion in *Enterococcus* (FIGS. 1A-1C; complete LDA results in Table 5). Among these taxa, the greatest decline was seen in *F. prausnitzii* which had an 8-fold median decline over 72 hours (FIG. 1C).

Altered Cluster IV/XIVa Clostridia

Figure 2A:
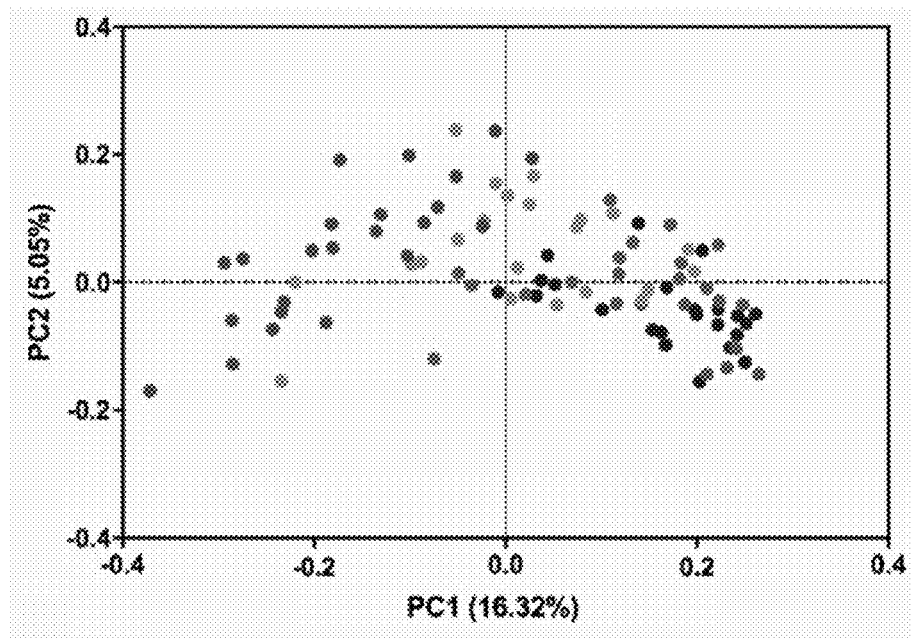
FIGS. 2A-2B. Principal coordinates analysis (PCoA) of subjects at time of ICU admission (a) and 72 hours later (b), stratified by relative abundance of Clostridial Clusters IV and XIVa. There was distinct clustering of subjects based on levels of Clostridial Clusters IV and XIVa both at ICU admission and 72 hours later even though these Clostridia made up <1% overall relative abundance of the fecal microbiome. Taxa included in Cluster IV/XIVa: *F. prausnitzii*, Blautia, *Coprococcus, Roseburia*, and Ruminococcus. Subjects are color-coded by pooled levels of Cluster IV/XIVa Clostridia, from the lowest relative abundance (Quartile 1) to the highest relative abundance (Quartile 4).
Figure 2B:
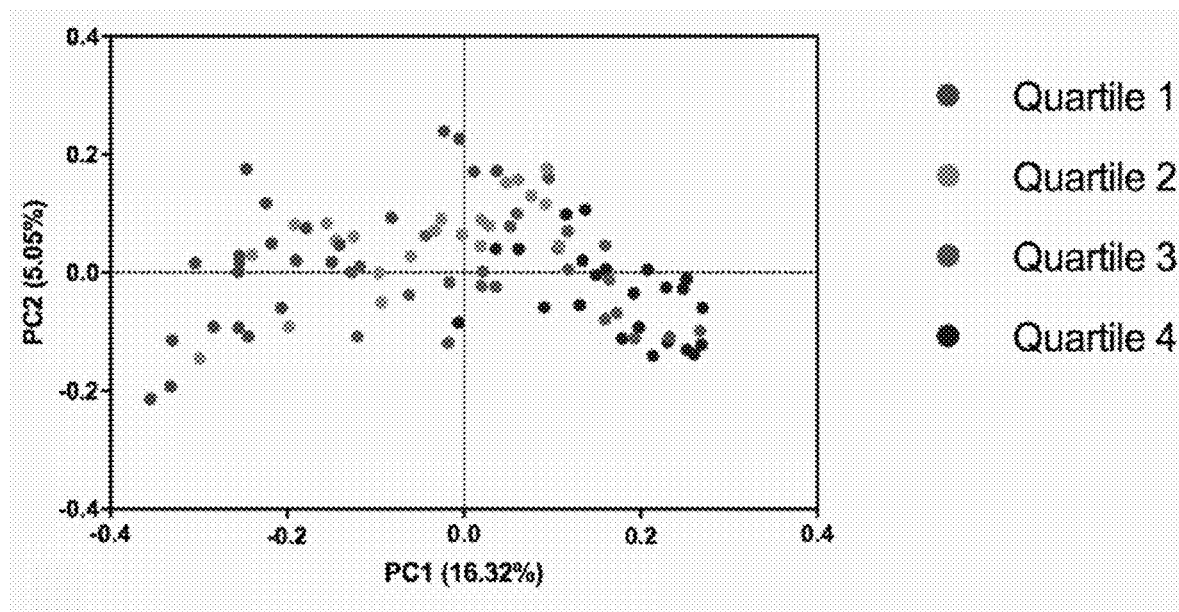
Figure 3A:
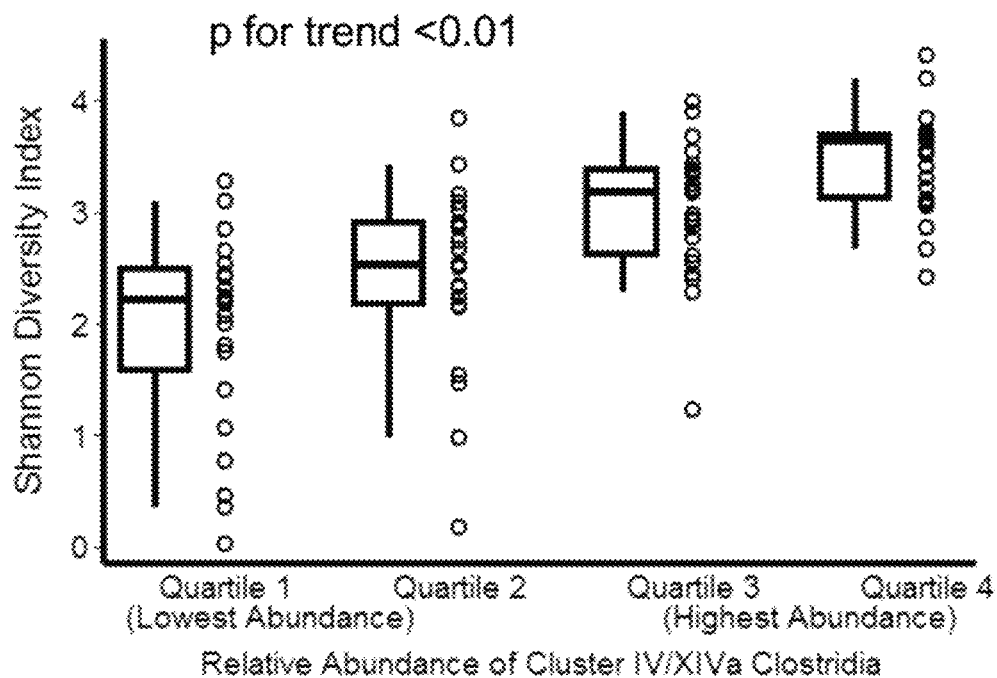
FIGS. 3A-3B. Relationship between Clostridial Clusters IV and XIVa and gut microbiome diversity and stability. Lower levels of Clostridial Clusters IV and XIVa at 72 hours were associated with decreased fecal biodiversity at 72 hours (a) and with decreased community stability over time (b). To test for a relationship between Cluster IV/XIVa Clostridia and fecal biodiversity, Shannon index was calculated for each sample and compared across levels of these taxa. To test for a relationship between Cluster IV/XIVa Clostridia and community stability, beta diversity was calculated for each subject comparing ICU admission to 72 hours later and compared across levels of these Clusters.
Figure 3B:
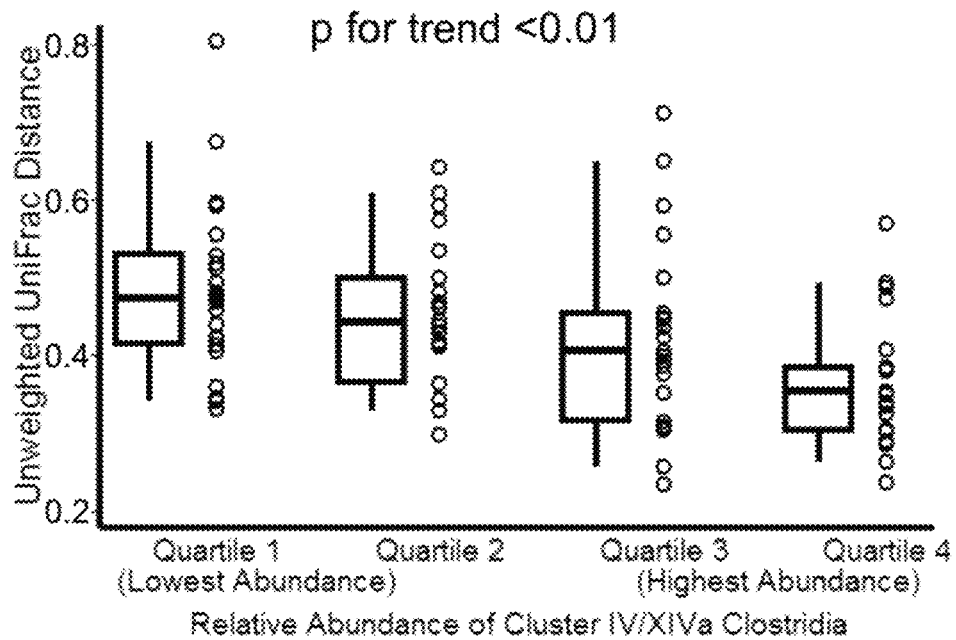

To understand the role of taxa found to be significantly altered in the ICU, the Cluster IV/XIVa Clostridia identified by LEfSe were pooled and organized into quartiles based on relative abundance. Median relative abundance was 2.6% at ICU admission versus 0.30% 72 hours later (sign-rank p=0.01). On PCoA, there was distinct clustering of subjects based on levels of Cluster IV/XIVa Clostridia both at the time of ICU admission (FIG. 2A) and 72 hours later (FIG. 2B). Seventy-two hours after admission, lower levels of Cluster IV/XIVa Clostridia were associated with decreased diversity (FIG. 3A). Additionally, low levels of Cluster IV/XIVa Clostridia at 72 hours were associated with decreased within-individual community stability between ICU admission and 72 hours later as measured by unweighted UniFrac distance (FIG. 3B).

Relationship Between *Enterococcus* and Cluster IV/XIVa Clostridia

Figures 4, 5:
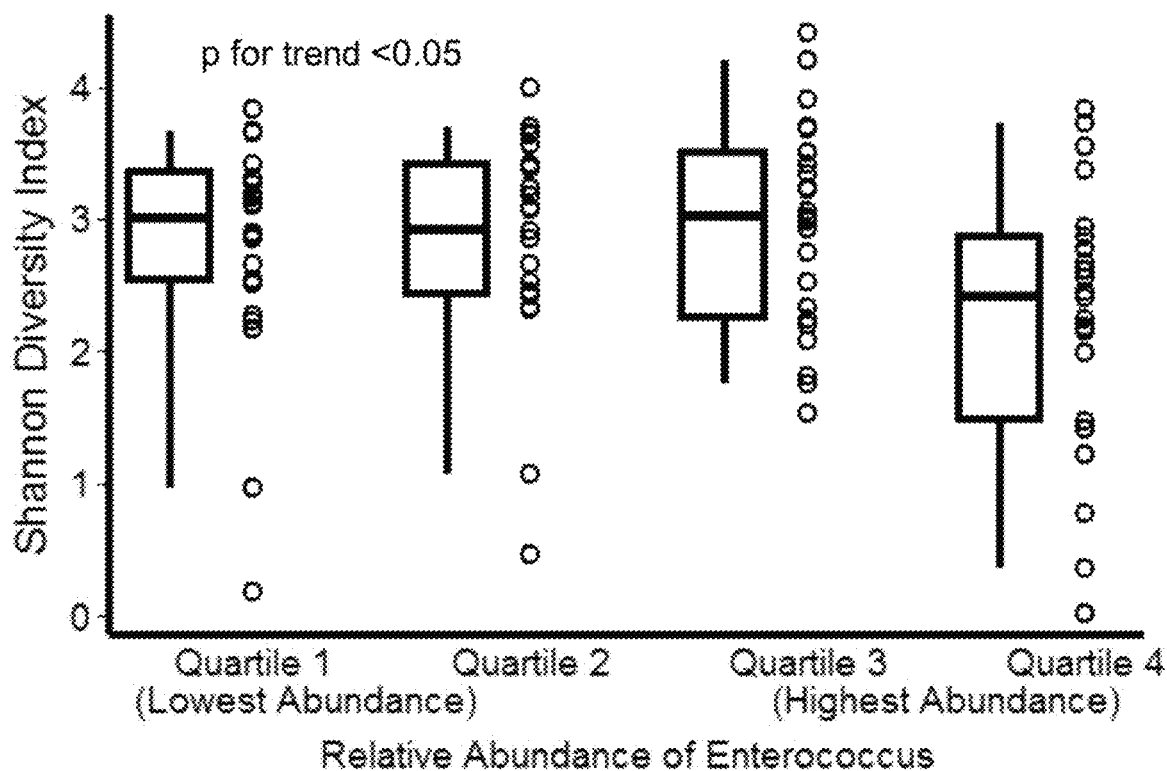
FIG. 4. Fecal microbial diversity and *Enterococcus* after 72 hours in the intensive care unit (ICU). Higher levels of *Enterococcus* were associated with decreased fecal biodiversity (Shannon Index).
FIG. 5. ICU patients exposed to broad-spectrum antibiotics have large gains in antibiotic resistance. Resistome heatmap after 72 hours in the ICU for two subjects who did not receive antibiotics (left) and one subject who received multiple antibiotics (right). Gains in resistance within antibiotic classes shown in reads per kb per million reads.

*Enterococcus*, which was found to be significantly increased on LEfSe analysis (FIG. 1A-1C), was organized into quartiles. Median relative abundance of *Enterococcus* was 0.0038% at ICU admission and 0.067% 72 hours later (sign-rank p<0.01). Higher levels of *Enterococcus* at 72 hours were associated with decreased diversity (FIG. 4). There was evidence of a reciprocal relationship where high levels of *Enterococcus* were only observed with low levels of Cluster IV/XIVa Clostridia and PCoA showed distinct clusters based on high levels of Cluster IV/XIVa Clostridia or high levels of *Enterococcus*, without overlap between clusters. 16S sequencing results do not distinguish between vancomycin-sensitive versus vancomycin-resistant *Enterococcus* (VRE), so VRE culture was performed to assess the potential clinical importance of *Enterococcus* from 16S sequencing data. The relative abundance of *Enterococcus* based on 16S sequencing was highly associated with VRE culture positivity (p<0.01). At 72 hours after ICU admission, rates of VRE on culture were 22% for subjects who received vancomycin versus 7% for subjects who did not (Fisher's p=0.11).

Multivariable Models

Ordinal logistic regression was used to model the relationship between clinical characteristics and taxa found to be altered on LEfSe. Receipt of antibiotics and anemia were significantly associated with decreased Cluster IV/XIVa Clostridia (Table 2). Assessing for dynamic changes, the development of new fever was also associated with decreased Cluster IV/XIVa Clostridia after 72 hours and was included in the final model. When diversity (Shannon index) was added to the final model as a linear variable, the relationship between receipt of antibiotics and Cluster IV/XIVa Clostridia lost significance (OR 2.15, 95% CI 0.77-6.04). When patients with documented gastrointestinal bleeding were excluded, there was no change in the relationship between anemia and levels of Cluster IV/XIVa Clostridia (OR 3.93, 95% CI 1.37-11.3). None of the model estimates were altered by adjusting for acute severity of illness. Clinical characteristics were examined in relationship to the relative abundance of *Enterococcus* after 72 hours and only receipt of antibiotics was significantly associated with increased *Enterococcus* (Table 3).

Discussion

In this prospective cohort study, initial treatment in the ICU was accompanied by a rapid loss of short chain fatty acid (SCFA)-producing bacteria within Clostridial Clusters IV (*Faecalibacterium prausnitzii*) and XIVa (Blautia, Coprococcus, Roseburia, and Ruminococcus) [22]. Loss of these SCFA-producing Clostridia was associated with low overall bacterial biodiversity, with evidence of community instability and an expansion in *Enterococcus* (including VRE). These data suggest that loss of Cluster IV/XIVa Clostridia in the ICU is associated with deleterious changes within the structure of the fecal microbiome and that these bacteria merit further study as potentially protective in the critical care setting.

SCFA-producing Clostridial Clusters were identified based on an untargeted analysis demonstrating within-individual loss of these taxa with a concurrent rise in *Enterococcus* (including VRE). Recent data support the idea that SCFA producers are important in colonization resistance against VRE. SCFAs moderate colonic inflammation [23], enlarge the pool of regulatory T cells [24], and contribute to the thickness of the colonic mucus layer [25]. Specifically, butyrate producing bacteria may restrict the outgrowth of potential pathogens through intracellular butyrate sensor peroxisome proliferator activated receptor γ (PPAR-γ) and by limiting luminal oxygen [26]. Caballero et al. found that Cluster XIVa Clostridia (*Blautia producta* and *Clostridium bolteae*) prevented VRE colonization in antibiotic-treated mice; inhibition of VRE colonization appeared to be the result of a direct interaction between *B. producta* and VRE [27]. The same investigative team has analyzed gut microbiome-related risk factors in patients undergoing bone marrow transplant (BMT). Like ICU patients, BMT patients are likely to receive broad-spectrum antibiotics and to be immunosuppressed. In these patients, low fecal microbial diversity at the time of BMT predicted VRE bacteremia and mortality [7, 8, 28]. In the ICU, prolonged stays have been associated with a progressive loss of Clostridia with replacement by *Enterococcus* [6] and low fecal SCFA levels have been correlated with domination by *Enterococcus* and with worse clinical outcomes [13, 29]. Our study highlights the potential importance of SCFA producers in preventing VRE colonization in an ICU-based population.

While our data emphasizes SCFA-producing Clostridia for colonization resistance against VRE, we also found inverse relationships between Cluster IV/XIVa Clostridia and other potential pathogens including *Staphylococcus* and Enterobacteriaceae (data not shown). Prior studies support the hypothesis that SCFA producers have a role in gut microbiome homeostasis that extends beyond colonization resistance against VRE [30]. SCFAs are produced from dietary fiber and have been linked to decreased colonic inflammation [23], an enlarged pool of regulatory T cells [24], and beneficial effects on energy metabolism [31]. In an animal model, fiber deprivation led to thinning of the colonic mucus layer and increased pathogen susceptibility [25]. In BMT patients, taxa within Cluster IV/XIVa Clostridia were associated with decreased risk for *Clostridium difficile* infection [32]. In ICU patients sampled within 48 hours of admission and at ICU discharge, loss of *Faecalibacterium* was associated with loss of diversity and outgrowth of Enterobacteriaceae [14, 33]. In our data, Cluster IV/XIVa Clostridia comprised a small proportion of the total gut microbiome by abundance yet explained a large degree of inter-individual variability on clustering analyses and were highly correlated with diversity and community stability, typical markers for a healthy gut microbiome across populations [34, 35]. These findings imply that these bacteria may serve a critical functional role in the distal gut. Yet fiber, the primary fuel substrate for the Clostridia identified here, is often missing from enteral feeds commonly used in the ICU [36].

In this data, receipt of antibiotics was associated with low levels of Cluster IV/XIVa Clostridia and with high levels of *Enterococcus*. The relationship between receipt of antibiotics and Cluster IV/XIVa Clostridia was attenuated by adjusting for Shannon diversity, implying that the effect of antibiotics on these taxa may be mediated by overall structural effects of antibiotics on the microbiota [37]. Subjects who received antibiotics had increased levels of *Enterococcus* on sequencing, and subjects who received vancomycin had a 15% absolute increase in rates of VRE colonization based on culture. Approximately 75% of ICU patients receive antibiotics for known or suspected infections [38, 39] and, because initially inappropriate antibiotics predict mortality in sepsis [40], broad-spectrum antibiotics are often given before the results of cultures or other testing become available. Our data support the idea that antibiotics induce broad structural changes within the gut microbiome and is consistent with the observation that antibiotics promote colonization with antibiotic-resistant bacteria [41].

The presence of anemia and the new development of fever were also associated with low levels of Cluster IV/XIVa Clostridia 72 hours after ICU admission. Anemia may signify gastrointestinal bleeding, and the iron contained in whole blood may alter gastrointestinal bacteria to impact levels of these bacteria [42]. Exclusion of patients with overt gastrointestinal bleeding did not change the relationship between anemia and Cluster IV/XIVa Clostridia, but a large proportion of patients may have had subclinical bleeding that contributed to anemia. New fevers may reflect represent ICU-acquired infections that either cause, or result from, low levels of Cluster IV/XIVa Clostridia. Neither the estimate for anemia nor the estimate for fever was influenced by the inclusion of acute severity of illness in the final model.

There is substantial interest in testing prebiotics or probiotics to prevent infections in the ICU. In murine models, defined mixtures of bacteria including bacteria within the Clostridial Clusters IV and XIVa provided colonization resistance to VRE after antibiotic challenge [43] and promoted VRE intestinal clearance [27]. In germ-free adult or neonatal mice, a consortium of Clostridia including Clusters IV and XIVa conferred colonization resistance to the enteric pathogens *S. Typhimurium* and *C. rodentium* [44]. In a murine sepsis model, there was a survival benefit with fiber supplementation, mediated in part by a rise in Cluster XIVa Clostridia [45]. To date, clinical trials testing probiotics have delivered heterogeneous organisms (e.g., *Lactobacillus* or *Bifidobacterium* sp.) and have had mixed results or in some cases have been associated with harm [46-48]. Future studies may wish to address whether SCFA-producing Clostridia, or related prebiotics, can be successfully delivered and retained within the colonic microbiome.

Our study has several strengths. There was a rigorous protocol for sample collection, with subjects sampled immediately at the time of ICU admission and again 72 hours later. This serial sampling permitted evaluation for dynamic within-individual changes over the initial ICU treatment period. A broad swath of clinical data was ascertained both at ICU admission and 72 hours later, which allowed us to assess relationships after adjusting for underlying patient factors. Standard bacterial culture for VRE was used to confirm sequencing results related to *Enterococcus*, the main pathogen showing outgrowth in these subjects.

Conclusions

In sum, we found that Clostridia within the Clusters IV and XIVa were rapidly lost during the initial treatment period in the ICU. Low levels of Cluster IV/XIVa Clostridia were associated with receipt of antibiotics, but no other potentially modifiable ICU interventions. Low levels of Cluster IV/XIVa Clostridia were also associated with low fecal microbial diversity, microbiome community instability, and the outgrowth of vancomycin-resistant *Enterococcus*. Short chain fatty acid-producing Clostridia may serve a key role in the maintenance of normal gastrointestinal colonization resistance in the ICU.

TABLE 1

Demographics and ICU interventions during the 72 hours following admission to the ICU.

| Demographics | N, % |
| --- | --- |
| Sex | |
| Male | 49 (53%) |
| Female | 44 (47%) |
| Age | |
| <60 years old | 32 (34%) |
| 60-68 | 30 (32%) |
| >68 years old | 31 (33%) |
| Admission type | |
| Medical | 40 (43%) |
| Surgical | 53 (57%) |
| ICU Interventions | N, % |
| Antibiotics | 72 (77%) |
| PPIs | 47 (44%) |
| Mechanical ventilation | |
| Some but <72 hrs | 23 (25%) |
| ≥72 hours | 17 (18%) |

TABLE 1-continued

Demographics and ICU interventions during the 72 hours following admission to the ICU.

| | |
| --- | --- |
| Hemodialysis | 6 (6%) |
| Enteral feeding | 74 (80%) |

ICU: intensive care unit;

PPIs: proton pump inhibitors.

TABLE 2

Relationship between clinical variables and decreased Clostridial Clusters IV and XIVa after 72 hours in the ICU.

| Variable | Unadjusted OR (95% CI)* | Multivariable OR (95% CI)* |
| --- | --- | --- |
| Demographics | | |
| Female sex | 1.17 (0.57-2.43) | — |
| Age | | |
| <60 years old | Ref | Ref |
| 60-68 years old | 0.60 (0.24-1.46) | — |
| >68 years old | 0.82 (0.33-2.04) | — |
| Surgical admission** | 1.29 (0.62-2.72) | — |
| Clinical characteristics after 72 hours | | |
| Fever (temp > 38° C.) | | |
| Newly developing | 2.84 (0.60-13.6) | 5.07 (1.02-25.2) |
| After 72 hours | 2.61 (0.65-10.5) | — |
| Hematocrit < 33.8% | 5.36 (2.11-13.6) | 5.08 (1.77-14.6) |
| WBC ≥ 12,000 × $10^9$/L | 0.96 (0.46-2.01) | — |
| Albumin < 3.5 g/dL | 2.18 (1.00-4.76) | 1.07 (0.44-2.60) |
| APACHE IV score | 1.00 (0.99-1.02) | — |
| Treatment-related characteristics over 72 hours | | |
| Antibiotics (any) | 3.86 (1.47-10.1) | 2.90 (1.06-7.91) |
| PPIs (any) | 1.92 (0.91-4.02) | — |
| Ventilation ≥ 72 Hours | 1.28 (0.51-3.26) | — |
| Hemodialysis | 1.53 (0.41-5.76) | — |
| Enteral feeding | 0.89 (0.37-2.15) | — |

ICU: intensive care unit;
OR: odds ratio;
CI: confidence interval;
WBC: white blood cell count;
APACHE: acute physiology and chronic health evaluation. Shown are patient characteristics that significantly changed during the 72 hours after ICU admission and all treatment-related variables.
Boldfaced variables were significant at p < 0.05 in the final model.
*Ordinal logistic regression:
ORs represent odds of moving from a higher into a lower quartile of relative abundance of Clostridial Clusters IV and XIVa.
**Comparator: medical admission.

TABLE 3

Relationship between clinical variables and increased Enterococcus after 72 hours in the ICU.

| Variable | Unadjusted OR (95% CI) | Multivariable OR (95% CI) |
| --- | --- | --- |
| Demographics | | |
| Female sex | 1.05 (0.51-2.18) | — |
| Age | | |
| <60 years old | Ref | Ref |
| 60-68 years old | 0.78 (0.32-1.88) | — |
| >68 years old | 0.88 (0.36-2.16) | — |
| Surgical admission** | 0.50 (0.23-1.06) | — |

TABLE 3-continued

Relationship between clinical variables and increased Enterococcus after 72 hours in the ICU.

| Variable | Unadjusted OR (95% CI) | Multivariable OR (95% CI) |
|---|---|---|
| Clinical characteristics after 72 hours | | |
| Fever (temp > 38° C.) | | |
| Newly developing | 0.48 (0.12-1.98) | — |
| After 72 hours | 0.51 (0.10-2.54) | — |
| Hematocrit < 33.8% | 1.65 (0.72-3.81) | — |
| WBC ≥ 12,000 × 10$^9$/L | 1.30 (0.61-2.75) | — |
| Albumin < 3.5 g/dL | 1.24 (0.59-2.61) | — |
| APACHE IV score | 1.02 (1.00-1.03) | 1.00 (0.98-1.02) |
| Treatment-related characteristics over 72 hours | | |
| Antibiotics (any) | 3.19 (1.33-7.67) | 2.66 (1.08-6.57) |
| PPIs (any) | 0.69 (0.33-1.44) | — |
| Ventilation ≥ 72 Hours | 3.51 (1.26-9.79) | 1.49 (0.32-6.94) |
| Hemodialysis | 1.03 (0.21-4.99) | — |
| Enteral feeding | 0.31 (0.12-0.79) | 0.40 (0.15-1.11) |

ICU: intensive care unit;
OR: odds ratio;
CI: confidence interval;
WBC: white blood cell count;
APACHE: acute physiology and chronic health evaluation. Shown are patient characteristics that significantly changed during the 72 hours after ICU admission and all treatment-related variables. Boldfaced variables were significant at p < 0.05 in the final model.
*Ordinal logistic regression: ORs represent odds of moving from a higher into a lower quartile of relative abundance of Enterococcus.
**Comparator: medical admission.

TABLE 4

Patient characteristics at the time of admission to the intensive care unit and 72 hours later.

| Characteristics | ICU Admission (n, %) | After 72 Hours (n, %) | P-value for Change |
|---|---|---|---|
| Clinical characteristics | | | |
| Fever (temp > 38° C.) | | | |
| Yes | 17 (18%) | 6 (7%) | 0.02 |
| No | 76 (82%) | 87 (94%) | |
| Tachycardia (HR > 90 bpm) | | | |
| Yes | 37 (40%) | 33 (36%) | 0.48 |
| No | 56 (60%) | 60 (65%) | |
| Oliguria (UOP < 800 cc/24 h) | | | |
| Yes | 14 (15%) | 13 (14%) | 0.82 |
| No | 79 (85%) | 80 (86%) | |
| Laboratory values | | | |
| Hematocrit | | | |
| <33.8% | 49 (53%) | 69 (74%) | <0.01 |
| ≥33.8% | 44 (47%) | 24 (26%) | |
| White blood cell count | | | |
| ≥ 12,000 cells × 10$^9$/L | 42 (45%) | 34 (37%) | 0.10 |
| < 12,000 cells × 10$^9$/L | 51 (55%) | 59 (63%) | |
| Creatinine | | | |
| >1.3 mg/dL | 23 (25%) | 28 (30%) | 0.13 |
| ≤1.3 mg/dL | 70 (75%) | 65 (70%) | |
| Sodium | | | |
| >145 or <137 mEq/L | 25 (27%) | 34 (37%) | 0.11 |
| 137-145 mEq/L | 68 (73%) | 59 (63%) | |
| Total bilirubin | | | |
| >1.3 mg/dL | 19 (20%) | 19 (20%) | 1.00 |
| ≤1.3 mg/dL | 74 (80%) | 74 (80%) | |
| Albumin | | | |
| <3.5 g/dL | 43 (46%) | 58 (62%) | <0.01 |
| 3.5 g/dL | 50 (54%) | 35 (38%) | |
| APACHE IV* score | 54 (38-88) | 42 (33-59) | <0.01 |

*Calculated without age.

TABLE 5

LDA scores and p-values for discriminative taxa identified using LEfSe.

| Discriminative taxa | Group Enriched | Log2-Fold Change (Median) | LDA score | P-value |
|---|---|---|---|---|
| Bacteria.Firmicutes.Bacilli.Lactobacillales.Enterococcaceae.Enterococcus | After 72 hours | +2.2 | 3.522 | 0.000 |
| Bacteria.Firmicutes.Bacilli.Lactobacillales.Streptococcaceae.Streptococcus | After 72 hours | +.89 | 2.959 | 0.048 |
| Bacteria.Firmicutes.Clostridia.Clostridiales.Lachnospiraceae.Roseburia | At ICU admission | −1.6 | 2.632 | 0.015 |
| Bacteria.Firmicutes.Clostridia.Clostridiales.Ruminococcaceae.Faecalibacterium.prausnitzii | At ICU admission | −1.2 | 2.743 | 0.035 |
| Bacteria.Firmicutes.Clostridia.Clostridiales.Ruminococcaceae | At ICU admission | −1.8 | 2.204 | 0.040 |
| Bacteria.Proteobacteria.Gammaproteobacteria.Enterobacteriales.Enterobacteriaceae.Citrobacter | After 72 hours | +2.2 | 2.178 | 0.037 |
| Bacteria.Firmicutes.Clostridia.Clostridiales.Lachnospiraceae.Blautia | At ICU admission | −1.2 | 2.143 | 0.031 |
| Bacteria.Firmicutes.Clostridia.Clostridiales.Lachnospiraceae.Coprococcus | At ICU admission | −.65 | 2.047 | 0.013 |

Taxa have been ordered by LDA score from highest to lowest.
LDA: least discriminant analysis;
LEfSe: LDA effect size algorithm.

REFERENCES

1. Dickson R P: The microbiome and critical illness. *Lancet Respir Med* 2016, 4:59-72.
2. Klingensmith N J, Coopersmith C M: The Gut as the Motor of Multiple Organ Dysfunction in Critical Illness. *Crit Care Clin* 2016, 32:203-212.
3. Krezalek M A, DeFazio J, Zaborina O, Zaborin A, Alverdy J C: The Shift of an Intestinal "Microbiome" to a "Pathobiome" Governs the Course and Outcome of Sepsis Following Surgical Injury. *Shock* 2016, 45:475-482.
4. Johanson W G, Pierce A K, Sanford J P: Changing pharyngeal bacterial flora of hospitalized patients. Emergence of gram-negative bacilli. *N Engl J Med* 1969, 281:1137-1140.
5. Yeh A, Rogers M B, Firek B, Neal M D, Zuckerbraun B S, Morowitz M J: Dysbiosis Across Multiple Body Sites in Critically Ill Adult Surgical Patients. *Shock* 2016, 46:649-654.
6. Zaborin A, Smith D, Garfield K, Quensen J, Shakhsheer B, Kade M, Tirrell M, Tiedje J, Gilbert J A, Zaborina O, Alverdy J C: Membership and behavior of ultra-low-diversity pathogen communities present in the gut of humans during prolonged critical illness. *MBio* 2014, 5:e01361-01314.
7. Taur Y, Xavier J B, Lipuma L, Ubeda C, Goldberg J, Gobourne A, Lee Y J, Dubin K A, Socci N D, Viale A, et al: Intestinal domination and the risk of bacteremia in patients undergoing allogeneic hematopoietic stem cell transplantation. *Clin Infect Dis* 2012, 55:905-914.
8. Ubeda C, Taur Y, Jenq R R, Equinda M J, Son T, Samstein M, Viale A, Socci N D, van den Brink M R, Kamboj M, Pamer E G: Vancomycin-resistant *Enterococcus* domination of intestinal microbiota is enabled by antibiotic treatment in mice and precedes bloodstream invasion in humans. *J Clin Invest* 2010, 120:4332-4341.
9. Bohnhoff M, Drake B L, Miller C P: Effect of streptomycin on susceptibility of intestinal tract to experimental *Salmonella* infection. *Proc Soc Exp Biol Med* 1954, 86:132-137.
10. Miller C P, Bohnhoff M, Drake B L: The effect of antibiotic therapy on susceptibility to an experimental enteric infection. *Trans Assoc Am Physicians* 1954, 67:156-161.
11. Barthel M, Hapfelmeier S, Quintanilla-Martinez L, Kremer M, Rohde M, Hogardt M, Pfeffer K, Russmann H, Hardt W D: Pretreatment of mice with streptomycin provides a *Salmonella enterica* serovar *Typhimurium* colitis model that allows analysis of both pathogen and host. *Infect Immun* 2003, 71:2839-2858.
12. Lopetuso L R, Scaldaferri F, Petito V, Gasbarrini A: Commensal Clostridia: leading players in the maintenance of gut homeostasis. *Gut Pathog* 2013, 5:23.
13. Shimizu K, Ogura H, Hamasaki T, Goto M, Tasaki O, Asahara T, Nomoto K, Morotomi M, Matsushima A, Kuwagata Y, Sugimoto H: Altered gut flora are associated with septic complications and death in critically ill patients with systemic inflammatory response syndrome. *Dig Dis Sci* 2011, 56:1171-1177.
14. McDonald D, Ackermann G, Khailova L, Baird 458 C, Heyland D, Kozar R, Lemieux M, Derenski K, King J, Vis-Kampen C, et al: Extreme Dysbiosis of the Microbiome in Critical Illness. *mSphere* 2016, 1.
15. Hayakawa M, Asahara T, Henzan N, Murakami H, Yamamoto H, Mukai N, Minami Y, Sugano M, Kubota N, Uegaki S, et al: Dramatic changes of the gut flora immediately after severe and sudden insults. *Dig Dis Sci* 2011, 56:2361-2365.
16. Budding A E, Grasman M E, Eck A, Bogaards J A, Vandenbroucke-Grauls C M, van Bodegraven A A, Savelkoul P H: Rectal swabs for analysis of the intestinal microbiota. *PLoS One* 2014, 9:e101344.
17. Teasdale G, Jennett B: Assessment of coma and impaired consciousness. A practical scale. *Lancet* 1974, 2:81-84.
18. Zimmerman J E, Kramer A A, McNair D S, Malila F M: Acute Physiology and Chronic Health Evaluation (APACHE) IV: hospital mortality assessment for today's critically ill patients. *Crit Care Med* 2006, 34:1297-1310.
19. Kuczynski J, Lauber C L, Walters W A, Parfrey L W, Clemente J C, Gevers D, Knight R: Experimental and analytical tools for studying the human microbiome. *Nat Rev Genet* 2011, 13:47-58.
20. Caporaso J G, Kuczynski J, Stombaugh J, Bittinger K, Bushman F D, Costello E K, Fierer N, Pena A G, Goodrich J K, Gordon J I, et al: QIIME allows analysis of high-throughput community sequencing data. *Nat Methods* 2010, 7:335-336.
21. Segata N, Izard J, Waldron L, Gevers D, Miropolsky L, Garrett W S, Huttenhower C: Metagenomic biomarker discovery and explanation. *Genome Biol* 2011, 12:R60.
22. Collins M D, Lawson P A, Willems A, Cordoba J J, Fernandez-Garayzabal J, Garcia P, Cai J, Hippe H, Farrow J A: The phylogeny of the genus *Clostridium*: proposal of five new genera and eleven new species combinations. *Int J Syst Bacteriol* 1994, 44:812-826.
23. O'Keefe S J, Li J V, Lahti L, Ou J, Carbonero F, Mohammed K, Posma J M, Kinross J, Wahl E, Ruder E, et al: Fat, fibre and cancer risk in African Americans and rural Africans. *Nat Commun* 2015, 6:6342.
24. Atarashi K, Tanoue T, Oshima K, Suda W, Nagano Y, Nishikawa H, Fukuda S, Saito T, Narushima S, Hase K, et al: Treg induction by a rationally selected mixture of Clostridia strains from the human microbiota. *Nature* 2013, 500:232-236.
25. Desai M S, Seekatz A M, Koropatkin N M, Kamada N, Hickey C A, Wolter M, Pudlo N A, Kitamoto S, Terrapon N, Muller A, et al: A Dietary Fiber-Deprived Gut Microbiota Degrades the Colonic Mucus Barrier and Enhances Pathogen Susceptibility. *Cell* 2016, 167:1339-1353 e1321.
26. Byndloss M X, Olsan E E, Rivera-Chavez F, Tiffany C R, Cevallos S A, Lokken K L, Torres T P, Byndloss A J, Faber F, Gao Y, et al: Microbiota-activated PPAR gamma signaling inhibits dysbiotic Enterobacteriaceae expansion. *Science* 2017, 357:570-575.
27. Caballero S, Kim S, Carter R A, Leiner I M, Susac B, Miller L, Kim G J, Ling L, Pamer E G: Cooperating Commensals Restore Colonization Resistance to Vancomycin-Resistant *Enterococcus* 503 *faecium*. *Cell Host Microbe* 2017, 21:592-602 e594.
28. Taur Y, Jenq R R, Perales M A, Littmann E R, Morjaria S, Ling L, No D, Gobourne A, Viale A, Dahi P B, et al: The effects of intestinal tract bacterial diversity on mortality following allogeneic hematopoietic stem cell transplantation. *Blood* 2014, 124:1174-1182.
29. Yamada T, Shimizu K, Ogura H, Asahara T, Nomoto K, Yamakawa K, Hamasaki T, Nakahori Y, Ohnishi M, Kuwagata Y, Shimazu T: Rapid and Sustained Long-Term Decrease of Fecal Short-Chain Fatty Acids in Critically Ill Patients With Systemic Inflammatory Response Syndrome. *JPEN J Parenter Enteral Nutr* 2015, 39:569-577.

30. Sonnenburg E D, Sonnenburg J L: Starving our microbial self: the deleterious consequences of a diet deficient in microbiota-accessible carbohydrates. *Cell Metab* 2014, 20:779-786.
31. De Vadder F, Kovatcheva-Datchary P, Goncalves D, Vinera J, Zitoun C, Duchampt A, Backhed F, Mithieux G: Microbiota-generated metabolites promote metabolic benefits via gut-brain neural circuits. *Cell* 2014, 156:84-96.
32. Lee Y J, Arguello E S, Jenq R R, Littmann E, Kim G J, Miller L C, Ling L, Figueroa C, Robilotti E, Perales M A, et al: Protective Factors in the Intestinal Microbiome Against *Clostridium difficile* Infection in Recipients of Allogeneic Hematopoietic Stem Cell Transplantation. *J Infect Dis* 2017, 215:1117-1123.
33. Wischmeyer P E, McDonald D, Knight R: Role of the microbiome, probiotics, and 'dysbiosis therapy' in critical illness. *Curr Opin Crit Care* 2016, 22:347-353.
34. Falony G, Joossens M, Vieira-Silva S, Wang J, Darzi Y, Faust K, Kurilshikov A, Bonder M J, Valles-Colomer M, Vandeputte D, et al: Population-level analysis of gut microbiome variation. *Science* 2016, 352:560-564.
35. Zhernakova A, Kurilshikov A, Bonder M J, Tigchelaar E F, Schirmer M, Vatanen T, Mujagic Z, Vila A V, Falony G, Vieira-Silva S, et al: Population-based metagenomics analysis reveals markers for gut microbiome composition and diversity. *Science* 2016, 352:565-569.
36. O'Keefe S J, Ou J, Delany J P, Curry S, Zoetendal E, Gaskins H R, Gunn S: Effect of fiber supplementation on the microbiota in critically ill patients. *World J Gastrointest Pathophysiol* 2011, 2:138-145.
37. Blaser M J: Antibiotic use and its consequences for the normal microbiome. *Science* 2016, 352:544-545.
38. Vincent J L, Rello J, Marshall J, Silva E, Anzueto A, Martin C D, Moreno R, Lipman J, Gomersall C, Sakr Y, et al: International study of the prevalence and outcomes of infection in intensive care units. *JAMA* 2009, 302:2323-2329.
39. Angus D C, Linde-Zwirble W T, Lidicker J, Clermont G, Carcillo J, Pinsky M R: Epidemiology of severe sepsis in the United States: analysis of incidence, outcome, and associated costs of care. *Crit Care Med* 2001, 29:1303-1310.
40. Zilberberg M D, Shorr A F, Micek S T, Vazquez-Guillamet C, Kollef M H: Multi-drug resistance, inappropriate initial antibiotic therapy and mortality in Gram negative severe sepsis and septic shock: a retrospective cohort study. *Crit Care* 2014, 18:596.
41. Filius P M, Gyssens I C, Kershof I M, Roovers P J, Ott A, Vulto A G, Verbrugh H A, Endtz H P: Colonization and resistance dynamics of gram-negative bacteria in patients during and after hospitalization. *Antimicrob Agents Chemother* 2005, 49:2879-2886.
42. Jaeggi T, Kortman G A, Moretti D, Chassard C, Holding P, Dostal A, Boekhorst J, Timmerman H M, Swinkels D W, Tjalsma H, et al: Iron fortification adversely affects the gut microbiome, increases pathogen abundance and induces intestinal inflammation in Kenyan infants. *Gut* 2015, 64:731-742.
43. Ubeda C, Bucci V, Caballero S, Djukovic A, Toussaint N C, Equinda M, Lipuma L, Ling L, Gobourne A, No D, et al: Intestinal microbiota containing Barnesiella species cures vancomycin-resistant *Enterococcus faecium* colonization. *Infect Immun* 2013, 81:965-973.
44. Kim Y G, Sakamoto K, Seo S U, Pickard J M, Gillilland M G, 3rd, Pudlo N A, Hoostal M, Li X, Wang T D, Feehley T, et al: Neonatal acquisition of Clostridia species protects against colonization by bacterial pathogens. *Science* 2017, 356:315-319.
45. Morowitz M J, Di Caro V, Pang D, Cummings J, Firek B, Rogers M B, Ranganathan S, Clark R S B, Aneja R K: Dietary Supplementation With Nonfermentable Fiber Alters the Gut Microbiota and Confers Protection in Murine Models of Sepsis. *Crit Care Med* 2017, 45:e516-e523.
46. Besselink M G, van Santvoort H C, Buskens E, Boermeester M A, van Goor H, Timmerman H M, Nieuwenhuijs V B, Bollen T L, van Ramshorst B, Witteman B J, et al: Probiotic prophylaxis in predicted severe acute pancreatitis: a randomised, double-blind, placebo-controlled trial. *Lancet* 2008, 371:651-659.
47. Knight D J, Gardiner D, Banks A, Snape S E, Weston V C, Bengmark S, Girling K J: Effect of synbiotic therapy on the incidence of ventilator associated pneumonia in critically ill patients: a randomised, double-blind, placebo controlled trial. *Intensive Care Med* 2009, 35:854-861.
48. Petrof E O, Dhaliwal R, Manzanares W, Johnstone J, Cook D, Heyland D K: Probiotics in the critically ill: a systematic review of the randomized trial evidence. *Crit Care Med* 2012, 40:3290-3302.
49. Gorrie C L, Mirceta M, Wick R R, Edwards D J, Thomson N R, Strugnell R A, Pratt N, Garlick J, Watson K, Pilcher D, et al: Gastrointestinal carriage is a major reservoir of *K. pneumoniae* infection in intensive care patients. *Clin Infect Dis* 2017.
50. Levy M M, Macias W L, Vincent J L, Russell J A, Silva E, Trzaskoma B, Williams M D: Early changes in organ function predict eventual survival in severe sepsis. *Crit Care Med* 2005, 33:2194-2201.
51. Rakoff-Nahoum S, Foster K R, Comstock L E: The evolution of cooperation within the gut microbiota. *Nature* 2016, 533:255-259.
52. Schloss P D, Westcott S L, Ryabin T, Hall J R, Hartmann M, Hollister E B, Lesniewski R A, Oakley B B, Parks D H, Robinson C J, Sahl J W, Stres B, Thallinger G G, Van Horn D J, Weber C F. Introducing mothur: open-source, platform-independent, community-supported software for describing and comparing microbial communities. *Appl Environ Microbiol* 2009; 75: 7537-7541.
53. McDonald D, Price M N, Goodrich J, Nawrocki E P, DeSantis T Z, Probst A, Andersen G L, Knight R, Hugenholtz P. An improved Greengenes taxonomy with explicit ranks for ecological and evolutionary analyses of bacteria and archaea. *ISME J* 2012; 6: 610-618.
54. Edgar R C. Search and clustering orders of magnitude faster than BLAST. *Bioinformatics* 2010; 26: 2460-2461.
55. Price M N, Dehal P S, Arkin A P. FastTree 2—approximately maximum-likelihood trees for large alignments. *PLoS One* 2010; 5: e9490.
56. Caporaso J G, Kuczynski J, Stombaugh J, Bittinger K, Bushman F D, Costello E K, Fierer N, Pena A G, Goodrich J K, Gordon J I, Huttley G A, Kelley S T, Knights D, Koenig J E, Ley R E, Lozupone C A, McDonald D, Muegge B D, Pirrung M, Reeder J, Sevinsky J R, Turnbaugh P J, Walters W A, Widmann J, Yatsunenko T, Zaneveld J, Knight R. QIIME allows analysis of high-throughput community sequencing data. *Nat Methods* 2010; 7: 335-336.
57. Lozupone C, Knight R. UniFrac: a new phylogenetic method for comparing microbial communities. *Appl Environ Microbiol* 2005; 71: 8228-8235.

Example 2 Inulin for the Prevention of Antibiotic Resistant Infection or Pathogen Colonization in the Intensive Care Unit Antibiotic resistance represents an emerging healthcare crisis, both in the United States and abroad. Multidrug resistant (MDR) bacterial infections are a leading cause of morbidity, death, and healthcare-associated costs.[1-3] Nowhere is this more important than in the intensive care unit (ICU), where over half of all infections are MDR[4] and where sepsis from MDR bacteria confers 10-20% absolute increased mortality.[5-7]

Antibiotic resistance in the ICU is fundamentally a problem of the human gastrointestinal microbiome. The gut microbiome is the critical reservoir for the bacteria and plasmids that encode antibiotic resistance genes.[17-19] The normal gut microbiota prevents colonization and subsequent infection with MDR organisms through competition for scarce resources and other mechanisms,[20] as demonstrated by the ability of fecal microbiota transplant (FMT) to reduce gastrointestinal carriage of multi-drug resistant organisms (MDROs).[21] The ability of the gut microbiome to prevent the proliferation of pathogens is termed colonization resistance; in the setting of critical illness, normal colonization resistance is lost.[22-25] There are no currently available therapies to prevent loss of gut colonization resistance and subsequent proliferation of MDR organisms.

Specific gut bacteria contribute to colonization resistance against antibiotic resistant pathogens. ICU patients have low levels of butyrate and other short chain fatty acids (SCFAs), which are derived from dietary fiber by specific anaerobic bacteria in the gut. SCFAs moderate colonic inflammation,[26] enlarge the pool of regulatory T cells,[27] and contribute to the thickness of the colonic mucus layer and pathogen resistance.[28] During critical illness, levels of SCFA-producing bacteria and SCFAs are low, and these levels further decline with antibiotic treatment. Loss of SCFA-producing bacteria correlates with an increase in colonization with vancomycin-resistant *Enterococcus* and other antibiotic-resistant pathogens. We hypothesize that preservation of SCFA-producing bacteria during critical illness will prevent the proliferation of antimicrobial resistance and lower the risk of infections with MDR organisms.

Prebiotics are a highly promising and well-tolerated potential therapy to preserve colonization resistance and prevent proliferation of antibiotic resistant pathogens. Competition for nutrients is the strongest driver of microbiome composition.[29] The prebiotic fiber inulin is a non-digestible polysaccharide and a key nutrient source for SCFA-producing bacteria. Inulin improves gut barrier function, confers protection in animal sepsis models, has bifidogenic and butyrogenic effects on the microbiome, and decreases inflammation.[30,31] A randomized trial of inulin in obese women resulted in decreased levels of circulating inflammatory markers as well increased SCFA-producing bacteria in the gut,[32] and multiple studies have shown than inulin is safe and well-tolerated. We hypothesize that inulin supplementation in critically ill patients will result in higher levels of SCFA-producing Clostridia, decreased gastrointestinal antibiotic resistance, and lower risk for MDR infections.

To this end, a Phase 1/2 trial will be conducted to test inulin for the prevention of antibiotic resistant infections in the ICU.

Inulin is a naturally occurring, non-digestible polysaccharide derived from chicory root or other sources such as agave and garlic. Inulin is a prebiotic and considered a dietary supplement by the U.S. Food and Drug Administration. Inulin is indigestible by humans, but colonic anaerobic bacteria break down inulin into short-chain fatty acids. Inulin is commercially available and relatively inexpensive, and there are several producers of Good Manufacturing Practice (GMP)-rated inulin. Inulin will be tested for preventing life-threatening infections with MDR bacteria.

Inulin increases SCFA levels and improves gut barrier function. In animals, inulin increases cecal SCFA content with evidence of improved gut barrier function including an increase in colonic crypt height, goblet cells, mucus content, and expression of the antibacterial lectin RegIIIg[33] which maintains normal separation between the microbiota and intestinal epithelial cells.[34] A diet rich in fiber including inulin also lowers levels of circulating endotoxin,[35] mitigates chemical colitis[33] and improves survival after endotoxin injection or cecal ligation/puncture.[30] SCFA-producing bacteria, especially Cluster IV and XIVa Clostridia, block host cell invasion by enteric pathogens[36,37] via induction of colonic T regulatory cells and other mechanisms.[38]

Inulin has been shown to be extremely safe and well-tolerated in humans. The prebiotic inulin decreases inflammation and has bifidogenic and butyrogenic effects on the microbiome, effects that promote SCFA production.[31] A randomized trial of inulin resulted in decreased levels of serum markers of inflammation (C-reactive protein) and bacterial translocation (lipopolysaccharide, LPS) as well as increased fecal Bifidobacteria and SCFA-producing bacteria (Clostridial clusters IV and XIVa).[32] In healthy volunteers, inulin increases Cluster IV and XIVa Clostridia including *F. prausnitz*[32,39] with improved microbiome diversity and richness.[40] In community-dwelling elderly, an inulin-containing prebiotic increased gut microbiome diversity and decreased the abundance of potentially pathogenic Gram negatives.[41] No serious adverse events related to inulin have been reported.

Alterations to the Gut Microbiome in Critically Ill Patients.

As part of a larger prospective cohort study, we performed analyses on 93 critically ill adults. Deep rectal swabs were obtained on ICU patients within 4 hours of ICU admission and exactly 72 hours later, and analyzed using 16S rRNA sequencing and cultured for vancomycin-resistant *Enterococcus* (VRE). Clinical and microbiome data were analyzed to determine (1) the key microbiome changes that took place in the ICU over 72 hours, (2) how these changes may have affected gut microbiome colonization resistance, and (3) downstream effects on antibiotic resistance within the gut microbiome.

We used a novel approach to enroll patients, collecting samples but deferring consent until the 72-hour follow-up if subjects were unable to consent at the time of admission.[42] We have been highly successful at identifying and reaching eligible study subjects at the time of ICU admission, a process that will be important to the success of the proposed trial, and 57% of eligible patients agreed to take part in the cohort study.

We found that critically ill patients rapidly lose SCFA-producing bacteria with a corresponding expansion in antibiotic-resistant pathogens within the gut microbiome. These data are summarized below.

Critically Ill Patients Rapidly Lose SCFA-Producing Bacteria.

In our ICU patients, there was a rapid loss of SCFA-producing bacteria, most notably within Clostridia Clusters IV (*Faecalibacterium prausnitzii*) and XIVa (*Blautia, Coprococcus, Roseburia*, and Ruminococcus). These were dramatic changes, ranging from 1-2 fold median losses to a more than 8-fold median decline in the relative abundance of

*F. prausnitzii* over 72 hours. Previous smaller ICU-based studies have also demonstrated rapid shifts away from anaerobic commensals, which have been associated with worse clinical outcomes.[43,44]

SCFA-Producing Bacteria Play an Essential Role in Colonization Resistance.

The concept of colonization resistance within the gut microbiome is widely accepted yet difficult to directly measure. The most commonly used surrogates for colonization resistance are the diversity of the gut microbiota and its resilience in response to perturbation.[45,46] We found a stepwise progression where higher levels of SCFA producers associated with significantly greater gut microbiome diversity (FIG. 3A) and resilience (p for trend <0.01). In select populations receiving broad-spectrum antibiotics, low fecal microbial diversity has been shown to predict VRE bacteremia and mortality.[45,47,48] These data support the hypothesis that SCFA producers play an essential role in maintenance of normal gut colonization resistance and demonstrate that loss of diversity is a reasonable surrogate for loss of colonization resistance, with significant consequences.

Antibiotics are the Crucial Risk Factor for Loss of SCFA-Producing Bacteria and for the Development of Antibiotic Resistance.

With progressive ICU hospitalization there is a steady increase in the proportion of patients colonized with antibiotic resistant pathogens.[24] From our ICU data, we used multivariable modeling to test for changes in SCFA producers across relevant baseline clinical factors and ICU interventions such as exposure to antibiotics, mechanical ventilation, and hemodialysis. Exposure to broad spectrum antibiotics was the only potentially modifiable risk factor which associated with loss of SCFA producers after 72 hours (OR 2.90, 95% CI 1.06-7.91), and the strength of this association was unchanged after adjusting for potential confounders including acuity of illness.[49] Moreover, exposure to antibiotics was also the most important risk factor for an expansion in *Enterococcus* after 72 hours (OR 2.66, 95% CI 1.08-6.57). To build on these findings, we randomly selected three subjects from our ICU cohort for whole genome sequencing (WGS) to compute the fraction of the gut microbiome comprised of antibiotic-resistance genes (the "resistome"). Large resistome gains were seen only with broad-spectrum antibiotics in the ICU (FIG. 5).

Loss of SCFA Producers Corresponds with an Expansion in Antibiotic-Resistant Pathogens.

Figure 6:
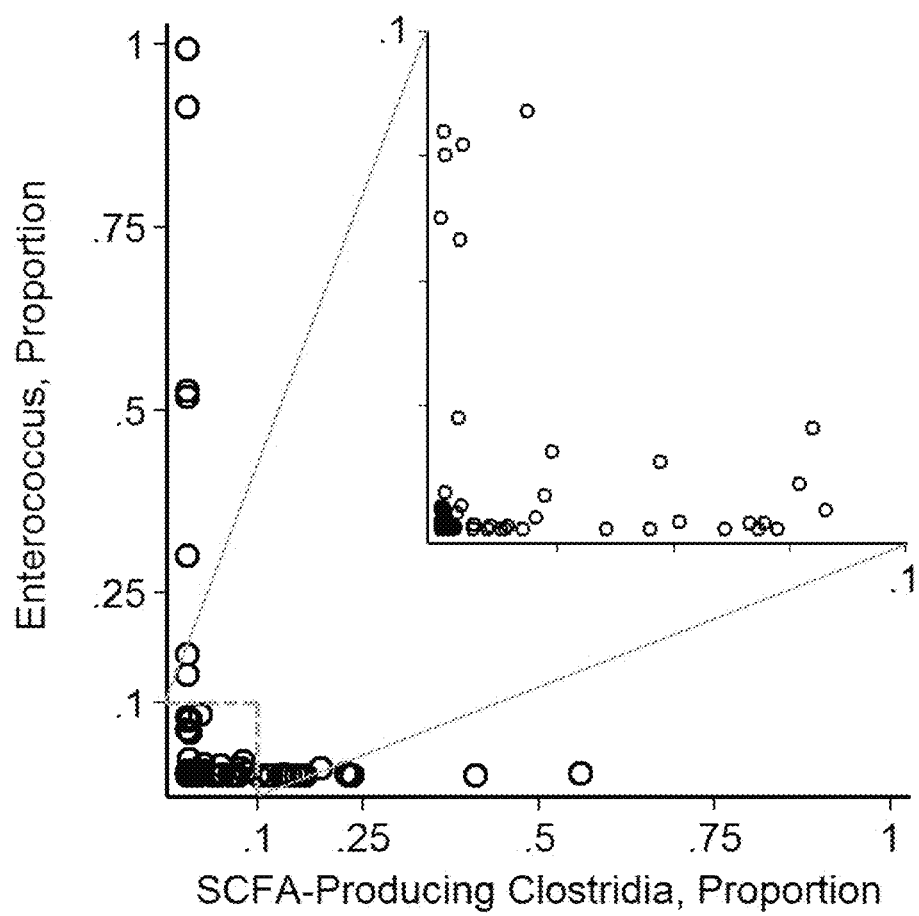
FIG. 6. High levels of *Enterococcus* are only observed with low levels of SCFA-producing bacteria. Total relative abundance cannot exceed 1.0, so domination by SCFA producers excludes the possibility of high levels of *Enterococcus*. However, the same effect was observed when the relative abundance of both groups was <0.1 (inset).

In animals, loss of the SCFA producer *Blautia* prevents VRE colonization after antibiotic treatment by producing a metabolite that directly inhibits growth of VRE.[50] In humans, prolonged ICU stays have been associated with a progressive loss of Clostridia with replacement by *Enterococcus*[22] and low fecal SCFA levels have been correlated with domination by *Enterococcus* and *Staphylococcus*.[23,51] In our preliminary data, there was a 20-fold increase in the relative abundance of *Enterococcus* within the gut microbiome and a reciprocal relationship where high levels of *Enterococcus* were only observed with extremely low levels of SCFA producers (FIG. 6). Culture confirmed that the *Enterococcus* seen on sequencing was vancomycin-resistant. To further explore the relationship between levels of SCFA producers and antibiotic resistant pathogens, we assessed for pathogen domination (defined as ≥30% of 16S sequences) and found that low levels of SCFA producers were also associated with domination by the pathogens Enterobacteriaceae, *Staphylococcus*, and *Pseudomonas*.

Antimicrobial Resistance Increases as SCFA Producers are Lost.

Figure 7:
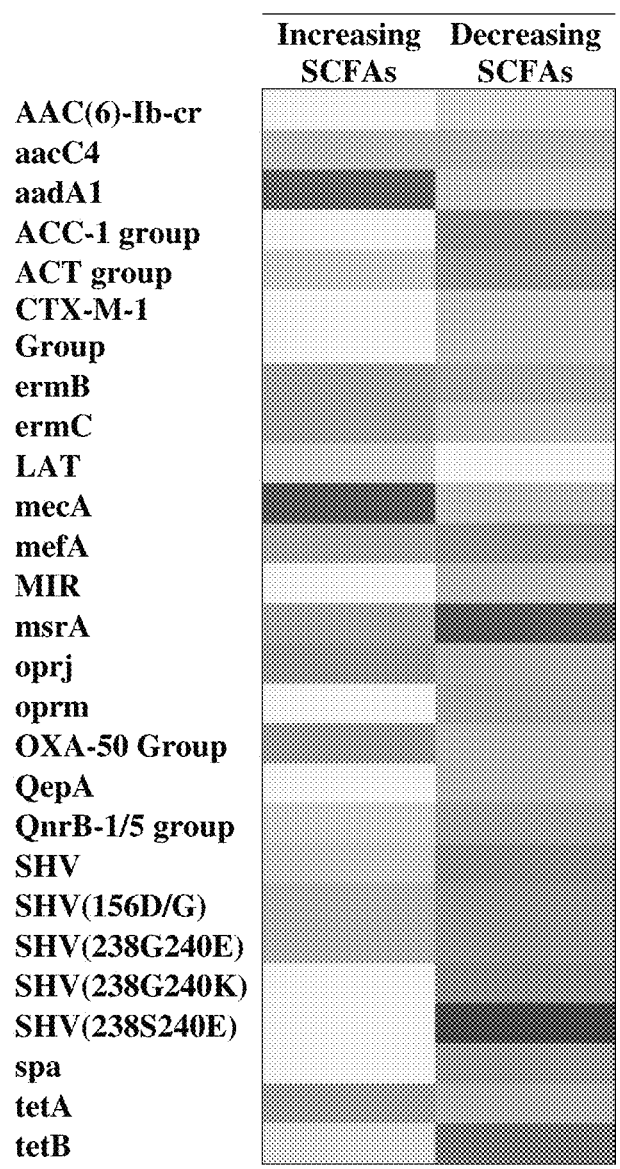
FIG. 7. Larger gains in resistance were seen in patients with decreasing levels of fecal SCFA-producing bacteria. Darker colors represent greater increases in antibiotic resistance. Of 87 antibiotic resistance genes tested, 26 showed significant increases during the initial 72 hours in the intensive care unit.

Six subjects from the ICU cohort were selected at random including 3 who gained SCFA producers during the initial 72 hours in the ICU and 3 who declined in SCFA producers during the same time period. Multiplex qPCR was performed across 87 antibiotic resistance genes and the results were pooled (FIG. 7). Gains in antibiotic resistance were lower among the subjects with increasing compared to decreasing SCFAs, implying that growth of SCFA-producing bacteria may promote colonization resistance against the ICU pathogens that carry common antibiotic resistance genes.

Prior Studies of Medication Effects on the Gut Microbiome.

We conducted a cross-over trial aimed at elucidating the effects of proton pump inhibitors (PPIs) on the fecal microbiome, a mechanism by which PPIs may increase susceptibility to *Clostridium difficile* infection (CDI).[52] Twelve healthy volunteers had a 4-week run-in period on no antisecretory therapy, and then were treated with 4 to 8 weeks of omeprazole (a PPI) 40 mg twice daily. The fecal microbiome was assessed using 16S rRNA gene sequencing. Neither 4 nor 8 weeks of PPIs altered diversity (p=0.48). However, 4 weeks of PPIs resulted in significant within-individual increases in *Enterococcaceae* (p=0.03) and *Streptococcaceae* (p=0.002) and decreased *Clostridiaceae* (p=0.03), taxa changes associated with the development of CDI. PICRUSt functional analyses were notable for increases in gene pathways for bacterial invasion and renin-angiotensin in those who received 8 weeks of PPIs. There were no changes in fecal bile acids. In sum, these results demonstrated that PPIs induce specific microbiome changes that likely increase susceptibility to *C. difficile* infection.

Objectives and Methods

The objectives of this project include testing inulin in the ICU by randomizing 30 critically ill patients to placebo or inulin at two doses. The results of this Phase 1/2 trial will provide effect size estimates, feasibility, and safety data in support of larger, subsequent phase trials. We will also determine the optimal population in which to conduct such a trial. The objectives of this project also include determining the efficacy of inulin for the prevention of MDR infections in the ICU.

To Determine the Feasibility and Safety of Inulin for the Prevention of Antibiotic Resistant Infections in Critically Ill Patients.

We will block randomize 30 critically ill adults who are receiving broad-spectrum antibiotics for sepsis to one of three arms: placebo, inulin 8 g twice daily, or inulin 16 g twice daily for one week, with bedside follow-up for 30 days or until hospital discharge and long-term follow-up for 6 months. We will measure enrollment rate, protocol adherence, and intervention fidelity in support of larger Phase 2 and 3 trials and will assess the safety of the intervention.

Hypothesis:

The administration of inulin to critically ill patients is both feasible and safe.

To Assess the Effect of Inulin on within-Individual Change in Antibiotic Resistance.

Within this cohort, we will determine effect size estimates in support of larger Phase 2 and 3 trials. We will compare within-individual changes in antibiotic resistance in subjects taking inulin or placebo through two approaches: 1) antibiotic resistance gene burden as assessed by multiplex qPCR; and 2) culture of the predominant and clinically-relevant antibiotic-resistant bacterial classes: vancomycin-resistant Enterobacteriaceae (VRE), extended-spectrum beta-lactamase (ESBL) producing Gram-negative bacteria, *Klebsiella pneumonia* carbapenemase (KPC)-producing bacteria, and methicillin-resistant *Staphylococcus aureus* (MRSA). We will also perform exploratory analyses to assess the effects of inulin on within-individual changes on the gut microbiome by 16S rRNA gene sequencing as well as alterations in fecal SCFA levels.

Hypothesis:

The administration of inulin to critically ill patients decreases antibiotic resistance.

To Determine the Optimal Target Population for Testing Inulin for the Prevention of Antibiotic Resistant Infections.

We will conduct a retrospective cohort study within the Veterans' Administration (VA) VINCI system to identify risk factors for ICU-acquired MDR infections, and the time course for the development of these infections. This will provide key information for the optimal design and patient selection for subsequent larger Phase 2 and 3 trials.

Hypothesis:

Cumulative exposure to antibiotics is associated with subsequent antibiotic-resistant infection in an antibiotic class-specific manner. Additional risk factors for MDR infections can be identified within the VA ICU population.

The results of these studies will provide the necessary data in support of subsequent larger Phase 2 and 3 trials testing inulin in critically ill patients with the clinical outcomes infection of MDR bacteria and mortality. The present method is a highly novel yet simple therapy to reduce the spread of antimicrobial resistance and prevent infections with MDR organisms to improve outcomes in critically ill patients.

Method

To Determine the Feasibility and Safety of Inulin for the Prevention of Antibiotic Resistant Infections in Critically Ill Patients.

We will perform a double-blind, randomized controlled trial of inulin in the ICU with three arms (placebo, inulin 8 g twice daily, and inulin 16 g twice daily). Subjects will be treated with inulin or placebo for 7 days with bedside follow-up for 30 days or until hospital discharge and long-term follow-up for 6 months. Within this phase 1/2 trial, we will measure enrollment rate, protocol adherence, and intervention fidelity in support of a Phase 3 trial and will assess the safety of the intervention.

Population.

The study will enroll consecutive adult ICU patients who meet criteria for sepsis, are receiving appropriate antibiotics, and can complete a bedside assessment within 4 hours of ICU admission and receive the trial intervention within 6 hours of ICU admission. Specific inclusion and exclusion criteria are as follows:

Inclusion Criteria

TABLE 6

Calculation of the Sequential [Sepsis-Related] Organ Failure Assessment (SOFA) score.

| Criteria | Point Value Assigned |
| --- | --- |
| PaO2/FiO2 ratio | |
| <400 | +1 |
| <300 | +2 |
| <200 and mechanically ventilated | +3 |
| <100 and mechanically ventilated | +4 |
| Platelets ( × 10³/uL) | |
| <150 | +1 |
| <100 | +2 |
| <50 | +3 |
| <20 | +4 |
| Glasgow Coma Scale | |
| 13-14 | +1 |
| 10-12 | +2 |
| 6-9 | +3 |
| <6 | +4 |
| Bilirubin (mg/dL) | |
| 1.2-1.9 | +1 |
| 2.0-5.9 | +2 |
| 6.0-11.9 | +3 |
| ≥12.0 | +4 |
| MAP or vasopressor requirement | |
| MAP < 70 mm/Hg | +1 |
| Dop ≤ 5 or Dob (any dose) | +2 |
| Dop > 5 or Epi/Nor < 0.1 | +3 |
| Dop > 15 or Epi/Nor > 0.1 | +4 |
| Creatinine (mg/dL) | |
| 1.2-1.9 | +1 |
| 2.0-3.4 | +2 |
| 3.5-4.9 | +3 |
| ≥5.0 | +4 |

MAP: mean arterial pressure;
Dop: Dopamine;
Dob: Dobutamine;
Epi: Epinephrine:
Norepi: Norepinephrine.
Calculation of SOFA as per Vincent et al.

Medical ICU.

Subjects will be newly admitted to one of two CUMC medical ICUs during the study enrollment period;

Age.

Subjects will be eighteen or more years old at the time of ICU admission;

Sepsis.

Subjects will meet criteria for sepsis with life-threatening organ dysfunction caused by infection (Sepsis-3 third international consensus definition, 2016).[79] According to this definition, life-threatening organ dysfunction is operationalized as an increase in the Sequential [Sepsis-Related] Organ Failure Assessment (SOFA) score of ≥2 points above baseline. The SOFA score is a combination of clinical and laboratory-based criteria; calculation of the SOFA is shown in in Table 6.[80] Dynamic changes in SOFA score are highly correlated with mortality. SOFA increases of <2 are associated with an ICU mortality of <6% whereas SOFA increases of ≥2 were associated with a 37% mortality when initial SOFA was 2-7, 60% mortality when initial SOFA was 8-11, and >90% mortality when initial SOFA was >11.[80-82] Under Sepsis-3, if prior patient data is unavailable the SOFA baseline is assumed to be zero. SOFA scores reflect the Systemic Inflammatory Response Syndrome (SIRS),[83] but SIRS features do not well predict culture-proven infections and the biology underlying SIRS due to sepsis is unique.[84,85] Therefore, Sepsis-3 criteria also require patients to have a known or suspected infection, defined as sampling of blood or any other body fluid for infection with concurrent administration of appropriate antibiotics (see below). These criteria were developed in data from 12 community and academic hospitals (1.3 million encounters) and validated across 4 external datasets comprising both community and tertiary care facilities (700,000 encounters);[79] Appropriate antibiotics. Subjects will receive appropriate antibiotics, which will be operationalized as (1) among subjects with positive culture data, the antibiotics within classes where the organism is susceptible based on standard Clinical and Laboratory Standards Institute (CLSI) cut-offs[86]; or (2) among subjects receiving empiric antibiotics (i.e., with negative cultures), antibiotics within classes with significant anaerobic activity. This will include β-lactam/β-lactamase inhibitor combination antibiotics, carbapenems, cephalosporins (generation 2 or greater), fluoroquinolones, and metronidazole. This definition covers 7 of the 8 of the most commonly prescribed classes of antibiotics in U.S. hospitals from 2006-2012 (vancomycin is intentionally excluded).[87] Antibiotics must be received within the 72 hours before ICU admission or be actively ordered at the time of bedside screening; Prompt intervention. Subjects will complete study enrollment within 4 hours of ICU admission so that the intervention can be administered within 6 hours of ICU admission. Nursing time stamp data will be retrieved from the electronic medical record (EMR) to define the time of ICU admission. The gastrointestinal microbiome changes rapidly following ICU admission (in our previous studies) and the efficacy of the intervention may wane as the window between ICU admission and the intervention increases.[22,43,44]

Exclusion Criteria

Inability to Receive Oral or Enteric Fluids.

Patients will be excluded if they are nil per os or are unable to take fluid by mouth or delivered via enteric nasal or oral tube;

Allergy.

Patients will be excluded for safety reasons if they have a known chicory allergy. Serious chicory allergies are exceedingly rare although mild respiratory symptoms and IgE-mediated food allergies have been reported;[88]

Hyponatremia.

Patients will be excluded for hyponatremia with serum sodium ≤128 mEq/L because the intervention will be delivered in 500 ml of free water daily. If subjects develop hyponatremia (serum sodium serum sodium 125-128 mEq/L) after enrollment and randomization which persists at the time the subject is due to receive the study intervention, the study team will confer with the treating ICU team regarding whether the intervention should be deferred or further concentrated in order to minimize free water. If subjects develop severe hyponatremia (serum sodium serum sodium ≤124 mEq/L) after enrollment and randomization, the intervention will be withheld;

Depleted Microbiota.

Patients will be excluded for any of the following criteria: *Clostridium difficile* infection (CDI) within 90 days, ICU admission within 90 days, continuous hospitalization ≥10 days, or continuous antibiotics ≥5 days. These exclusion criteria were selected because they may represent conditions where levels of inulin metabolizing gut bacteria are likely to be already very low and therefore situations where the potential benefit of inulin may be limited;

Bowel Surgery.

Patients will be excluded for surgeries involving the intestinal lumen within 30 days. The most common side effects from inulin are subjective bloating and abdominal distension.[32,89-91] Although this bloating appears to be mild and self-limited, patients with recent bowel surgeries may be at greatest risk for such symptoms and will therefore be excluded;

Limited Treatment Goals.

Patients will be excluded if they have Do Not Resuscitate (DNR) or Do Not Intubate (DNI) status or if they have "no escalation of care" orders. Such patients have limited treatment goals and will be excluded to minimize heterogeneity;

Issues Related to Consent.

Patients will be excluded if they lack capacity for consent and have no appropriate Legally Authorized Representative (LAR).

TABLE 7

Time course of intervention and assessments during the study.

| | Inulin | | | Monitoring | |
|---|---|---|---|---|---|
| Type of Assessment | Day 0 | Day 3 | Day 7 | Day 30 | 3 months | 6 months |
| Rectal swab | X | X | X | X | | |
| Whole stool | X | X | X | X | | |
| Oral swab | X | X | X | X | | |
| Gastric Aspirate | X | X | X | X | | |
| Clinical data | X | X | X | X | X | X |
| Telephone follow-up | | | | | X | X |

Intervention.

Block randomization will be performed with 1:1:1 random computer allocation of subjects into the three study arms. In the two inulin arms, chicory root-derived inulin (PubChem SID 329758326, Sigma-Aldrich, St. Louis, Mo.) will be diluted in 250 ml of sterile water and given at 8 or 16 g twice daily. At this dilution, inulin is indistinguishable from water and the placebo arm will receive the same volume of sterile water alone. Prior studies have shown that these doses are both safe and sufficient to confer benefit,[32,92] even in the setting of critical illness.[93-96] Subjects, investigators, and the treating ICU team will be blinded to the intervention arm, with blinding managed by the CUMC Research Pharmacy which will provide labeled, de-identified fluid bags containing inulin/placebo. The intervention will be taken orally or given as enteric feeding by nursing staff overseen by the study team, with the first dose administered within 6 hours of ICU admission. The time course for the intervention and remaining study assessments is shown in Table 7.

Enrollment Strategy.

Patients will be identified at the time of ICU bed allocation and pre-screened for inclusion/exclusion criteria at the time of ICU admission using the EMR. Pre-screening allows us to identify potential subjects prior to their physical arrival in the ICU, and we have used this strategy in the past to minimize the period between ICU admission and enrollment/sample acquisition.[42] After consultation with the treating ICU team, subjects who meet pre-screening criteria will have the eligibility evaluation completed at the ICU bedside. We anticipate that >50% of patients will lack decision-making capacity and we will accept consent from a surrogate in these situations, as previously described by our group.[42]

Study Assessments.

Samples will be gathered and bedside assessments made at the following intervals after ICU admission or until hospital discharge/death: baseline, 3 days, 7 days, 14 days, and 30 days. During study assessments, data will be combined from the following sources: (1) samples collected by the study team, (2) bedside assessments, and (3) data from the EMR and an existing infection surveillance system (Table 8).

TABLE 8

Measurements Planned for Aim 1.

Measurements

Flocked rectal swabs × 2 (Copan Diagnostics)
Spontaneous whole stools: 4 × 8 ml
Gastric aspirates: 2 × 8 ml
Cotton-tipped oral swabs × 2 (Epicentre) Biotech)
Urine: 2 sterile 8 cc containers
Blood: 6 ml serum-separator & 8 ml EDTA tubes
Bedside Assessment Origin for admission (hospital, OR, ER, ICU)
Neurological: Glasgow Coma Scale
Life support and lines:
Use of mechanical ventilation
Presence of hemodialysis
Presence of bloodstream catheters
Presence of urinary catheters
Electronic Medical Record & Infection Surveillance System Demographic information Clinical: temperature, heartrate, BP
Comorbidities (Charlson Index)
Laboratory data: WBC, Hct, Alb, Cre
Receipt of antibiotics
Receipt of acid suppression medications
Culture-proven organisms causing infections
Antibiotic susceptibility of infecting organisms
Site of infections OR: operating room;
ER: emergency room;
WBC: white blood cell count;
Hct: hematocrit;
Alb: albumin;
Cre: creatinine.

Samples Collected by the Study Team.

At the time of each study assessment, the study team will collect samples at the ICU bedside. Sample collection is focused around rectal swabs because the timing of swabs (as opposed to whole stools) can be precisely dictated and because rectal colonization with MDR bacteria best reflects overall MDR colonization status[97-101] and risk for subsequent infection.[102] At each study assessment, flocked nylon swabs of the rectum will be performed in duplicate to allow independent processing of swabs for 16S rRNA gene sequencing and for bacterial culture of MDR bacteria. Swabs to be sequenced will be flash-frozen at −80° C. for long-term cold storage[103] and batched extraction;[104] swabs to be cultured will be transported on soy broth with 20% glycerol (Becton Dickinson) for culture or, when culture cannot be performed immediately, for storage overnight at 4° C. and culture the following morning.[105] The following additional samples will be gathered for future analyses:

Whole stools. Nursing staff working in conjunction with the study team will collect the first spontaneous whole stool subsequent to each study assessment. 4×8 ml aliquots of stool will be flash-frozen and stored at −80° C.

Gastric aspirates. When a nasal or oral gastric tube is already in place, a 60 cc sterile syringe will be used to gently withdraw 2×8 ml aliquots of gastric fluid. In subjects who have a gastric tube but in whom no fluid can be directly withdrawn, previously collected fluid stored in the wall suction canister will be accepted. In subjects who lack a gastric tube, this sample will be deferred.

Oral swabs. Two cotton-tipped oral swabs will be used to gather a composite of the oral flora by brushing the following consecutive locations ×10 each: left cheek, right cheek, hard palate, tongue, floor of the mouth, and maxillary gingivae. A similar sampling strategy was used in the Human Microbiome Project.[106] Swabs will be flash frozen and stored at −80° C.

Urine. ICU nurses operating under the direction of the study team will withdraw 2×8 ml of urine using standard technique from the urinary catheter sampling port. In patients who lack a urinary catheter, clean catch urine samples will be accepted and will be aliquoted as above.

Blood. It is anticipated that many subjects will have a central venous catheter in place. When this is the case, ICU nurses operating under the direction of the study team will withdraw a 6 ml serum-separator and 8 ml EDTA tube. When subjects lack a central venous catheter, blood will be drawn peripherally using standard technique. When possible, in order to minimize accessing of central venous catheters or peripheral blood draws, the study team will time these blood draws to coincide with blood draws performed for clinical reasons.

Bedside Assessments.

During each study assessment, a study-specific Case Report Form (CRF) will be used to record the following data: origin for admission (classified as from the hospital floor, operating room, emergency room, or outside ICU transfer based on the most recent location prior to CUMC ICU admission); the Glasgow Coma Scale (GSC),[107] a simple bedside instrument that has been used for over 40 years to assess level of awareness based on eye, motor, and verbal response to stimuli, has been validated in the ICU setting, and is a component of ICU severity scores (e.g., APACHE[49]); the use of life support (classified as present vs absent) including the use of mechanical ventilation, hemodialysis, or additional life-support devices such as extra-corporeal membrane oxygen (ECMO) or an intra-atrial balloon pump (IABP); and the presence or absence of intravenous lines or catheters including a central venous catheter, urinary catheter, arterial catheter, nasal or oral gastric tube, or rectal tube. Using duplicate data entry, anonymized CRF data will be transferred into a secure on-line database. This will be a REDCap database custom-designed for the proposed trial by the CUMC Data Coordinating Center.

Data from the Hospital EMR and an Existing Infection Surveillance System.

Demographic and selected clinical data will be retrieved from the hospital EMR (Table 8). CUMC inpatient management is paperless, includes all laboratory testing data, and also includes all nursing flowsheets where vital signs are recorded at <2 hour minimum intervals in the ICU. Temperature, heartrate, respiratory rate, and blood pressure will be documented as the mean value over the three recordings prior to study assessment time. The CUMC hospital EMR is the complete medical record which is designed to be mined for medical research and has been utilized for similar research by us in the past.[64,108] Clinical data related to infections will be retrieved through the Health Information Technologies to Reduce Healthcare-Associated Infections (HIT-HAI) system.

HIT-HAI is an infection surveillance system that has existed since 2007 and incorporates complete hospital data from CUMC and 3 other Columbia-affiliated hospitals in New York. HIT-HAI actively draws together data from diverse sources. The overall goals of HIT-HAI are to (1) evaluate the effectiveness of infection control in the ICU and other acute care settings; (2) examine how changes in clinical care impact risk for healthcare-associated infections over time; and (3) compare infection control practices across ICUs differences with respect to rates of *Clostridium difficile* infection and infections with MDR organisms. HIT-HAI is the ideal dataset with which to study MDR ICU-acquired infections, has been used in an extensive list of publications related to MDROs,[1,110-113,64,109] Currently HIT-HAI contains records for over 500,000 unique patients including all CUMC ICU patients. Specific data available within HIT-HAI includes patient demographics, ICU type, comorbidities (extracted from ICD-9 or ICD-10 codes), microbiology data (complete culture results including antibiotic susceptibility testing results), all laboratory data (including individuals' white blood cell count, albumin, and serum creatinine), patient diet information, patient-specific medications received (including acid suppression medications, antibiotics, and immunosuppressant medications), and information regarding other ICU interventions such as the placement of indwelling vascular or urinary catheters, and the receipt of mechanical ventilation or hemodialysis. This invaluable resource allows us to extract extensive clinical information from the medical record rapidly and accurately. Furthermore, HIT-HAI facilitates long-term follow-up of subjects for clinical outcomes including the development of MDR infections, hospital or ICU readmission, and all-cause mortality. Data will be retrieved quarterly from HIT-HAI.

Main Assays.

From the above samples, the following assays will be performed:

Quantitative PCR (qPCR).

DNA will be extracted from rectal swabs (MoBio PowerFecal, Carlsbad, Calif.). DNA will then be assessed for the presence of antibiotic resistance genes using multiplex quantitative PCR (Qiagen Cat. No. 330261, Valencia, Calif.). This microbial DNA array assay targets 87 common antibiotic resistance genes (Table 9)[114] and facilitates testing for highly prevalent bacterial antibiotic resistance genes in a single reaction with both resistance gene identification (present vs absent) and quantitative profiling (expression relative to an internal standard). 250 ng of template genomic DNA will be added to each reaction on a 96-well plate which will be run on a StepOnePLus RT-PCR machine using the following cycling conditions: initial denaturation for 10 min at 95° C., cycling 45×15 sec at 95° C. denaturing followed by 2 min at 60° C. annealing and extension. Controls will detect the presence of bacterial DNA, PCR inhibitors and background (no template control (NTC). PCR cycle thresholds ($C_T$) of <35 will be considered positive for the presence of any given gene. Adequate reactions will be determined by $C_T$ values of <29 for pan-bacterial reference genes (e.g., 16S rRNA, gyrA, recA, rpoB)[115] and positive PCR controls (PPC) $C_T$ values of <24. Linearity and sensitivity for this PCR have been determined using synthetic templates over a 6-log serial dilution ranging from 1 to 1 million copies. For SHV variants and other variants, this qPCR is able to reliably distinguish single nucleotide polymorphisms occurring at different sites and the results have been verified across multiple antibiotic resistance genes using pyrosequencing.[114]

TABLE 9

Resistance types and genes tested in multiplex PCR for antibiotic resistance genes.

| Resistance Category | Resistance Genes |
| --- | --- |
| Aminoglycoside | aacC1, aacC2, aacC4, aadAl, apha6 |
| Class A beta-lactamase | BES-1, BIC-1, CTX-M-1, CTX-M-8, CTX-M-9, GES, IMI & NMC-A, KPC, Per-1, Per-2, SFC-1, SFO-1, SHV (156D) (156G) (238G240E) (238G240K) (238S240E) (238S240K), SME, TLA-1, VEB |
| Class B beta-lactamase | ccrA, IMP-1, IMP-12, IMP-2, IMP-5, NDM, VIM-1, VIM-13, VIM-7 |
| Class C beta-lactamase | ACC-1, ACC-3, ACT 5/7, ACT-1, CFE-1, CMY-10, DHA, FOX, LAT, MIR, MOX |
| Class D beta-lactamase | OXA-10, OXA-18, OXA-2, OXA-23, OXA-24, OOXA-45, OXA-48, XA-50, OXA-51, OXA-54, OXA-55, OXA-58, OXA-60 |
| Erythromycin | ereB |
| Fluoroquinolone | AAC(6)-Ib-cr, QepA, QnrA, QnrB-1, QnrB-31, QnrB-4, QnrB-5, QnrB-8, QnrC, QnrD, QnrS |
| Macrolide-Lincosamide | ermA, ermB, ermC, mefA, msrA |
| MDR efflux pump | oprj, oprm |
| Tetracycline | tetA, tetB |
| Beta-lactam | mecA |
| Vancomycin | vanB, vanC |
| PVL chain F | lukF |
| IgG binding protein A | spa |

Bacterial Culture.

Standard bacterial culture will be performed to assess the impact of the intervention on viable bacteria and to obtain semi-quantitative culture results. We will focus on MRSA, VRE, ESBL, and KPC. These bacteria are responsible for over 94% of all MDR bacterial infections in the ICU.[6] Flocked rectal swabs from each study assessment will be gently vortexed to dissociate DNA from the swabs into the broth media. Media will then be split into six equal aliquots and plated under a laminar flow hood on antibiotic resistant selective and non-selective agar. This includes culture for MRSA (Spectra-MRSA, Remel), VRE (Spectra-VRE, Remel), and ESBL or *Klebsiella pneumonia* carbapenemase (KPC)-producing bacteria (Uhlemann lab). In addition, we will plate cultures on Gram-positive (Columbia agar with 5% sheep blood, Becton Dickinson) and Gram-negative selective agar (MacConkey II agar, Becton Dickinson), The two non-selective Gram-positive (blood agar) and Gram-negative (MacConkey) plates will be inoculated directly and at three serial dilutions for semi-quantitation ($10^{-2}$, $10^{-4}$, and $10^{-6}$). Preliminary data show that these dilutions will yield a countable number of colonies. The 3 selective plates for MSRA, VRE, and ESBL/KPC will be inoculated directly only as our prior experience shows that colonies can be adequately distinguished. After 18-24 hours of aerobic growth, selective plates will be classified as positive vs negative for growth according to the media characteristics. The colony-forming units (CFUs) on the non-selective plates for Gram positives/negatives will be counted to provide relative quantification of each MDRO based on the total CFU counts from the non-selective plates. In situations with multiple non-selective plates showing growth, the plate showing 10-100 colonies will be used for CFU counting with results normalized to the $10^{-2}$ plate. From these plates, organisms will be selectively sub-cultured onto blood or MacConkey agar and identified using the VITEK 2 system (bioMerieux) and AST-N010/020 cards with confirmatory testing as needed. All resistant isolates will be stored at −80°

C. for future whole genome sequencing analyses. 16S rRNA Gene Sequencing. From extracted DNA, polymerase chain reaction (PCR) will be performed on a Bio-Rad T100 Thermal Cycler (Bio-Rad, Hercules, Calif.) to amplify the V4 hypervariable region of the 16S ribosomal RNA gene with primers derived from Klindworth et al.[116] appended with overhang sequences for compatibility with Illumina index and sequencing adapters (Illumina, San Diego, Calif.). Samples will be purified with Agencourt AMPure XP beads (Beckman Coulter, Jersey City, N.Y.). Low-cycle PCR will be performed to attach dual indices and Illumina sequencing adapters to the amplicons using Illumina's Nextera XT Index Kit. Samples will be purified with Agencourt AMPure XP beads and quantified using the Quant-iT broad range dsDNA Assay Kit (Thermo Fisher Scientific, Fair Lawn, N.J.). Libraries will be normalized, pooled, and denatured in preparation for cluster generation and sequencing. Sequencing of the 16S ribosomal RNA gene V4 region will be performed using the Illumina MiSeq 300PE platform.

Fecal SCFA Levels.

Whole stools will be aliquoted and tared aliquots diluted with 80% ethanol to be agitated at 4° C. After centrifugation, 20 µl of supernatant from the homogenized samples will be mixed with 20 µl of 200 mM N-(3-Dimethylaminopropyl)-N'-ethylcarbodiimide hydrochloride (1-EDC HCl) in 5% pyridine and 40 uL of 100 mM 2-Nitrophenylhydrazine (2-NPH) in 80% acetonitrile (ACN) with 50 mM HCl. After a brief incubation, ACN will be added to the solution which will be injected onto a 6490 triple quadrupole mass spectrometer (Agilent, Santa Clara, Calif.) within the CUMC Irving Center's Core Biomarkers Core Laboratory and tested for concentrations of the SCFAs butyrate, acetate, and propionate. Residual stool aliquots will be stored for future analyses.

Clinical Outcomes.

This Phase 1/2 trial will be recorded to (1) provide preliminary data to guide future studies, (2) assess the fidelity of clinical outcome ascertainment, and (3) monitor for safety. The main clinical outcome of interest will be MDR infections, which will be defined as (a) infections with an organism cultured from any fluid or human body site that shows non-susceptibility in 3 or more major antibiotic classes based on standard CLSI cut-offs[86] and (b) delivery or intent to deliver appropriate antibiotics against that infection, defined as antibiotics either received or ordered within no more than 24 hours after culture result. For this definition, appropriate molecular testing (e.g., PCR for MRSA) will be considered equivalent to a positive culture. Additional clinical outcomes ascertained will include length of ICU stay, length of hospital stay, vital status, and the occurrence of adverse events (AEs) or serious adverse events (SAEs) with a focus on infections. Active ascertainment will be performed for clinical outcomes until 6 months after ICU admission (see Human Subjects Attachment). Bloating and feeding intolerance has been reported among ambulatory patients taking fiber preparations including inulin. In this study, it is anticipated that few subjects will be able to report on abdominal symptoms, and subjective bloating that does not reach the level of clinical attention will not be captured. To objectively assess for intolerance to the intervention, the Research Study Coordinator will make daily assessments for vomiting/feeding intolerance (classified as present or absent on that day), diarrhea (recorded as frequency of bowel movements over that 24 hour period), and tube feed residual volume (extracted from nursing flowsheets in the EMR for subjects receiving enteral feedings).

Long-Term Telephone Follow-Up.

Telephone interviews will be conducted with subjects or their surrogates 3 months after ICU admission and again 6 months after ICU admission. In the event that subjects are still hospitalized, these interviews will be conducted at the bedside. Vital status will be ascertained and, to minimize loss of follow-up information, we will interview subjects or surrogates to ascertain (1) discharge location type (classified as home, short-term rehabilitation, or long-term rehabilitation including skilled care facilities), (2) hospital admission to non-CUMC facilities after ICU discharge, (3) physician office visits after ICU discharge, and (4) infections or other adverse events after ICU discharge. If there are non-CUMC hospital admissions or other healthcare interactions, permission will be requested to obtain relevant records to determine the nature of infections and to assess for potential medium- to long-term AEs related to the study intervention. Among surviving subjects, the EQ-5D-5L (EuroQol 2009) will be used to determine health status across the domains of mobility, self-care, activity levels, pain, and anxiety/depression.[117,118] Use of this highly validated instrument will facilitate standardization and generalizability of results and will provide preliminary data for post-ICU discharge monitoring for later phase trials. This instrument can be applied via telephone and was recommended in 2017 for post-ICU assessment of overall well-being after a three-round modified Delphi process involving clinical researchers from over 16 countries, patients/caregivers, clinicians, and research funders.[119] EQ-5D-5L responses have the potential to vary depending on whether answers are provided on patients versus surrogates,[120] and therefore we will additionally assess post-ICU disability using Katz' Index of Independence in ADLs (Activities of Daily Living).[121] Although focused on functional status rather than well-being, Katz' ADLs has been validated as an important patient-centered outcome across dozens of populations and unlike the EQ-5D-5L has high agreement between patients and caregivers.[122]

Approach.

Primary Outcome.

Count data will be recorded for patients who are eligible, screened, approached, and enrolled. The primary outcome is feasibility which will be evaluated in 3 ways: (1) the enrollment rate (enrolled)/(enrolled+refusals) over each 12 month period; (2) protocol adherence (proportion of randomized subjects who receive 1 or more doses of the allocated intervention), and (3) fidelity of the intervention (defined as the proportion of placebo/inulin allocated vs received and also categorically as receipt of 90% or more allocated doses of inulin/placebo). Feasibility goals are as follows:

Enrollment. The enrollment goal will be 30 subjects over 36 months with enrollment of no fewer than 10 subjects during any 12 month period of active enrollment.

Enrollment rate. The enrollment rate goal will be 25% overall with an enrollment rate goal of no less than 20% during any 12 month period of active enrollment.

Protocol adherence. The protocol adherence goal will be no less than 90% overall.

Fidelity of the intervention. The protocol fidelity goal will be no less than 70% overall and no less than 50% during any 12 month period of active enrollment.

Secondary Outcome.

The secondary outcome will be safety, evaluated by daily bedside monitoring for AEs and SAEs and for intolerance of the intervention and by short- and long-term telephone monitoring for infections and other major health events. AEs and SAEs will be reported to trigger immediate evaluation and initiation of the safety protocol.

Descriptive outcomes will include data regarding the flow of patients into the study and additional count data describing (1) the number of subjects who die before post-ICU admission day 3 and day 7, (2) length of hospital stay, and (3) mortality in-hospital, 30 days after ICU admission, and 6 months after ICU admission.

To Assess the Effect of Inulin on within-Individual Change in Antibiotic Resistance.

Within this cohort, we will determine within-individual effect size estimates data in support of larger Phase 2 and 3 trials.

Approach.

This study focuses on data derived from rectal swab samples because these samples best reflect the presence or absence of MDR colonization within the GI tract. Samples of saliva, gastric fluid, urine, and blood will be gathered and stored for additional analyses.

Primary Outcome.

We considered various outcomes to assess antibiotic resistance. We chose to analyze resistance using two distinct yet related outcomes that represent risk for development of infections with MDR organisms: (1) The total burden of antibiotic resistance genes within the gut microbiome. Antibiotic resistance genes are often harbored by non-pathogenic bacteria and subsequently transferred to and acquired by gut pathogens via plasmids and other mechanisms. Recent data indicates that the thresholds for such lateral gene transfers are lower than was previously believed.[123] The presence of these genes is therefore important, regardless of the organism that houses the gene. (2) The presence and amount of specific MDR organisms in the gut microbiome known to cause ICU-acquired infections. These organisms are directly responsible for the most difficult-to-treat ICU infections and for the majority of sepsis-related deaths in the ICU.

The primary outcome will be the within-individual change in bacterial antibiotic resistance, as assessed by change in resistance within antibiotic resistance gene categories (Table 9) from baseline to Day 7. We considered within-individual changes summing all of the antibiotic resistance genes (87 total) as the primary outcome assessment. However, this would assume that all of the resistance genes have similar clinical significance. Antibiotic resistance categories represent a more clinically relevant outcome, one that is keyed to antibiotic classes and thus directly tied to clinical decision-making.

Change in resistance within antibiotic gene categories will be assessed comparing baseline to Day 7, calculated using data from multiplex qPCR results from rectal swabs. For all subjects, each of the 87 antibiotic resistance genes will be scored as −1 (loss of resistance), 0 (no change), or +1 (gain of resistance) based on the qPCR changes from baseline to Day 7. Using this data, within-individual loss/gain of resistance will then be determined for each of the 14 resistance categories, once again scored as −1, 0, or +1 by adding the gene scores within each resistance category. For example, if the sum of gene changes within a resistance category is >0, the category will be classified as +1. For each subject, the score for each category will be summed; the potential score for any subject will range from −14 to +14 for each subject.

The primary outcome will be assessed by using an analysis of variance to compare subjects' sum change in resistance (Day 7 minus baseline) during the intervention period across the three study groups; this difference will be taken as the effect size estimate for future trials. We will explore longitudinal data by constructing a time series of resistance for each subject and on average, both for the total number of genes and for the sum of antibiotic resistance categories. If there is no significant difference between the 16 g and 32 g inulin arms, these arms will be combined for comparison against placebo and the Wilcoxon rank-sum test or t-test (if the data has a normal distribution) will be used to compare these two groups. In additional analyses, we will compare the within-individual change in resistance from baseline to Day 3 and, in subjects who complete the Day 30 assessment, from baseline to Day 30. Finally, we will test for a difference in acute severity of illness across groups based on SOFA score. If a significant group-based difference exists in SOFA scores, we will repeat analyses adjusting for SOFA. For this and all other analyses, all testing will be performed two-sided and results will be considered statistically significant at the alpha 0.05 level.

Secondary Outcome.

The secondary outcome will be the within-individual change in bacterial antibiotic resistance from baseline to Day 7. This will be calculated using bacterial culture results from rectal swabs. For all subjects, growth for each of the organisms of interest will be semi-quantitatively classified as 0 (absent) or a number 1-3 (based on the lowest dilution plate showing growth). The within-individual change (Day 7 minus baseline) will then be calculated for each subject and MDRO. We will compare the growth of MDROs during the intervention period (e.g., if a subject went from 3+ growth of MRSA at baseline to no growth on Day 7, the subject would be scored 0−3=−3 for MRSA). Again, we will visualize summary longitudinal data for each subject by constructing a time series of semi-quantitative growth of resistant organisms. Pairwise rank-sum tests will be used to compare subjects' sum change in resistant organisms during the intervention period across the three study groups. If there is no significant difference between the 16 g and 32 g inulin arms within each organism category, these arms will be combined for comparison against placebo. In additional analyses based on culture results, (1) within-individual changes from baseline to Day 30 will be compared among those who complete the Day 30 assessment; and (2) organisms of interest will be classified categorically (present vs absent) at each timepoint and time series data of these proportions will be compared across the three study arms. Finally, we will compare the overall antibiotic resistance burden for each organism (number of antibiotic classes showing non-susceptibility) between baseline and Day 7, compared across study groups.

Further Analyses.

Exploratory analyses will be performed including (1) 16S rRNA gene sequencing from rectal swabs, (2) comparing qPCR and culture results in rectal swabs, (3) using the non-rectal swab samples acquired (whole stools, saliva, gastric fluid, blood, urine), and (4) using clinical data.

Microbial Bioinformatic Analyses of Rectal Swabs.

The QIIME pipeline will be used to merge pair-ended reads with ≥Q20 quality Phred score and minimum overlap of 25%. Clustering of taxonomic units at 97% sequence similarity and alignment of quality-filtered contigs against the Greengenes[124] database, with additional sequences of interest retrieved from the National Center for Biotechnology as needed, will also be performed through QIIME. The resulting count table will include a summary of each identified operational taxonomic unit (OTU) and the number of reads assigned to this OTU in each sample. The R package "phyloseq" will then be used for diversity and phylogenetic analyses.

To test the hypothesis that inulin increases overall fecal bacterial diversity, we will compare within-individual change in alpha-diversity, reflecting the number of organisms and relative dominance of each type of organism within a single sample, across the 3 study groups (baseline to Day 3, baseline to Day 7). To test the hypothesis that inulin increases fecal bacterial stability, we will compare beta-diversity across the 3 same timepoints using both weighted and unweighted UniFrac distances and principal coordinate analysis (PCoA) plots, which measure similarity across different samples.

Our data suggests that fecal SCFA-producing bacteria within Clostridial Clusters IV and XIVa are drivers of microbiota diversity/stability although they comprise a relatively small fraction of the gastrointestinal microbiome. The relative abundance of SCFA-producers will therefore be calculated and compared across the three study groups. In addition, LEfSe[125] will be used to perform an untargeted analysis to determine any taxa which have significantly changed between baseline and Day 7. LEfSe tests for non-parametric differences in features (Kruskal-Wallis) and uses these results for paired least discriminant analysis (LDA) testing for a difference between pre-specified classes (Wilcoxon rank-sum). An LDA cut-off of $\geq 2.0$ will be applied with all taxa specified at the lowest possible hierarchical level. This analysis will be performed for each study group, and the results will be compared across groups to determine if there is gain/loss of similar taxa according to study group assignment. 16S sequencing provides details at the genus or species level but does not report on antibiotic resistance. Therefore, 16S results will be correlated with culture results to determine whether the observed 16S changes represent gain/loss of antibiotic resistant organisms. (For example, does an observed decrease in the abundance of *Enterococcus* sequences represent a decrease in VRE?). When necessary, selective qPCR targeting resistance cassettes will be used for MDRO ascertainment.

Comparing qPCR and Culture Results in Rectal Swabs.

To facilitate outcomes reporting in future trials, we will assess for correlations between culture and multiplex qPCR results. Each of the organisms of interest tested for by culture will be specified at the lowest possible taxonomic level in 16S sequencing and we will then test for correlations between 16S sequencing abundance and culture results. For example, MRSA will be specified as *Staphylococcus aureus* and we will then test for correlations between the relative abundance of *S. aureus* on 16S and the absolute abundance of MRSA in bacterial culture.

Other Samples.

Whole stools. Whole stools will be collected following each study assessment for the purpose of directly assaying fecal SCFA levels. An aliquot of these stools will be saved for future analyses such as metabolomics analyses, with the specific assays performed based on the findings from other testing. Stools from baseline, Day 3, and Day 7 will be assayed for levels of fecal SCFAs (butyrate, propionate, and acetate). Data summarizing these levels will be examined visually across the study groups at these 3 timepoints, with testing done to compare levels and to assess within-individual changes in these 3 fecal SCFAs. In an additional analysis, the SCFA levels will be summed and similarly compared. Combining all study groups, we will assess for correlations between levels of SCFAs and SCFA-producers (divided into tertiles), and for correlations between SCFAs and antibiotic resistance by qPCR. Results from these tests will improve understanding of the mechanisms by which inulin may foster growth of SCFAs and SCFA-producers.

Additional biospecimens. This trial will build a trove of biosamples that will be stored frozen for future analyses. These analyses will depend on the results from the project's main aims.

Clinical Data.

In exploratory analyses, we will assess for differences in relevant clinical outcomes between the 3 study groups. Using data from the EMR and from bedside study assessments, SOFA score will be calculated at the time of ICU admission, Day 3, and Day 7. We will explore SOFA score differences across the study groups. Rates of culture-proven infection, antibiotic-resistant culture-proven infection, and death will be calculated at Day 30 and based on the 6-month follow-up assessment. We will explore differences in these proportions across the 3 study groups and, among patients who develop infections, differences in the types of infections based on site, severity, and the infecting organisms. The results of these investigations will help guide the development of clinical outcomes for future trials.

Sample Size and Power.

There is no existing data which is directly comparable to this study and therefore no perfect precedent on which to base a power calculation. A sample size of 30 (n=10 per arm) will have 80% power to detect minimum differences of 0.6 standard deviation (SD) in cumulative antibiotic resistance among the three groups using an F-test at the alpha 0.05 level of significance. In addition, it will have 82% power to detect a difference of 1.3 SD in resistance between any 2 arms of the study and 92% power to detect a difference of 1.5 SD with resistance specified as a continuous variable and a normal distribution of data. We believe that these represent biologically meaningful differences. In order to meet the projected sample size, replacement subjects will be used for those who die or are discharged before the seventh post-ICU admission day. The project budget and timeline allow for these replacement subjects.

If inulin has no effect on antibiotic resistance by qPCR, we will examine the results of secondary outcomes and alternative definitions of resistance (e.g., based on bacterial culture). Discordant results between outcomes may lead to a change in the cut points used to characterize resistance or to alternative definitions for resistance, as has been done in prior studies.

The clinical importance of antibiotic resistance varies based both on the type of resistance and on the clinical scenario. This study will assess resistance via multiple methods including DNA- and culture-based methods.

The results will provide an appropriate level of confidence for the sample size decisions necessary for a larger trial. The results of bacterial culture will link qPCR and 16S sequencing findings to phenotypic antibiotic resistance and will help define endpoints in future studies. Samples gathered from the mouth, stomach, and urine can be used for resistance testing across body sites, and to determine how rectal MDRO colonization does or does not influence MDRO colonization at other body locations. Examination of clinical outcomes data including the development of resistant infections will guide adjudication of these outcomes for future trials focused on clinical rather than surrogate endpoints.

To Determine the Optimal Target Population within the VA Healthcare System for Testing Inulin for the Prevention of Antibiotic Resistant Infections.

We will conduct an ICU-based retrospective cohort study within the Veterans Health Administration to identify risk factors for ICU-acquired MDR infections and the time course for the development of these infections.

Approach.

This study will be conducted within the VA Informatics and Computing Infrastructure (VINCI) system.

Data Source.

VINCI was established in 2008 to facilitate utilization of the rich national VA data for research and links to a VA/CMS data repository. It is a free, secure, high-performance computing environment that provides access to the continuously updated VA national data, data analytical tools (e.g., statistical software), and runs entirely on a study-specific virtual workspace housed on VINCI server and accessible to multiple study personnel at any time. Within VINCI, we will access US national data related to military veterans via two linked datasets: the VA Corporate Data Warehouse (CDW), and the VA/Centers for Medicare and Medicaid Services (CMS) data from the VA Information Resources Center (VIReC). Veterans Health Administration (VHA) is the largest healthcare system in the US, covering over 8.7 million individuals.[126] As one of the earliest pioneers in implementing a system-wide electronic health record platform (i.e., VistA), the VA has comprehensive longitudinal electronic health data on millions of patients spanning several decades. CDW is the national repository of VA clinical and administrative data and can be linked to CMS data via unique patient identifiers. This approach provides access to data from the actual EMR for ascertainment of exposures and outcomes as opposed to data derived exclusively from insurance or billing records. High rates of follow-up within the VA system and linkage to CMS data will ensure completeness of long-term outcomes and key clinical endpoints (e.g., vital status).

Population.

Adults admitted to a VA hospital ICU from 2012-2017 with complete data within VINCI and with a minimum of 48 hours of ICU follow-up time will be considered for the study. 2012 was selected for the start of the study because it represents an epidemiological watershed, when the clinical importance of highly resistant Gram negatives first began to eclipse MRSA.[127,128] Additional inclusion criteria will be: eighteen or more years old at the time of ICU admission; sepsis criteria, defined as a modified SOFA score of ≥2 points above baseline; and receipt of appropriate antibiotics. For patients with multiple ICU admissions during the study period, only the first admission will be analyzed.

Primary Outcome.

The primary outcome will be the development of an ICU-acquired MDR infection, defined as culture-proven infection followed by receipt of appropriate antibiotics. Culture-proven infections will be operationalized as those with positive bacterial culture results from any site or fluid collected between 48 hours and 30 days after ICU admission and showing intermediate susceptibility or non-susceptibility across ≥3 antibiotic classes using the clinical breakpoints from the CLSI breakpoints in effect at the time when the culture was performed.[129,130] The following data will not be included: surveillance swab or culture results, non-culture microbiological data (e.g., PCR or EIA results), and specialized culture data (e.g., stool or vaginal fluid culture). Appropriate antibiotics will be operationalized as the antibiotics within classes where the organism shows susceptibility or empiric broad spectrum antibiotics that are initiated prior to finalization of cultures and continued after susceptibility testing is complete. Antibiotics must be received within the 72 hours before culture results or be actively ordered at the time of culture results. Secondary outcomes will be ICU length of stay (ICU discharge minus ICU admission), overall length of stay (hospital discharge minus ICU admission), hospital readmission, and death.

Exposures.

The primary exposure will be the intensity of antibiotic exposure, defined as the number of antibiotic class-specific days of antibiotic therapy divided by the number of days of follow-up time, and classified into quartiles. Subjects will be considered as having received a day of antibiotic therapy if they receive antibiotics at any dose and by any mode of administration on that day. Classes of antibiotics will be: amikacin, aminoglycosides, carbapenems, cephalosporins (classified based on generation), glycopeptides, fluoroquinolones, lincosamides, macrolides, monobactams, nitroimidazoles, penicillins, penicillins with beta-lactamase inhibitors, polymixin, sulfa-based, rifamycin, tetracyclines. Co-variables will include:

| Co-variable type | Details and/or definitions |
| --- | --- |
| Demographic information | Age, sex, race/ethnicity. |
| Location of origin | ER, OR, or hospital floor. Subjects already on the floor will be further classified into quartiles based on the duration of the floor hospitalization prior to ICU transfer. |
| Duration of prior hospitalization | Among subjects already hospitalized, the number of days of hospitalization preceding ICU admission. |
| Prior exposure to antibiotics | Class-specific receipt of antibiotics (classes above) will be recorded as present vs absent based on receipt within the previous 90 days based on hospital or pharmacy records. |
| Prior hospitalization | Classified categorically; among those with prior hospitalizations, the duration of time elapsed since the most recent hospitalization preceding the index admission |
| Prior ICU hospitalization | Classified categorically; among those with a prior ICU hospitalization, the date of the most recent ICU hospitalization preceding the index admission. |
| Prior colonization or infection with resistant organisms | Results of antibiotic susceptibility testing from any body site or fluid performed within the previous 90 days. In the main analysis, prior resistance will be classified as none, some (non-susceptibility across 1-2 antibiotic classes), or MDR (non-susceptibility across 3 or more classes). Those testing positive based on surveillance swabs or cultures (e.g., MRSA or VRE swabs) will also be classified as having prior colonization/infection with MDR organisms. |
| Comorbidities | Ascertained by ICD-9 or ICD-10 coding and used to compute the Charlson Comorbidity Index).[131,132] |

| Co-variable type | Details and/or definitions |
|---|---|
| Clinical data | Clinical variables will be captured at the time of ICU admission and, when available, 72 hours later. The timestamp from the ICU admission will be used to retrieve the most recent relevant laboratory values during the 24 hours preceding ICU admission; if no relevant values are available, then the value most closely following ICU admission over the subsequent 24 hours will be used. The following clinical variables will be included: temperature (° C.), heartrate (beats/min), respiratory rate nd (breaths/min), amean arterial pressure (mm Hg). |
| Treatment-related | The following variables related to treatment in the ICU will be captured, based on the 24 hours following ICU admission: use of immunosuppressants (including systemic steroids at a minimum daily dose of 5 mg prednisone or equivalent, calcineurin inhibitors, mTOR inhibitors, anti-metabolites, biologics including anti-TNFα agents, or mycophenolic acid), use of vasopressors (see Table 6 for categories), use of mechanical ventilation (present vs absent; when present further classified as invasive vs non-invasive), and use of hemodialysis (present vs absent; when present as continuous vs intermittent). |
| Laboratory data | Laboratory values will be captured in the same manner as clinical data, based on the ICU admission timestamp. The following laboratory data will be included: white blood cell count ($\times 10^9$/L), hematocrit (%), platelet count ($\times 10^3$/uL), total bilirubin (mg/dL), albumin (g/dL), creatinine (mg/dL), sodium (mEq/L), arterial PaO2 (mm Hg), FiO2 (%), and arterial pH. These variables, together with the clinical measures proposed, represent the main components of the most common ICU severity of illness scores (APACHE IV[49] and SOFA[80]). |

Statistical Approach.

Subset manual review will be conducted to validate the accuracy of the data. Descriptive statistics will be calculated and compared across those who did or did not develop antibiotic-resistant infections using a chi-squared test. Continuous measures will be summarized by mean, standard deviation, median, minimum and maximum, and will be graphically examined for normality with the Kolmogorov-Smirnov test.

In the primary analysis, subjects will be followed for 30 days or until death or hospital discharge. Time-to-event data will be examined by the Schoenfeld residuals for the proportional hazards assumption.[133] Uni- and multivariable Cox proportional hazards modeling will be performed to assess for a relationship between quartile of intensity of cumulative antibiotic exposure and ICU-acquired MDR infection, after appropriate analyses for death as a competing risk and for potentially confounding factors (see below). Antibiotics and exposures with an association (p<0.10) with MDR infections in univariable analysis will be used to build the final multivariable model by a stepwise variable selection procedure.

The following additional analyses will be conducted:

(1) Death as a competing risk. The primary analysis will be examined after stratification by death. If there is evidence of an interaction, a Fine-Gray approach[134] will be used to evaluate the relationship between the covariates and the cumulative incidence function. Because death may result from an undiagnosed MDR infection, a composite outcome of death and resistant infection will be explored.

(2) The timing of antibiotic exposure and MDR infection. To explore the possibility of protopathic bias (i.e., the use of antibiotics for MDR infections that are present but not yet diagnosed), analyses will be repeated with antibiotic intensity reclassified based on receipt of antibiotics initiated 24, 48, or 72 hours prior to MDR infection. If the hazard for MDR infection is driven only be recently received antibiotics, then it will be taken to signify protopathic bias and an additional model will be generated without ICU antibiotics.

(3) Antibiotic class-specific exposures. Testing will be performed for relevant antibiotic-organism combinations including beta-lactam antibiotic exposure and subsequent MRSA infection, vancomycin exposure and subsequent VRE infection, beta-lactam and extended-spectrum cephalosporin exposure and subsequent ESBL infection, and carbepenem exposure and subsequent CRE infection.

(4) MDR versus non-MDR infections. We will evaluate how MDR and non-MDR infections differ by repeating the final model comparing risk factors for MDR vs non-MDR infections, and also by comparing risk factors for all infections (MDR or non-MDR) vs no infections.

All statistical testing will be performed within STATA 14 (StataCorp, College Station, Tex.) two-sided with an alpha of 0.05 unless otherwise specified.

Sample Size and Power.

Rates of MDR infections are common in VA ICUs, as they are in all ICUs. During a successful 2007-2010 nationwide VA MRSA prevention effort covering 196 medical, coronary care, and surgical ICUs that reported data, incidence rates for ICU-acquired MDR infections were 0.6% for MRSA and 0.5% for VRE.[135] Importantly, this data does not include highly resistant Gram negative infections which now may account for over 65% of ICU-acquired MDR infections.[136] Extrapolating from CDC data regarding current prevalence of MDR Gram negative infections, we anticipate an additional 30-day incidence rate for ICU-acquired MDR Gram negative infections of 1.9%.[137] Overall, we conservatively estimate 133,000 unique ICU admissions annually with a cumulative incidence rate of 3% MDR infections. Over the 6 years covered by Aim 2, this will translate into an anticipated sample size of 797,000 including 23,910 ICU-acquired MDR infections. This sample size will yield 80% power to detect a relative difference of 4.9% in rates of MDR infection between any two quartiles of antibiotic use and 90% power to detect a relative difference of 5.7% in rates of MDR infection (two-sided Mantel-Haenszel test) while also providing excellent power for subgroup and additional analyses.

Results will improve understanding of the risk factors for antibiotic-resistant infections in the ICU and will provide organism-specific rates of infections and the morbidity and mortality of infections by organism and site of infection. The risk factors that result from this study will delineate the population that will be targeted in future phase trials. This study will provide an improved understanding regarding the time course of antibiotic-resistant infections and the duration of therapy. This research will prevent antibiotic resistant infections in critically ill or otherwise at-risk patients.

The widespread use of broad-spectrum antibiotics has contributed to the proliferation of MDR organisms. However, critically ill patients frequently require initial empiric therapy with broad-spectrum antibiotics in the setting of sepsis or to prevent infections in certain high-risk scenarios. These patients are at high risk for colonization and infection with MDR organism, which also increases the risk of spread of these highly-resistant pathogens in healthcare settings. We have demonstrated that critically ill patients suffer a marked loss of key protective bacteria in the gut that prevent the proliferation of major pathogens including MDR bacteria. Exposure to broad spectrum antibiotics in these patients results in large increases in antibiotic resistance genes within the gut. Select prebiotic therapies have the potential to preserve these protective bacteria and limit the spread of antimicrobial resistance in critical illness.

We propose a phase 1/2 randomized, placebo-controlled trial to assess the safety and efficacy of the prebiotic inulin in critically ill patients. We will assess whether inulin reduces the expansion of antimicrobial resistance in gut bacteria. We will also identify risk factors for MDR infections in critically ill patients. We will use the VA Informatics and Computing Infrastructure (VINCI), a specialized on-line portal designed for analysis of VA electronic medical records data, to determine the characteristics of individuals who would potentially derive the greatest benefit from interventions aimed at limiting the spread of antimicrobial resistance.

The Centers for Disease Control has identified antimicrobial resistance as one of the top public health threats[144], highlighting the potentially broad impact of the proposed avenue of investigation. Prebiotics represent a simple, safe, and well-tolerated intervention that can potentially limit the spread and negative impact of antimicrobial resistance, and can be easily administered.

REFERENCES

1. Neidell M J, Cohen B, Furuya Y, et al. Costs of healthcare- and community-associated infections with antimicrobial-resistant versus antimicrobial-susceptible organisms. *Clinical infectious diseases: an official publication of the Infectious Diseases Society of America.* 2012; 55(6):807-815.
2. National Nosocomial Infections Surveillance S. National Nosocomial Infections Surveillance (NNIS) System Report, data summary from January 1992 through June 2004, issued October 2004. *American journal of infection control.* 2004; 32(8):470-485.
3. Slayton R B, Toth D, Lee B Y, et al. Vital Signs: Estimated Effects of a Coordinated Approach for Action to Reduce Antibiotic-Resistant Infections in Health Care Facilities—United States. MMWR. *Morbidity and mortality weekly report.* 2015; 64(30):826-831.
4. Garrouste-Orgeas M, Timsit J F, Tafflet M, et al. Excess risk of death from intensive care unit-acquired nosocomial bloodstream infections: a reappraisal. *Clinical infectious diseases: an official publication of the Infectious Diseases Society of America.* 2006; 42(8):1118-1126.
5. Blot S, Koulenti D, Dimopoulos G, et al. Prevalence, risk factors, and mortality for ventilator-associated pneumonia in middle-aged, old, and very old critically ill patients*. *Crit Care Med.* 2014; 42(3):601-609.
6. Tabah A, Koulenti D, Laupland K, et al. Characteristics and determinants of outcome of hospital-acquired bloodstream infections in intensive care units: the EUROBACT International Cohort Study. *Intensive Care Med.* 2012; 38(12):1930-1945.
7. Kollef K E, Schramm G E, Wills A R, Reichley R M, Micek S T, Kollef M H. Predictors of 30-day mortality and hospital costs in patients with ventilator-associated pneumonia attributed to potentially antibiotic-resistant gram-negative bacteria. *Chest.* 2008; 134(2):281-287.
8. Albrecht M C, Griffith M E, Murray C K, et al. Impact of *Acinetobacter* infection on the mortality of burn patients. *Journal of the American College of Surgeons.* 2006; 203(4):546-550.
9. Petersen K, Riddle M S, Danko J R, et al. Trauma-related infections in battlefield casualties from Iraq. *Annals of surgery.* 2007; 245(5):803-811.
10. Lloyd B A, Murray C K, Shaikh F, et al. Early infectious outcomes following addition of fluoroquinolone or aminoglycoside to post-trauma antibiotic prophylaxis in combat-related open fracture injuries. The journal of trauma and acute care surgery. 2017.
11. Yun H C, Murray C K. Infection Prevention in the Deployed Environment. U.S. Army Medical Department journal. 2016(2-16):114-118.
12. Scott P, Deye G, Srinivasan A, et al. An outbreak of multidrug-resistant *Acinetobacter baumannii-calcoaceticus* complex infection in the US military health care system associated with military operations in Iraq. *Clinical infectious diseases: an official publication of the Infectious Diseases Society of America.* 2007; 44(12): 1577-1584.
13. Hospenthal D R, Crouch H K. Infection control challenges in deployed U S military treatment facilities. *The Journal of trauma.* 2009; 66(4 Suppl):5120-128.
14. *Acinetobacter baumannii* infections among patients at military medical facilities treating injured U.S. service members, 2002-2004. MMWR. *Morbidity and mortality weekly report.* 2004; 53(45):1063-1066.
15. Morrill H J, Morton J B, Caffrey A R, et al. Antimicrobial Resistance of *Escherichia coli* Urinary Isolates in the Veterans Affairs Health Care System. *Antimicrobial agents and chemotherapy.* 2017; 61(5).
16. Fitzpatrick M A, Suda K J, Safdar N, et al. Changes in bacterial epidemiology and antibiotic resistance among veterans with spinal cord injury/disorder over the past 9 years. *J Spinal Cord Med.* 2017:1-9.
17. Sommer M O, Dantas G, Church G M. Functional characterization of the antibiotic resistance reservoir in the human microflora. *Science.* 2009; 325(5944):1128-1131.
18. Donskey C J. Antibiotic regimens and intestinal colonization with antibiotic-resistant gram-negative bacilli. *Clinical infectious diseases: an official publication of the Infectious Diseases Society of America.* 2006; 43 Suppl 2:S62-69.

19. Forsberg K J, Reyes A, Wang B, Selleck E M, Sommer M O, Dantas G. The shared antibiotic resistome of soil bacteria and human pathogens. *Science.* 2012; 337(6098): 1107-1111.
20. Britton R A, Young V B. Role of the intestinal microbiota in resistance to colonization by *Clostridium difficile.* Gastroenterology. 2014; 146(6):1547-1553.
21. Leung V, Vincent C, Edens T, Miller M, Manges A R. Antimicrobial resistance gene acquisition and depletion following fecal microbiota transplantation (FMT) for recurrent *Clostridium difficile* infection. *Clinical infectious diseases: an official publication of the Infectious Diseases Society of America.* 2017.
22. Zaborin A, Smith D, Garfield K, et al. Membership and behavior of ultra-low-diversity pathogen communities present in the gut of humans during prolonged critical illness. *MBio.* 2014; 5(5):e01361-01314.
23. Shimizu K, Ogura H, Hamasaki T, et al. Altered gut flora are associated with septic complications and death in critically ill patients with systemic inflammatory response syndrome. *Dig Dis Sci.* 2011; 56(4):1171-1177.
24. Filius P M, Gyssens I C, Kershof I M, et al. Colonization and resistance dynamics of gram-negative bacteria in patients during and after hospitalization. *Antimicrobial agents and chemotherapy.* 2005; 49(7):2879-2886.
25. Lankelma J M, van Vught L A, Belzer C, et al. Critically ill patients demonstrate large interpersonal variation in intestinal microbiota dysregulation: a pilot study. *Intensive Care Med.* 2017; 43(1):59-68.
26. O'Keefe S J, Li J V, Lahti L, et al. Fat, fibre and cancer risk in African Americans and rural Africans. *Nat Commun.* 2015; 6:6342.
27. Atarashi K, Tanoue T, Oshima K, et al. Treg induction by a rationally selected mixture of Clostridia strains from the human microbiota. *Nature.* 2013; 500(7461):232-236.
28. Desai M S, Seekatz A M, Koropatkin N M, et al. A Dietary Fiber-Deprived Gut Microbiota Degrades the Colonic Mucus Barrier and Enhances Pathogen Susceptibility. *Cell.* 2016; 167(5):1339-1353 e1321.
29. Kaiko G E, Stappenbeck T S. Host-microbe interactions shaping the gastrointestinal environment. *Trends Immunol.* 2014; 35(11):538-548.
30. Morowitz M J, Di Caro V, Pang D, et al. Dietary Supplementation With Nonfermentable Fiber Alters the Gut Microbiota and Confers Protection in Murine Models of Sepsis. *Crit Care Med.* 2017; 45(5):e516-e523.
31. Riviere A, Selak M, Lantin D, Leroy F, De Vuyst L. Bifidobacteria and Butyrate-Producing Colon Bacteria: Importance and Strategies for Their Stimulation in the Human Gut. *Front Microbiol.* 2016; 7:979.
32. Dewulf E M, Cani P D, Claus S P, et al. Insight into the prebiotic concept: lessons from an exploratory, double blind intervention study with inulin-type fructans in obese women. *Gut.* 2013; 62(8):1112-1121.
33. Monk J M, Lepp D, Zhang C P, et al. Diets enriched with cranberry beans alter the microbiota and mitigate colitis severity and associated inflammation. *J Nutr Biochem.* 2016; 28:129-139.
34. Vaishnava S, Yamamoto M, Severson K M, et al. The antibacterial lectin RegIIIgamma promotes the spatial segregation of microbiota and host in the intestine. *Science.* 2011; 334(6053):255-258.
35. Cani P D, Possemiers S, Van de Wiele T, et al. Changes in gut microbiota control inflammation in obese mice through a mechanism involving GLP-2-driven improvement of gut permeability. *Gut.* 2009; 58(8):1091-1103.
36. Antunes L C, McDonald J A, Schroeter K, et al. Antivirulence activity of the human gut metabolome. *MBio.* 2014; 5(4):e01183-01114.
37. Fukuda S, Toh H, Hase K, et al. Bifidobacteria can protect from enteropathogenic infection through production of acetate. *Nature.* 2011; 469(7331):543-547.
38. Furusawa Y, Obata Y, Fukuda S, et al. Commensal microbe-derived butyrate induces the differentiation of colonic regulatory T cells. *Nature.* 2013; 504(7480):446-450.
39. Ramirez-Farias C, Slezak K, Fuller Z, Duncan A, Holtrop G, Louis P. Effect of inulin on the human gut microbiota: stimulation of *Bifidobacterium adolescentis* and *Faecalibacterium prausnitzii. Br J Nutr.* 2009; 101(4):541-550.
40. Tap J, Furet J P, Bensaada M, et al. Gut microbiota richness promotes its stability upon increased dietary fibre intake in healthy adults. *Environ Microbiol.* 2015; 17(12): 4954-4964.
41. Alfa M J, Strang D, Tappia P S, et al. A randomized trial to determine the impact of a digestion resistant starch composition on the gut microbiome in older and mid-age adults. *Clin Nutr.* 2017.
42. Terry M A, Freedberg D E, Morris M C. An Alternative Consent Process for Minimal Risk Research in the ICU. *Crit Care Med.* 2017.
43. McDonald D, Ackermann G, Khailova L, et al. Extreme Dysbiosis of the Microbiome in Critical Illness. *mSphere.* 2016; 1(4).
44. Hayakawa M, Asahara T, Henzan N, et al. Dramatic changes of the gut flora immediately after severe and sudden insults. *Dig Dis Sci.* 2011; 56(8):2361-2365.
45. Taur Y, Jenq R R, Perales M A, et al. The effects of intestinal tract bacterial diversity on mortality following allogeneic hematopoietic stem cell transplantation. *Blood.* 2014; 124(7):1174-1182.
46. Coyte K Z, Schluter J, Foster K R. The ecology of the microbiome: Networks, competition, and stability. *Science.* 2015; 350(6261):663-666.
47. Taur Y, Xavier J B, Lipuma L, et al. Intestinal domination and the risk of bacteremia in patients undergoing allogeneic hematopoietic stem cell transplantation. *Clinical infectious diseases: an official publication of the Infectious Diseases Society of America.* 2012; 55(7):905-914.
48. Ubeda C, Taur Y, Jenq R R, et al. Vancomycin-resistant *Enterococcus* domination of intestinal microbiota is enabled by antibiotic treatment in mice and precedes bloodstream invasion in humans. *J Clin Invest.* 2010; 120(12):4332-4341.
49. Zimmerman J E, Kramer A A, McNair D S, Malila F M. Acute Physiology and Chronic Health Evaluation (APACHE) I V: hospital mortality assessment for today's critically ill patients. *Crit Care Med.* 2006; 34(5):1297-1310.
50. Caballero S, Kim S, Carter R A, et al. Cooperating Commensals Restore Colonization Resistance to Vancomycin-Resistant *Enterococcus faecium. Cell Host Microbe.* 2017; 21(5):592-602 e594.
51. Yamada T, Shimizu K, Ogura H, et al. Rapid and Sustained Long-Term Decrease of Fecal Short-Chain Fatty Acids in Critically Ill Patients With Systemic Inflammatory Response Syndrome. *JPEN J Parenter Enteral Nutr.* 2015; 39(5):569-577.
52. Freedberg D E, Toussaint N C, Chen S P, et al. Proton Pump Inhibitors Alter Specific Taxa in the Human Gastrointestinal Microbiome: A Crossover Trial. *Gastroenterology.* 2015; 149(4):883-885 e889.
53. Joe A K, Schnoll-Sussman F, Bresalier R S, et al. Phase Ib Randomized, Double-Blinded, Placebo-Controlled, Dose Escalation Study of Polyphenon E in Patients with Barrett's Esophagus. *Cancer Prev Res (Phila).* 2015; 8(12): 1131-1137.
54. Scholvinck D W, Kunzli H T, Kestens C, et al. Treatment of Barrett's esophagus with a novel focal cryoablation device: a safety and feasibility study. *Endoscopy.* 2015; 47(12):1106-1112.
55. Sharma P, Meining A R, Coron E, et al. Real-time increased detection of neoplastic tissue in Barrett's esophagus with probe-based confocal laser endomicroscopy: final results of an international multicenter, prospective, randomized, controlled trial. *Gastrointest Endosc.* 2011; 74(3):465-472.
56. Gonzalez S, Yu W M, Smith M S, et al. Randomized comparison of 3 different-sized biopsy forceps for quality of sampling in Barrett's esophagus. *Gastrointest Endosc.* 2010; 72(5):935-940.
57. Greenwald B D, Dumot J A, Horwhat J D, Lightdale C J, Abrams J A. Safety, tolerability, and efficacy of endoscopic low-pressure liquid nitrogen spray cryotherapy in the esophagus. *Dis Esophagus.* 2010; 23(1):13-19.
58. Tramontano A C, Sheehan D F, Yeh J M, et al. The Impact of a Prior Diagnosis of Barrett's Esophagus on Esophageal Adenocarcinoma Survival. *Am J Gastroenterol.* 2017; 112(8):1256-1264.
59. Wani S, Muthusamy V R, Shaheen N J, et al. Development of quality indicators for endoscopic eradication therapies in Barrett's esophagus: the TREAT-BE (Treatment with Resection and Endoscopic Ablation Techniques for Barrett's Esophagus) Consortium. *Gastrointest Endosc.* 2017; 86(1):1-17 e13.
60. Sun X, Elston R C, Barnholtz-Sloan J S, et al. Predicting Barrett's Esophagus in Families: An Esophagus Translational Research Network (BETRNet) Model Fitting Clinical Data to a Familial Paradigm. *Cancer Epidemiol Biomarkers Prev.* 2016; 25(5):727-735.
61. Small A J, Araujo J L, Leggett C L, et al. Radiofrequency Ablation Is Associated With Decreased Neoplastic Progression in Patients With Barrett's Esophagus and Confirmed Low-Grade Dysplasia. *Gastroenterology.* 2015; 149(3):567-576 e563; quiz e513-564.
62. Abrams J A, Appelman H D, Beer D G, et al. Barrett's Esophagus Translational Research Network (BETRNet): the pivotal role of multi-institutional collaboration in esophageal adenocarcinoma research. *Gastroenterology.* 2014; 146(7):1586-1590.
63. Jackson M A, Goodrich J K, Maxan M E, et al. Proton pump inhibitors alter the composition of the gut microbiota. *Gut.* 2016; 65(5):749-756.
64. Cohen M E, Hathway J M, Salmasian H, et al. Prophylaxis for Stress Ulcers With Proton Pump Inhibitors Is Not Associated With Increased Risk of Bloodstream Infections in the Intensive Care Unit. *Clin Gastroenterol Hepatol.* 2017; 15(7):1030-1036 e1031.
65. Knox J, Sullivan S B, Urena J, et al. Association of Environmental Contamination in the Home With the Risk for Recurrent Community-Associated, Methicillin-Resistant *Staphylococcus aureus* Infection. *JAMA Intern Med.* 2016; 176(6):807-815.
66. Uhlemann A C, Dordel J, Knox J R, et al. Molecular tracing of the emergence, diversification, and transmission of *S. aureus* sequence type 8 in a New York community. *Proc Natl Acad Sci USA.* 2014; 111(18):6738-6743.
67. Uhlemann A C, McAdam P R, Sullivan S B, et al. *Evolutionary Dynamics of Pandemic* Methicillin-Sensitive *Staphylococcus aureus* ST398 and Its International Spread via Routes of Human Migration. *MBio.* 2017; 8(1).
68. Macesic N, Green D, Wang Z, et al. Detection of mcr-1-Carrying *Escherichia coli* Causing Bloodstream Infection in a New York City Hospital: Avian Origins, Human Concerns? *Open Forum Infect Dis.* 2017; 4(3): ofx115.
69. Satlin M J, Chen L, Patel G, et al. Multicenter Clinical and Molecular Epidemiological Analysis of Bacteremia Due to Carbapenem-Resistant Enterobacteriaceae (CRE) in the CRE Epicenter of the United States. Antimicrobial agents and chemotherapy. 2017; 61(4).
70. McConville T H, Sullivan S B, Gomez-Simmonds A, Whittier S, Uhlemann A C. Carbapenem-resistant Enterobacteriaceae colonization (CRE) and subsequent risk of infection and 90-day mortality in critically ill patients, an observational study. *PloS one.* 2017; 12(10):e0186195.
71. Cheng L, Nelson B C, Mehta M, et al. Piperacillin-Tazobactam versus Other Antibacterial Agents for Treatment of Bloodstream Infections Due to AmpC beta-Lactamase-Producing Enterobacteriaceae. *Antimicrobial agents and chemotherapy.* 2017; 61(6).
72. Pereira M R, Scully B F, Pouch S M, et al. Risk factors and outcomes of carbapenem-resistant *Klebsiella pneumoniae* infections in liver transplant recipients. *Liver Transpl.* 2015; 21(12):1511-1519.
73. Agarwalla A, Weber A, Davey S, et al. Lactulose Is Associated With Decreased Risk of *Clostridium difficile* Infection in Decompensated Cirrhosis. *Clin Gastroenterol Hepatol.* 2017; 15(6):953-954.
74. Hennessy S, Bilker W B, Leonard C E, et al. Observed association between antidepressant use and pneumonia risk was confounded by comorbidity measures. *J Clin Epidemiol.* 2007; 60(9):911-918.
75. Sarkar M, Hennessy S, Yang Y X. Proton-pump inhibitor use and the risk for community-acquired pneumonia. *Ann Intern Med.* 2008; 149(6):391-398.
76. Beitler J R, Link N, Bails D B, Hurdle K, Chong D H. Reduction in hospital-wide mortality after implementation of a rapid response team: a long-term cohort study. *Crit Care.* 2011; 15(6):R269.
77. Sevransky J E, Checkley W, Herrera P, et al. Protocols and Hospital Mortality in Critically Ill Patients: The United States Critical Illness and Injury Trials Group Critical Illness Outcomes Study. *Crit Care Med.* 2015; 43(10):2076-2084.
78. Wunsch H, Wagner J, Herlim M, Chong D H, Kramer A A, Halpern S D. ICU occupancy and mechanical ventilator use in the United States. *Crit Care Med.* 2013; 41(12):2712-2719.
79. Singer M, Deutschman C S, Seymour C W, et al. The Third International Consensus Definitions for Sepsis and Septic Shock (Sepsis-3). *JAMA.* 2016; 315(8):801-810.
80. Vincent J L, Moreno R, Takala J, et al. The SOFA (Sepsis-related Organ Failure Assessment) score to describe organ dysfunction/failure. On behalf of the Working Group on Sepsis-Related Problems of the European Society of Intensive Care Medicine. *Intensive Care Med.* 1996; 22(7):707-710.
81. Vincent J L, de Mendonca A, Cantraine F, et al. Use of the SOFA score to assess the incidence of organ dysfunc- 81. tion/failure in intensive care units: results of a multicenter, prospective study. Working group on "sepsis-related problems" of the European Society of Intensive Care Medicine. *Crit Care Med.* 1998; 26(11):1793-1800.
82. Ferreira F L, Bota D P, Bross A, Melot C, Vincent J L. Serial evaluation of the SOFA score to predict outcome in critically ill patients. *JAMA.* 2001; 286(14):1754-1758.
83. Bone R C, Balk R A, Cerra F B, et al. Definitions for sepsis and organ failure and guidelines for the use of innovative therapies in sepsis. The ACCP/SCCM Consensus Conference Committee. American College of Chest Physicians/Society of Critical Care Medicine. *Chest.* 1992; 101(6):1644-1655.
84. Hotchkiss R S, Monneret G, Payen D. Sepsis-induced immunosuppression: from cellular dysfunctions to immunotherapy. *Nat Rev Immunol.* 2013; 13(12):862-874.
85. Churpek M M, Zadravecz F J, Winslow C, Howell M D, Edelson D P. Incidence and Prognostic Value of the Systemic Inflammatory Response Syndrome and Organ Dysfunctions in Ward Patients. *Am J Respir Crit Care Med.* 2015; 192(8):958-964.
86. (CLSI) CaLSI. Performance standards for antimicrobial susceptibility testing. *CLSI Supplement M100.* 2017(27th Ed.).
87. Baggs J, Fridkin S K, Pollack L A, Srinivasan A, Jernigan J A. Estimating National Trends in Inpatient Antibiotic Use Among US Hospitals From 2006 to 2012. *JAMA Intern Med.* 2016; 176(11):1639-1648.
88. Cadot P, Kochuyt A M, van Ree R, Ceuppens J L. Oral allergy syndrome to chicory associated with birch pollen allergy. *Int Arch Allergy Immunol.* 2003; 131(1):19-24.
89. Lecerf J M, Depeint F, Clerc E, et al. Xylo-oligosaccharide (XOS) in combination with inulin modulates both the intestinal environment and immune status in healthy subjects, while XOS alone only shows prebiotic properties. *Br J Nutr.* 2012; 108(10):1847-1858.
90. Bonnema A L, Kolberg L W, Thomas W, Slavin J L. Gastrointestinal tolerance of chicory inulin products. *J Am Diet Assoc.* 2010; 110(6):865-868.
91. Garcia-Peris P, Velasco C, Lozano M A, et al. Effect of a mixture of inulin and fructo-oligosaccharide on *Lactobacillus* and *Bifidobacterium* intestinal microbiota of patients receiving radiotherapy: a randomised, double-blind, placebo-controlled trial. *Nutr Hosp.* 2012; 27(6): 1908-1915.
92. O'Keefe S J, Ou J, Delany J P, et al. Effect of fiber supplementation on the microbiota in critically ill patients. *World J Gastrointest Pathophysiol.* 2011; 2(6): 138-145.
93. Knight D J, Gardiner D, Banks A, et al. Effect of synbiotic therapy on the incidence of ventilator associated pneumonia in critically ill patients: a randomised, double-blind, placebo-controlled trial. *Intensive Care Med.* 2009; 35(5):854-861.
94. Kotzampassi K, Giamarellos-Bourboulis E J, Voudouris A, Kazamias P, Eleftheriadis E. Benefits of a synbiotic formula (Synbiotic 2000Forte) in critically Ill trauma patients: early results of a randomized controlled trial. *World J Surg.* 2006; 30(10):1848-1855.
95. Majid H A, Cole J, Emery P W, Whelan K. Additional oligofructose/inulin does not increase faecal bifidobacteria in critically ill patients receiving enteral nutrition: a randomised controlled trial. *Clin Nutr.* 2014; 33(6):966-972.
96. Dilli D, Aydin B, Zenciroglu A, Ozyazici E, Beken S, Okumus N. Treatment outcomes of infants with cyanotic congenital heart disease treated with synbiotics. *Pediatrics.* 2013; 132(4):e932-938.
97. Thurlow C J, Prabaker K, Lin M Y, et al. Anatomic sites of patient colonization and environmental contamination with *Klebsiella pneumoniae* carbapenemase-producing Enterobacteriaceae at long-term acute care hospitals. *Infection control and hospital epidemiology.* 2013; 34(1): 56-61.
98. Ray A J, Pultz N J, Bhalla A, Aron D C, Donskey C J. Coexistence of vancomycin-resistant enterococci and *Staphylococcus aureus* in the intestinal tracts of hospitalized patients. *Clinical infectious diseases: an official publication of the Infectious Diseases Society of America.* 2003; 37(7):875-881.
99. Klotz M, Zimmermann S, Opper S, Heeg K, Mutters R. Possible risk for re-colonization with methicillin-resistant *Staphylococcus aureus* (MRSA) by faecal transmission. *International journal of hygiene and environmental health.* 2005; 208(5):401-405.
100. Acton D S, Plat-Sinnige M J, van Wamel W, de Groot N, van Belkum A. Intestinal carriage of *Staphylococcus aureus*: how does its frequency compare with that of nasal carriage and what is its clinical impact? *Eur J Clin Microbiol Infect Dis.* 2009; 28(2):115-127.
101. Bhalla A, Aron D C, Donskey C J. *Staphylococcus aureus* intestinal colonization is associated with increased frequency of S. aureus on skin of hospitalized patients. *BMC Infect Dis.* 2007; 7:105.
102. Dangerfield B, Chung A, Webb B, Seville M T. Predictive value of methicillin-resistant *Staphylococcus aureus* (MRSA) nasal swab PCR assay for MRSA pneumonia. *Antimicrobial agents and chemotherapy.* 2014; 58(2):859-864.
103. Sinha R, Chen J, Amir A, et al. Collecting Fecal Samples for Microbiome Analyses in Epidemiology Studies. *Cancer Epidemiol Biomarkers Prev.* 2015.
104. Walker A W, Martin J C, Scott P, Parkhill J, Flint H J, Scott K P. 16S rRNA gene-based profiling of the human infant gut microbiota is strongly influenced by sample processing and PCR primer choice. *Microbiome.* 2015; 3:26.
105. Bonten M J, Nathan C, Weinstein R A. Recovery of nosocomial fecal flora from frozen stool specimens and rectal swabs: comparison of preservatives for epidemiological studies. *Diagnostic microbiology and infectious disease.* 1997; 27(4):103-106.
106. Turnbaugh P J, Ley R E, Hamady M, Fraser-Liggett C M, Knight R, Gordon J I. The human microbiome project. *Nature.* 2007; 449(7164):804-810.
107. Teasdale G, Jennett B. Assessment of coma and impaired consciousness. A practical scale. *Lancet.* 1974; 2(7872):81-84.
108. Faleck D M, Salmasian H, Furuya E Y, Larson E L, Abrams J A, Freedberg D E. Proton Pump Inhibitors Do Not Increase Risk for *Clostridium difficile* Infection in the Intensive Care Unit. *Am J Gastroenterol.* 2016; 111(11): 1641-1648.
109. Freedberg D E, Salmasian H, Cohen B, Abrams J A, Larson E L. Receipt of Antibiotics in Hospitalized Patients and Risk for *Clostridium difficile* Infection in Subsequent Patients Who Occupy the Same Bed. *JAMA Intern Med.* 2016; 176(12):1801-1808.
110. Faleck D M S H, Furuya Y E, Larson E L, Abrams J A, Freedberg D E. Risk Factors for ICU-Onset *Clostridium difficile* Infection. *Am J Resp Crit Care Med* (submitted).
111. Patel S J, Oliveira A P, Zhou J J, et al. Risk factors and outcomes of infections caused by extremely drug-resistant gram-negative bacilli in patients hospitalized in intensive care units. *American journal of infection control.* 2014; 42(6):626-631.
112. Spadafino J T, Cohen B, Liu J, Larson E. Temporal trends and risk factors for extended-spectrum beta-lactamase-producing *Escherichia coli* in adults with catheter-associated urinary tract infections. Antimicrob Resist Infect Control. 2014; 3(1):39.
113. Jeon C Y, Muennig P, Furuya E Y, Cohen B, Nash D, Larson E L. Burden of present-on-admission infections and health care-associated infections, by race and ethnicity. *American journal of infection control.* 2014; 42(12): 1296-1302.
114. Fosbrink M, Wilt G, Chen L, Kreisworth B, Devgan V. Identification of antibiotic resistance genes in *Klebsiella pneumoniae* isolates and metagenomic samples using real-time PCR arrays. Sample to Insight, accessed on-line at https://www.slideshare.net/QIAGENscience/identification-of-antibiotic-resistance-genes-in-klebsiella-pneumoniae-isolates-and-metagenomic-samples-using-reallime-pcr-arrays. Apr. 6, 2016.
115. Rocha D J, Santos C S, Pacheco L G. Bacterial reference genes for gene expression studies by RT-qPCR: survey and analysis. *Antonie Van Leeuwenhoek.* 2015; 108(3):685-693.
116. Klindworth A, Pruesse E, Schweer T, et al. Evaluation of general 16S ribosomal RNA gene PCR primers for classical and next-generation sequencing-based diversity studies. *Nucleic Acids Res.* 2013; 41(1):e1.
117. Janssen M F, Pickard A S, Golicki D, et al. Measurement properties of the EQ-5D-5L compared to the EQ-5D-3L across eight patient groups: a multi-country study. *Qual Life Res.* 2013; 22(7):1717-1727.
118. Herdman M, Gudex C, Lloyd A, et al. Development and preliminary testing of the new five-level version of EQ-5D (EQ-5D-5L). *Qual Life Res.* 2011; 20(10):1727-1736.
119. Needham D M, Sepulveda K A, Dinglas V D, et al. Core Outcome Measures for Clinical Research in Acute Respiratory Failure Survivors: An International Modified Delphi Consensus Study. *Am J Respir Crit Care Med.* 2017.
120. Dinglas V D, Chessare C M, Davis W E, et al. Perspectives of survivors, families and researchers on key outcomes for research in acute respiratory failure. *Thorax.* 2017.
121. Katz S, Downs T D, Cash H R, Grotz R C. Progress in development of the index of ADL. *Gerontologist.* 1970; 10(1):20-30.
122. Schandl A, Bottai M, Holdar U, Hellgren E, Sackey P. Early prediction of new-onset physical disability after intensive care unit stay: a preliminary instrument. *Crit Care.* 2014; 18(4):455.
123. Gumpert H, Kubicek-Sutherland J Z, Porse A, et al. Transfer and Persistence of a Multi-Drug Resistance Plasmid in situ of the Infant Gut Microbiota in the Absence of Antibiotic Treatment. *Front Microbial.* 2017; 8:1852.
124. McDonald D, Price M N, Goodrich J, et al. An improved Greengenes taxonomy with explicit ranks for ecological and evolutionary analyses of bacteria and archaea. *ISME J.* 2012; 6(3):610-618.
125. Segata N, Izard J, Waldron L, et al. Metagenomic biomarker discovery and explanation. *Genome Biol.* 2011; 12(6):R60.
126. U.S. Department of Veterans Affairs HSRD. Spotlight: Preventing Healthcare Associated Infections. Accessed on-line at https://www.hsrd.research.va.gov/news/feature/preventing_infections.cfm on Oct. 11, 2017. 2013.
127. Thaden J T, Lewis S S, Hazen K C, et al. Rising rates of carbapenem-resistant enterobacteriaceae in community hospitals: a mixed-methods review of epidemiology and microbiology practices in a network of community hospitals in the southeastern United States. *Infection control and hospital epidemiology.* 2014; 35(8):978-983.
128. Harrell F E, Jr., Shih Y C. Using full probability models to compute probabilities of actual interest to decision makers. *Int J Technol Assess Health Care.* 2001; 17(1): 17-26.
129. (CLSI) CaLSI. Performance standards for antimicrobial susceptibility testing. *CLSI Supplement M*100. 2017 (27th Ed.).
130. Magiorakos A P, Srinivasan A, Carey R B, et al. Multidrug-resistant, extensively drug-resistant and pan-drug-resistant bacteria: an international expert proposal for interim standard definitions for acquired resistance. *Clinical microbiology and infection: the official publication of the European Society of Clinical Microbiology and Infectious Diseases.* 2012; 18(3):268-281.
131. Charlson M E, Pompei P, Ales K L, MacKenzie C R. A new method of classifying prognostic comorbidity in longitudinal studies: development and validation. *Journal of chronic diseases.* 1987; 40(5):373-383.
132. Salmasian H, Freedberg D E, Friedman C. Deriving comorbidities from medical records using natural language processing. *Journal of the American Medical Informatics Association: JAMIA.* 2013; 20(e2):e239-242.
133. Grambsch P M, Therneau T M. Proportional hazards tests and diagnostics based on weighted residuals. *Biometrika.* 1994; 81:515-526.
134. Fine J P, Gray R J. A proportional hazards model for the subdistribution of a competing risk. *Journal of the American Statistical Association.* 1999; 94(446):496-509.
135. Jain R, Kralovic S M, Evans M E, et al. Veterans Affairs initiative to prevent methicillin-resistant *Staphylococcus aureus* infections. *N Engl J Med.* 2011; 364(15):1419-1430.
136. Chelazzi C, Pettini E, Villa G, De Gaudio A R. Epidemiology, associated factors and outcomes of ICU-acquired infections caused by Gram-negative bacteria in critically ill patients: an observational, retrospective study. *BMC Anesthesiol.* 2015; 15:125.
137. Prevention CfDCa. Antibiotic Resistance Threats in the United States. Accessed on-line at https://www.cdc.gov/drugresistance/pdf/ar-threats-2013-508.pdf on Oct. 12, 2017. 2013.
138. Khan N, Patel D, Shah Y, Yang Y X. Factors Predicting Testing and Treatment of Iron Deficiency in a Nationwide Cohort of Anemic U C Patients. *Inflamm Bowel Dis.* 2016; 22(12):2894-2901.
139. Cohen M E, Salmasian H, Li J V, et al. Surgical Antibiotic Prophylaxis is not Associated with Risk for Post-Operative Antibiotic-Resistant Infections. *J Am College of Surgeons.* 2017; Epub Oct. 16, 2017, print pending.
140. Rubin M, Evans C, Perencevich E. Combating Antimicrobial Resistance through Rapid Implementation of Available Guidelines and Evidence (CARRIAGE). 2017; https://www.queri.research.va.gov/programs/carriage.cfm. Accessed Jun. 30, 2017.
141. Rubin M. QUERI National Program Network: Combating Antimicrobial Resistance through Rapid Implementation of Available Guidelines and Evidence (CARRIAGE). Accessed on-line Oct. 10, 2017. 2017.

142. Antibiotic resistance threats in the United States, 2013. 2013; https://www.cdc.gov/drugresistance/threat-report-2013/index.html. Accessed Sep. 21, 2017.
143. Review of Antimicrobial Stewardship Programs in Veterans Healthcare Administration Facilities. 2016; https://www.va.gov/oig/pubs/VAOIG-15-04247-111.pdf. Accessed Jun. 30, 2017.
144. Antibiotic Resistance Solutions Initiative. 2017; https://www.cdc.gov/drugresistance/solutions-initiative/index.html. Accessed Sep. 21, 2017.

Example 3 Inulin for the Prevention of Antibiotic Resistant Infection or Pathogen Colonization in the Intensive Care Unit Chicory-derived inulin will be used to prevent antibiotic-resistant infections in the intensive care unit or in other populations at high risk for such infections. The prebiotic fiber inulin is a non-digestible plant-derived polysaccharide and is a key nutrient source for beneficial short-chain fatty acid (SCFA)-producing bacteria that live in the human colon. In animals and humans, inulin increases gut SCFA content, induces bacteriocin production, and improves gut barrier function. The hypothesis is that inulin supplementation in critically ill patients will result in higher levels of SCFA-producing Clostridia, which in turn will decrease gastrointestinal pathogen colonization and lower risk for multidrug resistant bacterial infections. Inulin has been studied extensively in humans, including critically ill humans, and appears safe and well tolerated.
Formulation of the Dosage Forms to be Used.
Inulin will be obtained as a highly soluble powder (CAS-No. 9005-80-05, EC-No. 232-684-3) which will be reconstituted as a liquid by dissolution in 250 mL of sterile water.
Route of Administration.
Oral.
Objectives and Duration of the Proposed Clinical Investigation(s).
This pilot (Phase 1/2) clinical trial will test inulin for the purpose of preventing antibiotic-resistant infections in the intensive care unit. Thirty critically ill adults with sepsis will be block randomized 1:1:1 to inulin 16 g/day, inulin 32 g/day, or placebo. Inulin or placebo will be given for 7 days in 2 divided doses and subjects will be followed for 30 days or until hospital discharge, with telephone follow-up conducted up to 6 months after the intervention. The primary objectives of the trial are to test feasibility (enrollment rate, protocol adherence, and intervention fidelity), safety, and the impact of inulin on gastrointestinal antibiotic resistance, which will be assessed as the cumulative antibiotic resistance within colonizing gut bacteria. The approximate duration of this proposed investigation is 3.5 years.
Inulin is safe and has been studied extensively in humans. Foods such as agave, banana, chicory, garlic, and onions are high in inulin. Reported side effects include abdominal bloating, most likely from the gaseous products of colonic bacterial metabolism of inulin. In a total of 7 published ICU-based trials including 1,030 subjects testing inulin alone or in combination there were no serious adverse events.[1-7] One trial involving premature infants in the NICU reported self-resolving feeding intolerance in 4 patients.[7] In a total of 12 published trials including 511 subjects testing inulin alone or in combination there were no serious adverse events.[1-12] Four of the 12 trials reported one or more subjects with abdominal bloating although in no cases were there any clinical consequences as a result of the bloating.[8-11] Non-inulin dietary fibers have also been studied extensively in the ICU and the experience of these trials is also relevant for this application. In a total of 5 ICU-based trials including 265 subjects testing non-inulin dietary fibers there were no serious adverse events.[13-17] One trial reported 3 subjects with abdominal bloating and another reported increased average gastric residual volumes in patients who received enteral feeding and fiber.[14] To summarize, in a total of 24 trials including 1,806 subjects there were no serious adverse events reported related to inulin. Several studies did report symptomatic bloating as a result of inulin.
Rationale.
Antibiotic resistance in the ICU is a problem of the human gastrointestinal microbiome, the critical reservoir for the bacteria and plasmids that encode antibiotic resistance genes. The normal gut microbiota prevents colonization and subsequent infection with MDR organisms through competition for resources and other mechanisms. In critical illness, normal colonization resistance is lost; there are no currently available therapies to prevent loss of gut colonization resistance and subsequent proliferation of MDR organisms. Specific gut bacteria are key to colonization resistance. ICU patients have low levels of butyrate and other short chain fatty acids (SCFAs) derived from dietary fiber by colonic anaerobes, primarily within Clostridia Clusters IV and XIVa. SCFAs moderate colonic inflammation, enlarge the pool of regulatory T cells, and contribute to defense from pathogens. During critical illness, SCFA-producing bacteria and SCFAs are depleted. Our data show that proliferation of vancomycin-resistant *Enterococcus* and other pathogens occurs in the setting of diminished colonization resistance and loss of SCFA-producing bacteria. The prebiotic fiber inulin is a non-digestible polysaccharide and is a key nutrient source for these beneficial SCFA-producing bacteria. In animals and humans, inulin increases gut SCFA content, induces bacteriocin production, and improves gut barrier function. We hypothesize that inulin supplementation in ICU patients will result in higher levels of SCFA-producing Clostridia, which in turn will decrease gastrointestinal pathogen colonization and lower risk for MDR infections. This hypothesis will be tested in a pilot study of 30 critically ill adults who will be randomized 1:1:1 to inulin at 2 doses or placebo.
Indication to be Studied.
The planned indications are as follows:
To limit colonization with antibiotic-resistant bacteria in critically ill patients; and
To prevent antibiotic-resistant infections acquired in the intensive care unit.
General Approach for Evaluation of Treatment.
This pilot study will randomize critically ill adults 1:1:1 to inulin 16 g/day, inulin 32 g/day, or placebo for 7 days. Study assessments will be made on days 0, 3, 7, and 30 with telephone follow-up after 3 and 6 months. The primary objective of the pilot study is to demonstrate feasibility and the primary outcome will be the within-individual change in cumulative antibiotic resistance in the colonizing gut bacteria on day 7, comparing the inulin and the placebo arms of the study. Demonstration of feasibility will lead to larger/later phase trials with clinical outcomes related to antibiotic-resistant infections.
Description of First Year Trial(s).
We plan to enroll no fewer than 10 subjects during the first 12-month period of active enrollment.
Number of Subjects to be Evaluated.
The enrollment goal will be 30 subjects over 36 months.
Chemistry, Manufacturing and Control Information.
Chicory-derived inulin is available from a number of commercial manufacturing facilities in compliance with Good Manufacturing Practice (GMP). The investigational product will be supplied by Sigma-Aldrich.

Previous Human Experience.

To arrive at the proposed dosing for inulin, we referenced (1) previous human trials involving inulin and (2) previous ICU-based trials involving non-inulin fibers. Previous human trials involving inulin have used doses up to 16 g/day for 3 months without serious adverse effects.[8] Previous ICU-based trials involving non-inulin fibers have used doses up to 32 g/day for 5 weeks without serious adverse events.[15] Based on these results and on the fact that inulin, as a dietary supplement, has an excellent expected safety profile, we selected to test doses of 16 g/day and 32 g/day for 7 days split into 2 divided doses. Inulin-type prebiotics are generally recognized as safe.

REFERENCES

1. Dilli D, Aydin B, Fettah N D, et al. The propre-save study: effects of probiotics and prebiotics alone or combined on necrotizing enterocolitis in very low birth weight infants. *J Pediatr.* 2015; 166(3):545-551 e541.
2. Dilli D, Aydin B, Zenciroglu A, Ozyazici E, Beken S, Okumus N. Treatment outcomes of infants with cyanotic congenital heart disease treated with synbiotics. *Pediatrics.* 2013; 132(4):e932-938.
3. Knight D J, Gardiner D, Banks A, et al. Effect of synbiotic therapy on the incidence of ventilator associated pneumonia in critically ill patients: a randomised, double-blind, placebo-controlled trial. *Intensive Care Med.* 2009; 35(5):854-861.
4. Kotzampassi K, Giamarellos-Bourboulis E J, Voudouris A, Kazamias P, Eleftheriadis E. Benefits of a synbiotic formula (Synbiotic 2000Forte) in critically Ill trauma patients: early results of a randomized controlled trial. *World J Surg.* 2006; 30(10):1848-1855.
5. Majid H A, Cole J, Emery P W, Whelan K. Additional oligofructose/inulin does not increase faecal bifidobacteria in critically ill patients receiving enteral nutrition: a randomised controlled trial. *Clin Nutr.* 2014; 33(6):966-972.
6. Simakachorn N, Bibiloni R, Yimyaem P, et al. Tolerance, safety, and effect on the faecal microbiota of an enteral formula supplemented with pre- and probiotics in critically ill children. *J Pediatr Gastroenterol Nutr.* 2011; 53(2):174-181.
7. Underwood M A, Salzman N H, Bennett S H, et al. A randomized placebo-controlled comparison of 2 prebiotic/probiotic combinations in preterm infants: impact on weight gain, intestinal microbiota, and fecal short-chain fatty acids. *J Pediatr Gastroenterol Nutr.* 2009; 48(2):216-225.
8. Dewulf E M, Cani P D, Claus S P, et al. Insight into the prebiotic concept: lessons from an exploratory, double blind intervention study with inulin-type fructans in obese women. *Gut.* 2013; 62(8):1112-1121.
9. Lecerf J M, Depeint F, Clerc E, et al. Xylo-oligosaccharide (XOS) in combination with inulin modulates both the intestinal environment and immune status in healthy subjects, while XOS alone only shows prebiotic properties. *Br J Nutr.* 2012; 108(10):1847-1858.
10. Bonnema A L, Kolberg L W, Thomas W, Slavin J L. Gastrointestinal tolerance of chicory inulin products. *J Am Diet Assoc.* 2010; 110(6):865-868.
11. Garcia-Peris P, Velasco C, Lozano M A, et al. Effect of a mixture of inulin and fructo-oligosaccharide on *Lactobacillus* and *Bifidobacterium* intestinal microbiota of patients receiving radiotherapy: a randomised, double-blind, placebo-controlled trial. *Nutr Hosp.* 2012; 27(6):1908-1915.
12. Tovar A R, Caamano Mdel C, Garcia-Padilla S, Garcia O P, Duarte M A, Rosado J L. The inclusion of a partial meal replacement with or without inulin to a calorie restricted diet contributes to reach recommended intakes of micronutrients and decrease plasma triglycerides: a randomized clinical trial in obese Mexican women. *Nutr J.* 2012; 11:44.
13. Alfa M J, Strang D, Tappia P S, et al. A randomized trial to determine the impact of a digestion resistant starch composition on the gut microbiome in older and mid-age adults. *Clin Nutr.* 2017.
14. Karakan T, Ergun M, Dogan I, Cindoruk M, Unal S. Comparison of early enteral nutrition in severe acute pancreatitis with prebiotic fiber supplementation versus standard enteral solution: a prospective randomized double-blind study. *World J Gastroenterol.* 2007; 13(19):2733-2737.
15. O'Keefe S J, Ou J, Delany J P, et al. Effect of fiber supplementation on the microbiota in critically ill patients. World J Gastrointest Pathophysiol. 2011; 2(6):138-145.
16. Spapen H, Diltoer M, Van Malderen C, Opdenacker G, Suys E, Huyghens L. Soluble fiber reduces the incidence of diarrhea in septic patients receiving total enteral nutrition: a prospective, double-blind, randomized, and controlled trial. Clin Nutr. 2001; 20(4):301-305.
17. Spindler-Vesel A, Bengmark S, Vovk I, Cerovic O, Kompan L. Synbiotics, prebiotics, glutamine, or peptide in early enteral nutrition: a randomized study in trauma patients. *JPEN J Parenter Enteral Nutr.* 2007; 31(2):119-126.

Example 4 The Relationship Between Dietary Fiber Intake and Short Chain Fatty Acid-Producing Bacteria During Critical Illness: A Prospective Cohort Study Objectives:

Dietary fiber increases short chain fatty acid (SCFA)-producing bacteria in ambulatory patients yet is often withheld in the intensive care unit (ICU). This study evaluated the safety and effect of fiber in ICU patients with sampling of the gut microbiome at ICU admission and after 72 hours.

Patients:

Consecutive adults 18 years or older newly admitted to an ICU at tertiary medical center in New York City between 2016 and 2017. Patients who were nil per os (NPO), enterally fed, or taking food by mouth were all eligible.

Measurements:

Rectal swabs were performed at ICU admission and 72 hours later. The primary exposure was fiber intake over 72 hours, classified in tertiles and corrected for caloric intake. The primary outcome was the relative abundance (RA) of SCFA producers based on 16S rRNA sequencing.

Main Results:

In 129 ICU patients, median fiber intake was 13.4 g (IQR 0-35.4 g) over 72 hours or 27.3 g (IQR 11.6-39.3 g) excluding patients who were NPO. Baseline RA of SCFA producers at ICU admission was similar across fiber intake groups. After 72 hours in the ICU, median RA of SCFA producers was 0.40%, 0.50%, and 1.8% for patients with no, low, and high fiber intake respectively ($p=0.05$). After correcting for total caloric intake, the median RA of SCFA producers was 0.41%, 0.32% and 2.35% for patients in the corrected no, low and high fiber categories (p<0.01 for trend). These associations remained significant after adjusting for other factors including antibiotics and acute severity of illness. There were no differences based on fiber intake in abdominal distension, nausea/vomiting, diarrhea, or other adverse events.

Conclusions:

During the 72 hours after ICU admission, higher fiber intake was well tolerated and was associated with higher levels of SCFA-producing bacteria.

Pre- and probiotics are being explored in the ICU in the hope that they will modify the gut microbiome to prevent multidrug-resistant (MDR) bacterial colonization and reduce healthcare-associated infections (HAIs). In a meta-analysis of randomized trials, probiotics showed benefit in preventing ventilation associated pneumonia and *Clostridioides difficile* infection in the ICU (1-3). However, probiotic trials have been heterogeneous in terms of both interventions and results, and some trials have suggested harm (2, 4, 5).

Dietary fiber is a prebiotic which increases the abundance of bacteria which produce butyrate and other short-chain fatty acids (SCFAs). These bacteria, or their metabolites, appear to have immunomodulatory benefits that are relevant for ICU patients (6-8). In bone marrow transplant recipients and select ICU cohorts, increased abundance of SCFA-producing bacteria was associated with decreased MDR organism colonization including decreased vancomycin-resistant *Enterococcus* (7, 9). In healthy volunteers and ambulatory patients, fiber is well tolerated and increases SCFA producer levels (10).

For these reasons, fiber may be an appropriate prebiotic to test in the ICU. However, concerns are often raised that fiber will increase bloating and contribute to diarrhea during critical illness (11, 12). Rare cases of bezoars and intestinal obstruction have been reported. Guidelines emphasize the selective use of fiber for diarrhea rather than for all ICU patients (13). In clinical practice, ICU patients often receive fiber-free enteral formulations. Overall, it is uncertain whether ICU patients who receive broad-spectrum antibiotics, mechanical ventilation, and other interventions will respond to dietary fiber in the same manner as healthy volunteers or ambulatory patients.

This study was conducted to assess the relationship between dietary fiber on SCFA-producing bacteria within the gastrointestinal microbiome of ICU patients, and also to assess its tolerability. Fiber intake and clinical factors were measured within a cohort of ICU patients whose gut microbiota was serially sampled.

Methods

Population.

This was a retrospective study nested within a longitudinal, prospective ICU-based cohort. (7) In brief, adults 18 years old or more were eligible for the study if they were newly admitted to any one of 5 distinct medical or surgical ICUs and could be reached within 4 hours of ICU admission. Rectal swabs were performed at the time of ICU admission and 72 hours later (±4 hours), and clinical data was gathered. The study focused on the 72-hour window following ICU admission because of prior data indicating that interventions occurring early during critical illness are disproportionately important in patient outcome. (14) Patients who were nil per os (NPO), who received enteral nutrition, or who took food by mouth were all included provided that their nutritional intake was clearly recorded and calculable. Patients were excluded if the 72-hour study assessment could not be completed due to death, discharge, or patient refusal. Informed consent was obtained from all subjects or from appropriate surrogates. (15)

Fiber Intake.

The primary exposure was total fiber intake from the time of ICU admission when the first sample was taken until 72 hours later when the second sample was taken. Fiber intake was measured by manually extracting data from electronic nursing flow sheets. For patients receiving enteral feeds, the type of feed, its nutritional values, the hourly infusion rate and the duration of infusion were collected. Interruptions of feeding were recorded to the hour by the nursing staff. Fiber intake over the 72-hour period was then calculated by multiplying the total volume of feeds by the amount of fiber per unit. For patients taking food by mouth, the type of meals, number of meals and percentage of meal consumption as recorded by the patient's nurse were extracted from the electronic orders and the nursing flow sheets. Nutritional values for each meal type were obtained from the Department of Nutrition, including the fiber content of that meal. In the participating ICUs, nurses visually inspect the meal tray after each mealtime and record the percentage of each meal consumed in quartiles. Short-term withholding of meals (e.g., before procedures) was also accounted for. The amount of fiber intake over the 72-hour period was then calculated as number of meals received multiplied by the percentage of meal consumption and by the amount of fiber contained in each meal and analyzed in tertiles or as a continuous measure.

Other Nutritional Intake.

Total caloric intake was calculated in a similar fashion as fiber intake. A patient-specific calorie target was calculated by a registered clinical dietician using the Mifflin-St. Jeor equation and the Penn State University 2003b and 2010 equations, taking into consideration age, body mass index, ventilation status, and comorbidities as recommended by American Society of Parenteral and Enteral Nutrition (ASPEN) guidelines. (16) The actual caloric intake over the 72 hour period was then divided by total calorie target to obtain the percentage of target calories received. The amount of fiber consumed depends on total caloric consumption so, to explore the possibility that relative consumption of fiber was a determinant of fecal microbial composition, a calorie-corrected "fiber index" was calculated. The fiber index was defined as fiber intake over the 72-hour period divided by the percentage of calorie target received.

Short Chain Fatty Acid-Producing Bacteria.

The primary outcome was the relative abundance of SCFA-producing bacteria after 72 hours in the ICU based on 16S rRNA gene sequencing results from the 72-hour rectal swab. This was defined as the sum total of the relative abundance of the following taxa within Clostridial Clusters IV/XIVa, with all taxa specified at the lowest possible hierarchical level: *Faecalibacterium prausnitzii*, *Eubacterium rectale*, Ruminococcus, *Blautia*, *Coprococcus*, and *Roseburia* (6-8). Sequencing data is available in the short-read archive section of the National Center for Biotechnology Information (accession number SRP149563).

Gastrointestinal Microbiome.

An untargeted hierarchical linear discriminant analysis (LDA) effect size algorithm (LEfSe) (17) was used with sequencing results to identify altered taxa based on fiber intake. Additionally, *Enterococcus* relative abundance was pre-specified as a secondary outcome of interest within the gastrointestinal microbiome because our previous study identified it as an independent predictor of death and infection in the ICU study (18). Standard microbiome alpha diversity measures (Shannon and Chao index) were assessed, also based on 16S rRNA gene sequencing.

Co-Variables.

Demographic information, laboratory data, and data related to ICU interventions was extracted from the electronic medical record. Baseline comorbidities were recorded including immunosuppression and sepsis as the admitting diagnosis. ICU interventions were recorded including proton pump inhibitors, mechanical ventilation, vasopressor support and hemodialysis (either intermittent or continuous). Antibiotic use (any dose or duration) was recorded and divided into narrow- and broad-spectrum based on previous studies reporting the extent of antibiotic disruption to the gut microbiota (19-22). For clinical data, the following data was extracted: presence of edema on physical exam, abdominal distention, nausea/vomiting (either by symptoms recorded in the physician's notes or the administration of antiemetic agents), diarrhea, bowel obstruction confirmed by radiography, history of gastrointestinal surgery, and severe malnutrition as diagnosed by a clinical nutritionist. Clinical and laboratory data were used to estimate acute severity of illness as the Acute Physiologic Assessment and Chronic Health Evaluation (APACHE IV) score (23).

Statistical Analysis.

Comparisons of clinical data were performed using Fisher's exact test or a chi-squared tests for categorical data. T tests or rank-sum tests were used for continuous variables. For multiple groups, analysis of variance (ANOVA) or Kruskal-Wallis tests were used. To assess the independent effect of fiber after adjusting for additional exposures, a non-parametric least squares regression model was constructed for the outcome of relative abundance of SCFA producers (24, 25). Exposure variables were included in this model if they had an independent relationship with SCFA producer level (p<0.10). Alpha was 0.05 for all analyses unless otherwise specified.

16S rRNA Gene Sequencing.

Methods for collecting rectal swabs and for 16S rRNA gene sequencing have been previously described. (49) In brief, deep rectal swabs were performed using a flocked nylon swab (Copan Diagnostics). Swabs were inserted into the anal canal with the patient in the left lateral decubitus position until there was fecal soilage. Swabs were flash frozen at −80° C. for batched DNA extraction at the end of the study (PowerFecal, MoBio, Carlsbad, Calif.). Polymerase chain reaction was performed targeting the V4 hypervariable region of the 16S ribosomal RNA gene with primers derived from the human microbiome project (50-52) on the Illumina HiSeq 4000 platform (Illumina, San Diego, Calif.). Greengenes (53) was used as a reference database with clustering of taxonomic units made at 97% sequence similarity and final analysis via the QIIME pipeline. (54)

Results

Population

A total of 178 patients were enrolled in the original study cohort including 142 who completed both study assessments and were considered for this study (36 patients died or refused the second sample collection). An additional thirteen patients were excluded because there was insufficiently detailed dietary information recorded in the nursing flowsheets, leaving 129 patients who were analyzed.

Fiber Intake

Median fiber intake during the 72 hours after ICU admission was 13.4 g (IQR 0-35.4 g). Excluding patients who received no fiber, the median fiber intake was 27.3 g (IQR 11.6-39.3 g). Patients who received more fiber were less acutely ill (lower APACHE IV scores) and less likely to receive broad-spectrum antibiotics (Table 10). They also had a higher total caloric intake and attained a higher percentage of goal calories (Table 11). There were no differences in gastrointestinal events based on fiber intake category including no difference in bowel obstruction, nausea or vomiting, enteric infections, edema, or diarrhea (Table 12). Patients with higher fiber intake were less likely to have abdominal distension (11% high fiber vs 4% low fiber vs 28% no fiber, chi-squared p<0.01).

Fiber Index

Total fiber intake tends to be correlated with total caloric intake, so a fiber index was calculated to assess the impact of fiber on the gut microbiome after correcting for total caloric intake Like high fiber patients, high fiber index patients were less acutely ill and less likely to receive broad-spectrum antibiotics compared to low fiber index patients, although these differences were less marked compared to total fiber intake (Table 13).

Fiber Intake and SCFA Producing Bacteria

Figure 8A:
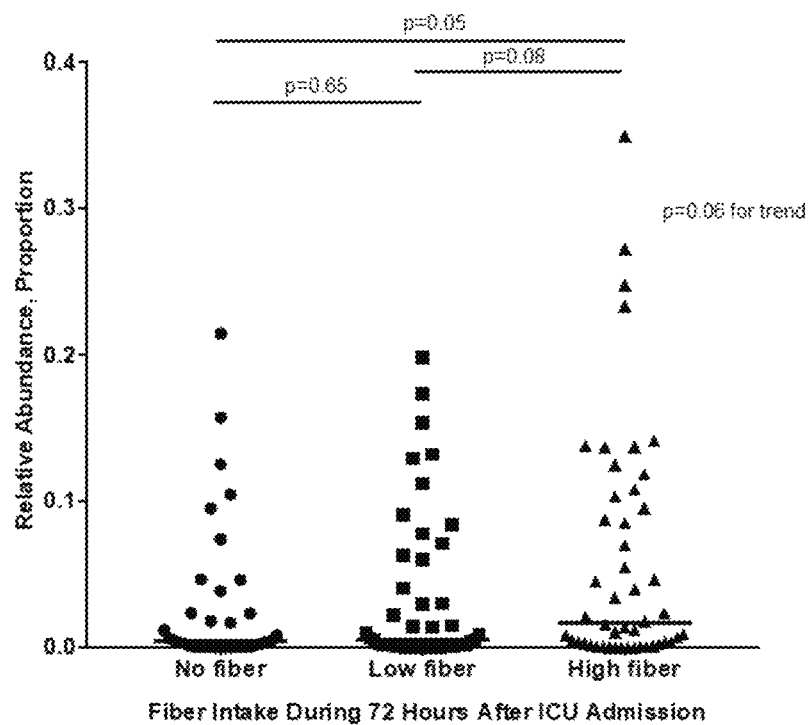
FIGS. 8A-8B. Relative abundance of short chain fatty acid-producing bacteria 72 hours after ICU admission. This is shown stratified by (A) fiber intake and (B) fiber index during the 72 hours after ICU admission.
Figure 8B:
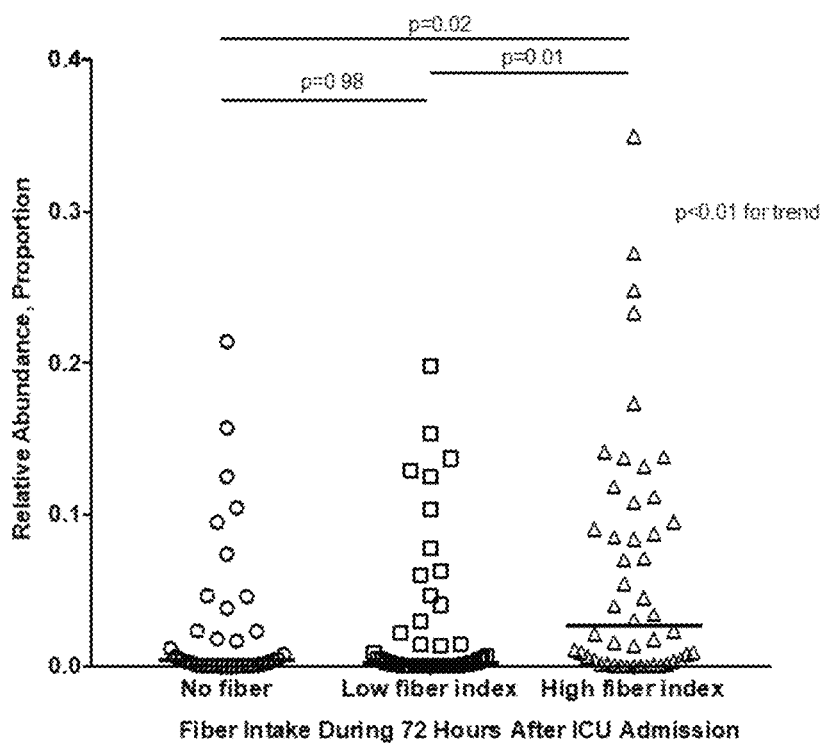
Figure 10:
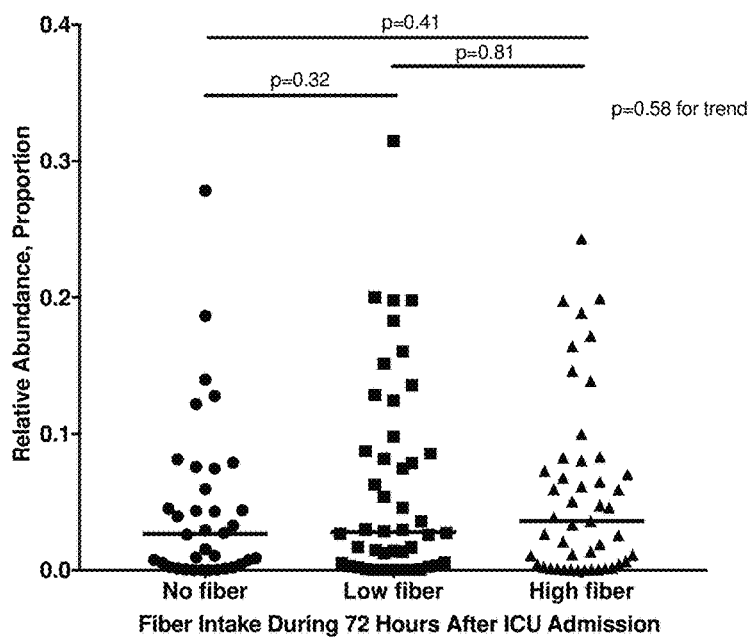
FIG. 10. Relative abundance of short chain fatty acid-producing bacteria at the time of ICU admission, stratified by subsequent fiber intake over 72 hours.

The median relative abundance of SCFA producers was 2.8% (IQR 0.42-7.9%) at the time of ICU admission and 0.80% (IQR 0.062-6.3%) 72 hours later (median change −0.33%, Wilcoxon p=0.02). Relative abundance of SCFA producers was similar at ICU admission across fiber intake categories (FIG. 10). After 72 hours, higher levels of SCFA producers were seen in patients with higher fiber intake (median 1.8% high fiber vs 0.40% no fiber, FIG. 8A). Results were similar based on calorie-corrected fiber index rather than fiber intake (FIG. 8B).

Gastrointestinal Microbiome

Figure 9A:
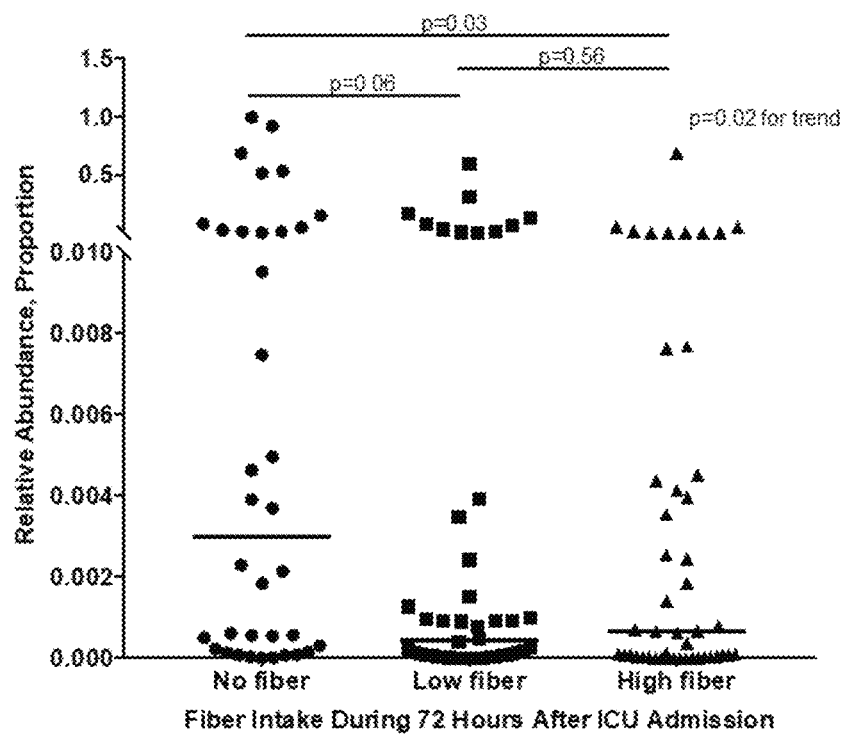
FIGS. 9A-9B. Relative abundance of *Enterococcus* 72 hours after ICU admission. This is shown stratified by (A) fiber intake and (B) fiber index during the 72 hours after ICU admission.
Figure 9B:
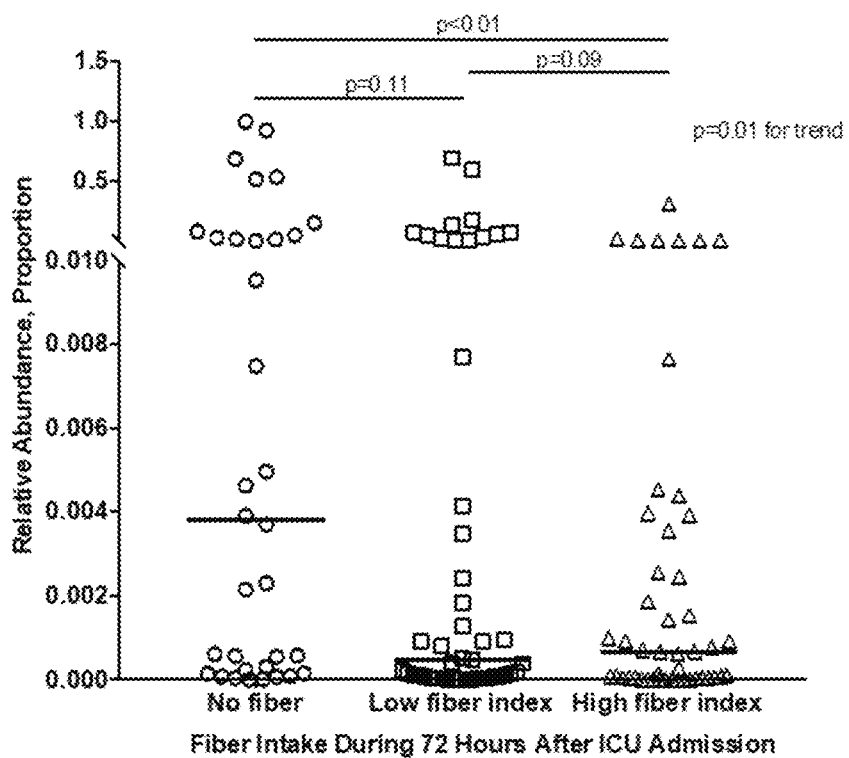

An untargeted algorithm (LEfSe) was used to test for differences in the relative abundance across all bacterial taxa based on fiber intake. The SCFA producers *Blautia* (4.0-fold difference) and *F. prausnitzii* (3.9-fold difference) were among 7 taxa that were enriched in the high fiber group compared to the no fiber group. *Enterococcus* (4.8-fold difference) was the only taxon that was enriched in the no fiber group compared to the high fiber group. Comparing the high fiber group to the low fiber group, *Blautia* was among 3 taxa that were enriched in the high fiber group (3.7-fold difference). Median relative abundance of *Enterococcus* was 0.0076% at ICU admission (IQR 0.0016-0.13%) and 0.070% (IQR 0.0072-0.77%) 72 hours later (median change 0.010%, Wilcoxon p<0.01). Higher fiber intake associated with lower abundance of *Enterococcus* after 72 hours (median 0.066% high fiber vs 0.30% no fiber, FIG. 9A). Results were similar based on fiber index rather than fiber intake (FIG. 9B).

Figure 11A:
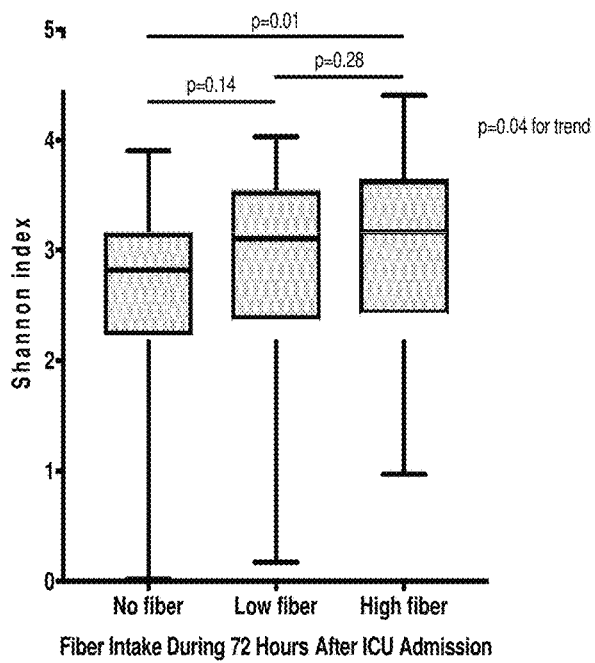
FIGS. 11A-11B. (A) Fecal bacterial diversity (Shannon index) and (B) fecal bacterial richness (Chao) 72 hours after ICU admission, stratified by fiber intake during the 72 hours after ICU admission.
Figure 11B:
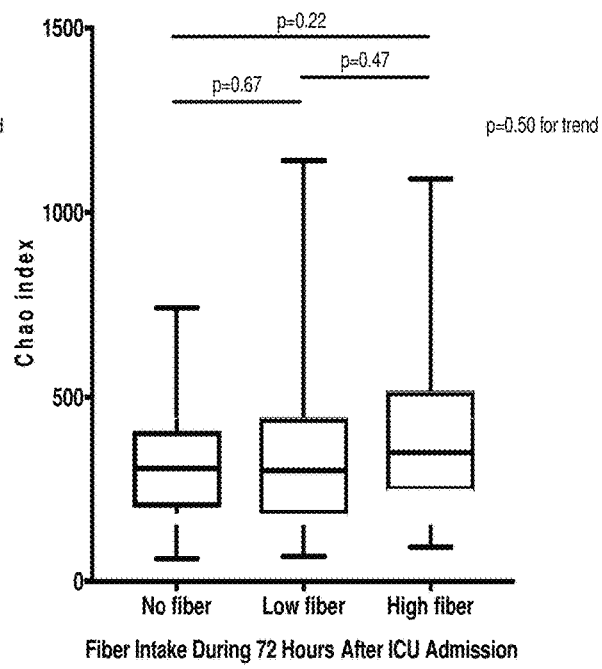

The diversity and richness of the gut microbiota was analyzed using the Shannon and Chao indices. Over the 72-hour study period, there was a significant within-individual decline in Shannon diversity (median −0.20, 95% CI −0.34 to −0.063, p<0.01) and Chao richness (median −26, 95% CI −48 to −3.7, p=0.02). Higher fiber intake was associated with higher fecal microbial diversity at 72 hours yet not richness (p=0.04 and 0.50 respectively, FIGS. 11A and 11B). A similar result was seen based on fiber index (data not shown).

Multivariable Model

In a multivariable model, higher fiber intake remained associated with higher relative abundance of SCFA producers after adjusting for antibiotics, admission APACHE IV score, and exposure to mechanical ventilation or use of vasopressors (Table 14). There was a 0.30% median increase in SCFA producers after 72 hours per additional 10 g of fiber intake (p<0.01).

Discussion

In 129 critically ill patients sampled at the time of ICU admission and 72 hours later, higher fiber intake was associated with higher levels of SCFA-producing bacteria. Fiber intake was not associated with adverse gastrointestinal events including diarrhea. The association between fiber intake and SCFA producers was seen even though 77% of the study cohort received antibiotics and even after accounting for acute severity of illness. The association also remained even after correcting as much as possible for the fact that patients with a lower caloric intake also inevitably had a lower fiber intake.

Considerable efforts are being expended to develop prebiotics or probiotics suitable for critically ill patients. SCFA producers are among the leading targets for such therapies, and therefore the results of this study provide encouraging data that dietary fiber—a simple, inexpensive treatment—may promote the growth of beneficial gut microorganisms in the ICU.

The timing and the density of caloric delivery in the ICU has been studied extensively, usually with disappointing results. Multiple randomized controlled trials (RCTs) have shown negligible clinical differences between early versus late enteral nutrition, and between calorie-dense versus calorie-sparse feeding strategies (26-31). Comparatively few studies have examined the specific effects of dietary fiber. In 15 patients receiving chronic enteral nutrition, fiber had little impact on SCFA producers yet increased the SCFAs including acetate and butyrate (32). Interestingly, fiber was associated with decreased levels of *Enterococcus*, similar to this study. Another RCT involving 22 critically ill patients found no increase in levels of SCFA producers after a low (7 g) daily dose of fiber, although the study failed to meet its enrollment target (33).

While ICU studies are conflicting, ambulatory studies have consistently shown that fiber supplementation increases SCFA producer levels. In two placebo-controlled studies, fiber was associated with a doubling of *F. prausnitzii* and other SCFA-producers and concurrent decreases in candidate biomarkers for infection such as serum C-reactive protein (CRP) and lipopolysaccharide (LPS) (34, 35). In another placebo-controlled study, the fiber arm had higher post-treatment total SCFA levels and butyrate levels, lower circulating LPS concentrations, and decreased gene expressions of pro-inflammatory cytokines in whole blood (36). In this study, the associations between higher fiber intake and SCFA producer level were large in magnitude, with 4-fold higher *F. prausnitzii* and *Blautia* in the highest compared to the lowest fiber intake group. Future investigations should test whether these changes were also associated with biomarkers like CRP or LPS.

Animal studies and data from ambulatory patients suggest that increased SCFA levels may have clinical benefits that are relevant for ICU patients (7). In animals, SCFA producers confer colonization resistance against common enteric pathogens including vancomycin-resistant *Enterococcus* (VRE) (37-41). This study also observed an inverse relationship between SCFA producers and *Enterococcus*. In addition to higher SCFA producers, dietary fiber intake was associated with improved fecal microbial diversity. Diversity within the microbiome may be a surrogate for colonization resistance against VRE or other pathogens. In ICU patients, fecal microbial diversity tends to be low on admission and to decline with prolonged hospitalization (42). In bone marrow transplant recipients, low diversity and low SCFA producer levels prior to transplant have been associated with VRE bacteremia, respiratory infections, and increased risk for death (6, 9, 43, 44).

Historically, fiber has often been withheld in the ICU for fear of diarrhea or bowel obstruction. This study showed no difference in gastrointestinal-related side effects in patients with high fiber intake, although there were relatively few gastrointestinal events overall. To date, there are no reports of serious adverse effects due to soluble fiber in the ICU (45). In a dose-ranging study, ICU patients received open-label wheat dextran for 5 weeks at doses up to 36 g/day with good tolerance (46). Patients had higher SCFA-producers and fecal SCFAs seen comparing post-versus pre-fiber. Like these studies, this study provides reassurance given the concerns occasionally raised regarding prebiotics in patients with altered small bowel or colonic motility (47, 48).

There are several strengths to our study. It is one of the first to explore the effect of a specific dietary component in critically ill patients. A rigorous protocol was implemented for sample collection and fiber intake measurement. A broad range of clinical data was collected to ensure comprehensive analysis and to control for important differences between patient groups, including use of antibiotics and acute severity of illness.

In sum, in this ICU-based cohort study fiber intake during the initial 72 hours in the ICU was not associated with gastrointestinal intolerance and was correlated with higher levels of SCFA-producing bacteria, even after adjusting for antibiotics and acute severity of illness. SCFA-producing bacteria have been associated with health benefits in animals and humans, including improved colonization resistance against enteric pathogens. Fiber may be a simple therapy for critically ill patients, and can modulate the gut microbiome to confer benefit in ICU patients.

TABLE 10

Baseline and ICU characteristics, stratified by fiber intake.

| Characteristics (n, %) | No fiber (n = 36) | Low fiber (n = 46) | High fiber (n = 47) | p-value |
|---|---|---|---|---|
| Baseline | | | | |
| Female sex | 17 (47) | 21 (48) | 19 (40) | 0.51 |
| Age | | | | 0.09 |
| <60 | 14 (39) | 12 (26) | 21 (45) | |
| 60-70 | 10 (28) | 24 (52) | 13 (28) | |
| >70 | 12 (33) | 10 (22) | 13 (28) | |
| ICU type | | | | 0.23 |
| Medical | 21 (58) | 20 (43) | 28 (60) | |
| Surgical | 15 (42) | 26 (57) | 19 (40) | |
| Immunosuppression | 6 (30) | 4 (42) | 8 (39) | 0.44 |
| Kidney disease | 6 (13) | 7 (15) | 9 (19) | 0.72 |
| Diabetes | 16 (34) | 16 (34) | 14 (30) | 0.38 |
| Pulmonary disease | 3 (6) | 2 (4) | 4 (8) | 0.49 |
| Intensive care unit | | | | |
| Sepsis | 16 (34) | 12 (26) | 7 (15) | <0.01 |
| APACHE IV score | | | | <0.01 |
| Lowest tertile (<45) | 7 (19) | 14 (30) | 25 (53) | |
| Medium tertile (45-70) | 9 (25) | 16 (35) | 12 (26) | |
| Highest tertile (>70) | 20 (56) | 16 (35) | 10 (21) | |
| Antibiotics | | | | 0.02 |
| None | 2 (6) | 10 (22) | 17 (36) | |
| Narrow-spectrum | 12 (33) | 10 (22) | 10 (21) | |
| Broad-spectrum | 22 (61) | 26 (56) | 20 (42) | |
| Proton pump inhibitors | 16 (44) | 22 (48) | 25 (53) | 0.72 |
| Mechanical ventilation | 14 (39) | 4 (9) | 3 (6) | <0.01 |
| Hemodialysis | 6 (17) | 3 (6) | 1 (2) | <0.01 |
| Vasopressors | 14 (30) | 8 (17) | 5 (11) | <0.01 |

TABLE 11

Nutrition during the 72 hours after ICU admission, stratified by fiber intake.

| Nutritional characteristics over 72 hours | No fiber (n = 36) | Low fiber (n = 46) | High fiber (n = 47) | p-value |
|---|---|---|---|---|
| Total fiber (median g, IQR) | 0.0 | 11.2 (3.8-18.2) | 39.3 (34.7-50.2) | <0.01 |
| (mean g, standard deviation) | 0.0 (0.0) | 11.0 (7.5) | 43.4 (13.2) | |
| Nutritional intake (n, %) | | | | <0.01 |
| NPO | 25 (69) | 0 | 0 | |
| Enteral feeds | 11 (31) | 3 (9) | 1 (2) | |
| By mouth | 0 | 43 (91) | 46 (98) | |
| Total calories (median kcal, IQR) | 0 (0-128) | 1082 (674-1574) | 3215 (2698-3769) | <0.01 |
| Target calories (median kcal, IQR) | 0.0% (0.0-2.4%) | 16.9% (9.9-27.2%) | 61.3% (46.2-71.7%) | <0.01 |
| Fiber index (median g/%, IQR) | 0.0 | 49.7 (28.9-76.0) | 74.0 (63.6-82.3) | <0.01 |
| Total protein (median g, IQR) | 0.0 (0.0-6.6) | 46.5 (6.3-68.7) | 153.5 (133.7-177.4) | <0.01 |
| Total fat (median g, IQR) | 0.0 (0.0-3.6) | 33.2 (4.7-54.6) | 105.7 (94.0-129.4) | <0.01 |
| Diagnosis of malnutrition (n, %) | 1 (2) | 2 (4) | 0 | 0.37 |

TABLE 12

Gastrointestinal events during the 72 hours after ICU admission, stratified by fiber intake.

| Gastrointestinal events (n, %) | No fiber (n = 36) | Low fiber (n = 46) | High fiber (n = 47) | p-value, high vs. no fiber | p-value, high vs. medium fiber |
|---|---|---|---|---|---|
| Abdominal distension | 13 (28) | 2 (4) | 5 (11) | <0.01 | <0.01 |
| High gastric residuals | 0 | 0 | 0 | | |
| Bowel obstruction | 0 | 0 | 0 | | |
| Nausea or vomiting | 8 (17) | 21 (45) | 21 (45) | 0.04 | 0.23 |
| Enteric infections | 2 (4) | 4 (9) | 0 | 0.18 | 0.69 |
| Edema | 10 (21) | 10 (21) | 12 (26) | >0.99 | 0.61 |
| Diarrhea | 6 (13) | 8 (17) | 7 (15) | >0.99 | >0.99 |

TABLE 13

Baseline and ICU characteristics, stratified by fiber index.

| Characteristics (n, %) | No fiber (n = 36) | Low fiber index (n = 46) | High fiber index (n = 47) | p-value |
|---|---|---|---|---|
| Baseline | | | | |
| Female sex | 17 (47) | 20 (44) | 15 (32) | 0.51 |
| Age | | | | 0.36 |
| <60 | 14 (39) | 14 (30) | 19 (40) | |
| 60-70 | 10 (28) | 22 (48) | 15 (32) | |
| >70 | 12 (33) | 10 (22) | 13 (28) | |
| ICU type | | | | 0.69 |
| Medical | 21 (58) | 25 (54) | 23 (49) | |
| Surgical | 15 (42) | 21 (46) | 24 (51) | |
| Immunosuppression | 6 (17) | 6 (13) | 8 (17) | 0.85 |
| Kidney disease | 6 (13) | 7 (15) | 9 (19) | 0.88 |
| Diabetes | 16 (44) | 11 (24) | 14 (30) | 0.13 |
| Pulmonary disease | 3 (6) | 1 (2) | 5 (11) | 0.26 |
| Intensive care unit | | | | |
| Sepsis | 16 (34) | 12 (26) | 5 (11) | <0.01 |
| APACHE IV score | | | | <0.01 |
| Lowest tertile (<45) | 7 (19) | 16 (35) | 23 (49) | |
| Medium tertile (45-70) | 9 (25) | 19 (41) | 9 (19) | |
| Highest tertile (>70) | 20 (56) | 11 (24) | 15 (32) | |
| Antibiotics | | | | <0.01 |
| None | 2 (6) | 10 (22) | 17 (36) | |
| Narrow-spectrum | 12 (33) | 8 (17) | 12 (26) | |
| Broad-spectrum | 22 (61) | 28 (61) | 18 (38) | |
| Proton pump inhibitors | 16 (44) | 25 (54) | 22 (47) | 0.63 |
| Mechanical ventilation | 14 (39) | 4 (9) | 3 (6) | <0.01 |
| Hemodialysis | 6 (17) | 4 (9) | 0 (0) | 0.02 |
| Vasopressors | 14 (30) | 8 (17) | 5 (11) | <0.01 |

TABLE 14

Multivariable model for relative abundance (RA) of short chain fatty acid (SCFA) producers after 72 hours in the ICU.

| Exposure Variables | Median Increase in RA of SCFA Producers | Estimate IQR | p-value |
|---|---|---|---|
| Fiber, per 10 g increase | +0.30% | +0.10 to +0.46% | <0.01 |
| Antibiotics | | | |
| None | Reference | — | — |
| Narrow-spectrum only | +1.0% | −2.4 to +4.4% | 0.56 |
| Broad-spectrum | −0.62% | −3.6 to +2.4% | 0.69 |
| APACHE IV score at admission, per 10-point increase | +0.27% | −0.15 to +0.69% | 0.21 |
| Mechanical ventilation | +0.40% | −3.1 to +3.9% | 0.82 |
| Vasopressors | −1.7% | −4.7 to +1.3% | 0.26 |

This kernel-based least squares regression model estimates the median independent effect of each exposure variable on the outcome of relative abundance of SCFA producers after 72 hours in the ICU. This model was selected because the relative abundance of SCFA producers is non-linear (left skewed) data. See text for additional details. IQR: interquartile range ($25^{th}$ to $75^{th}$ percentile).

REFERENCES

1. Goldenberg J Z, Yap C, Lytvyn L, et al. Probiotics for the prevention of *Clostridium difficile*-associated diarrhea in adults and children. Cochrane Database Syst Rev 2017; 12:CD006095.
2. Morrow L E, Kollef M H, Casale T B. Probiotic prophylaxis of ventilator-associated pneumonia: a blinded, randomized, controlled trial. Am J Respir Crit Care Med 2010; 182(8):1058-1064.
3. Shen N T, Maw A, Tmanova L L, et al. Timely Use of Probiotics in Hospitalized Adults Prevents *Clostridium difficile* Infection: A Systematic Review With Meta-Regression Analysis. Gastroenterology 2017; 152(8):1889-1900 e1889.
4. Boyle R J, Robins-Browne R M, Tang M L. Probiotic use in clinical practice: what are the risks? Am J Clin Nutr 2006; 83(6):1256-1264; quiz 1446-1257.

5. Hempel S, Newberry S, Ruelaz A, et al. Safety of probiotics used to reduce risk and prevent or treat disease. Evid Rep Technol Assess (Full Rep) 2011(200):1-645.
6. Haak B W, Littmann E R, Chaubard J L, et al. Impact of gut colonization with butyrate-producing microbiota on respiratory viral infection following allo-HCT. Blood 2018; 131(26):2978-2986.
7. Livanos A E, Snider E J, Whittier S, et al. Rapid gastrointestinal loss of Clostridial Clusters IV and XIVa in the ICU associates with an expansion of gut pathogens. PLoS One 2018; 13(8):e0200322.
8. Van den Abbeele P, Belzer C, Goossens M, et al. Butyrate-producing *Clostridium* cluster XIVa species specifically colonize mucins in an in vitro gut model. ISME J 2013; 7(5):949-961.
9. Taur Y, Jenq R R, Perales M A, et al. The effects of intestinal tract bacterial diversity on mortality following allogeneic hematopoietic stem cell transplantation. Blood 2014; 124(7):1174-1182.
10. Salonen A, Lahti L, Salojarvi J, et al. Impact of diet and individual variation on intestinal microbiota composition and fermentation products in obese men. ISME J 2014; 8(11):2218-2230.
11. Elia M, Engfer M B, Green C J, et al. Systematic review and meta-analysis: the clinical and physiological effects of fibre-containing enteral formulae. Aliment Pharmacol Ther 2008; 27(2):120-145.
12. Turza K C K J, Sawyer R G. Enteral feeding and vasoactive agents: suggested guidelines for clinicians. Pract Gastroenterol 2009(78):11-22.
13. McClave S A, Taylor B E, Martindale R G, et al. Guidelines for the Provision and Assessment of Nutrition Support Therapy in the Adult Critically Ill Patient: Society of Critical Care Medicine (SCCM) and American Society for Parenteral and Enteral Nutrition (A.S.P.E.N.). JPEN J Parenter Enteral Nutr 2016; 40(2):159-211.
14. Levy M M, Macias W L, Vincent J L, et al. Early changes in organ function predict eventual survival in severe sepsis. Crit Care Med 2005; 33(10):2194-2201.
15. Terry M A, Freedberg D E, Morris M C. An Alternative Consent Process for Minimal Risk Research in the ICU. Crit Care Med 2017; 45(9):1450-1456.
16. Gottschlich M M, DeLegge M H, Guenter P, et al. The A.S.P.E.N. nutrition support core curriculum: a case-based approach: the adult patient. Silver Spring, Md.: American Society for Parenteral and Enteral Nutrition; 2007.
17. Segata N, Izard J, Waldron L, et al. Metagenomic biomarker discovery and explanation. Genome Biol 2011; 12(6):R60.
18. Freedberg D E, Zhou M J, Cohen M E, et al. Pathogen colonization of the gastrointestinal microbiome at intensive care unit admission and risk for subsequent death or infection. Intensive Care Med 2018.
19. Dethlefsen L, Relman D A. Incomplete recovery and individualized responses of the human distal gut microbiota to repeated antibiotic perturbation. Proc Natl Acad Sci USA 2011; 108 Suppl 1:4554-4561.
20. Rea M C, Dobson A, O'Sullivan 0, et al. Effect of broad- and narrow-spectrum antimicrobials on *Clostridium difficile* and microbial diversity in a model of the distal colon. Proc Natl Acad Sci USA 2011; 108 Suppl 1:4639-4644.
21. Sullivan A, Edlund C, Nord C E. Effect of antimicrobial agents on the ecological balance of human microflora. Lancet Infect Dis 2001; 1(2):101-114.
22. Ubeda C, Taur Y, Jenq R R, et al. Vancomycin-resistant *Enterococcus* domination of intestinal microbiota is enabled by antibiotic treatment in mice and precedes bloodstream invasion in humans. J Clin Invest 2010; 120(12):4332-4341.
23. Zimmerman J E, Kramer A A, McNair D S, et al. Acute Physiology and Chronic Health Evaluation (APACHE) I V: hospital mortality assessment for today's critically ill patients. Crit Care Med 2006; 34(5):1297-1310.
24. Hainmueller J, Hazlett C. Kernel Regularized Least Squares: Reducing Misspecification Bias with a Flexible and Interpretable Machine Learning Approach. Political Analysis 2014; 22(2):143-168.
25. Jeremy Ferwerda J H, Chad J. Hazlett, University S. krls: A Stata Package for Kernel-Based Regularized Least Squares. Journal of Statistical Software 2013.
26. Alberda C, Gramlich L, Jones N, et al. The relationship between nutritional intake and clinical outcomes in critically ill patients: results of an international multicenter observational study. Intensive Care Med 2009; 35(10):1728-1737.
27. Arabi Y M, Aldawood A S, Haddad S H, et al. Permissive Underfeeding or Standard Enteral Feeding in Critically Ill Adults. N Engl J Med 2015; 372(25):2398-2408.
28. Braunschweig C A, Sheean P M, Peterson S J, et al. Intensive nutrition in acute lung injury: a clinical trial (INTACT). JPEN J Parenter Enteral Nutr 2015; 39(1):13-20.
29. National Heart L, Blood Institute Acute Respiratory Distress Syndrome Clinical Trials N, Rice T W, et al. Initial trophic vs full enteral feeding in patients with acute lung injury: the EDEN randomized trial. JAMA 2012; 307(8):795-803.
30. Target Investigators ftACTG, Chapman M, Peake S L, et al. Energy-Dense versus Routine Enteral Nutrition in the Critically Ill. N Engl J Med 2018; 379(19):1823-1834.
31. Wei X, Day A G, Ouellette-Kuntz H, et al. The Association Between Nutritional Adequacy and Long-Term Outcomes in Critically Ill Patients Requiring Prolonged Mechanical Ventilation: A Multicenter Cohort Study. Crit Care Med 2015; 43(8):1569-1579.
32. Schneider S M, Girard-Pipau F, Anty R, et al. Effects of total enteral nutrition supplemented with a multi-fibre mix on faecal short-chain fatty acids and microbiota. Clin Nutr 2006; 25(1):82-90.
33. Majid H A, Cole J, Emery P W, et al. Additional oligofructose/inulin does not increase faecal bifidobacteria in critically ill patients receiving enteral nutrition: a randomised controlled trial. Clin Nutr 2014; 33(6):966-972.
34. Dewulf E M, Cani P D, Claus S P, et al. Insight into the prebiotic concept: lessons from an exploratory, double blind intervention study with inulin-type fructans in obese women. Gut 2013; 62(8):1112-1121.
35. Hooda S, Boler B M, Serao M C, et al. 454 pyrosequencing reveals a shift in fecal microbiota of healthy adult men consuming polydextrose or soluble corn fiber. J Nutr 2012; 142(7):1259-1265.
36. Lecerf J M, Depeint F, Clerc E, et al. Xylo-oligosaccharide (XOS) in combination with inulin modulates both the intestinal environment and immune status in healthy subjects, while XOS alone only shows prebiotic properties. Br J Nutr 2012; 108(10):1847-1858.
37. Garner C D, Antonopoulos D A, Wagner B, et al. Perturbation of the small intestine microbial ecology by streptomycin alters pathology in a *Salmonella enterica* serovar *typhimurium* murine model of infection. Infect Immun 2009; 77(7):2691-2702.
38. Jacobson A, Lam L, Rajendram M, et al. A Gut Commensal-Produced Metabolite Mediates Colonization Resistance to *Salmonella* Infection. Cell Host Microbe 2018.
39. Brugiroux S, Beutler M, Pfann C, et al. Genome-guided design of a defined mouse microbiota that confers colonization resistance against *Salmonella enterica* serovar *Typhimurium*. Nat Microbiol 2016; 2:16215.
40. Lawhon S D, Maurer R, Suyemoto M, et al. Intestinal short-chain fatty acids alter *Salmonella typhimurium* invasion gene expression and virulence through BarA/SirA. Mol Microbiol 2002; 46(5):1451-1464.
41. Caballero S, Kim S, Carter R A, et al. Cooperating Commensals Restore Colonization Resistance to Vancomycin-Resistant *Enterococcus faecium*. Cell Host Microbe 2017; 21(5):592-602 e594.
42. Zaborin A, Smith D, Garfield K, et al. Membership and behavior of ultra-low-diversity pathogen communities present in the gut of humans during prolonged critical illness. MBio 2014; 5(5):e01361-01314.
43. Harris B, Morjaria S M, Littmann E R, et al. Gut Microbiota Predict Pulmonary Infiltrates after Allogeneic Hematopoietic Cell Transplantation. Am J Respir Crit Care Med 2016; 194(4):450-463.
44. Taur Y, Xavier J B, Lipuma L, et al. Intestinal domination and the risk of bacteremia in patients undergoing allogeneic hematopoietic stem cell transplantation. Clin Infect Dis 2012; 55(7):905-914.
45. Manzanares W, Lemieux M, Langlois P L, et al. Probiotic and synbiotic therapy in critical illness: a systematic review and meta-analysis. Crit Care 2016; 19:262.
46. O'Keefe S J, Ou J, Delany J P, et al. Effect of fiber supplementation on the microbiota in critically ill patients. World J Gastrointest Pathophysiol 2011; 2(6): 138-145.
47. Besselink M G, van Santvoort H C, Buskens E, et al. Probiotic prophylaxis in predicted severe acute pancreatitis: a randomised, double-blind, placebo-controlled trial. Lancet 2008; 371(9613):651-659.
48. McIvor A C, Meguid M M, Curtas S, et al. Intestinal obstruction from cecal bezoar; a complication of fiber-containing tube feedings. Nutrition 1990; 6(1):115-117.
49. Livanos A E, Snider E J, Whittier S, et al. Rapid gastrointestinal loss of Clostridial Clusters I V and XIVa in the ICU associates with an expansion of gut pathogens. PLoS One 2018; 13(8):e0200322.
50. Caporaso J G, Lauber C L, Walters W A, et al. Global patterns of 16S rRNA diversity at a depth of millions of sequences per sample. Proc Natl Acad Sci USA 2011; 108 Suppl 1:4516-4522.
51. Human Microbiome Project C. Structure, function and diversity of the healthy human microbiome. Nature 2012; 486(7402):207-214.
52. Kuczynski J, Lauber C L, Walters W A, et al. Experimental and analytical tools for studying the human microbiome. Nat Rev Genet 2011; 13(1):47-58.
53. McDonald D, Price M N, Goodrich J, et al. An improved Greengenes taxonomy with explicit ranks for ecological and evolutionary analyses of bacteria and archaea. ISME J 2012; 6(3):610-618.
54. Caporaso J G, Kuczynski J, Stombaugh J, et al. QIIME allows analysis of high-throughput community sequencing data. Nat Methods 2010; 7(5):335-336.

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

What is claimed is:

1. A method of treating or preventing a bacterial infection, or decreasing antibiotic resistance of gastrointestinal microbiome, in a critically ill patient or an immunosuppressed patient, the method comprising administering at least 10 g/day of an inulin to the patient, wherein the critically ill patient is a patient undergoing intensive care therapy.

2. The method of claim 1, wherein the critically ill patient is in an intensive care unit (ICU).

3. The method of claim 1, wherein the immunosuppressed patient is a transplant recipient.

4. The method of claim 1, wherein the bacterial infection is an antibiotic-resistant infection.

5. The method of claim 1, wherein the bacterial infection is a vancomycin-resistant infection.

6. The method of claim 1, wherein about 16 g/day of the inulin is administered to the patient.

7. The method of claim 1, wherein about 32 g/day of the inulin is administered to the patient.

8. The method of claim 1, wherein the inulin is administered to the patient for about 3 days to about 2 weeks.

9. The method of claim 1, wherein the inulin is administered to the patient for about 7 days.

10. The method of claim 1, wherein the inulin is administered orally.

11. A method of treating or preventing pathogen colonization, or increasing an abundance of short-chain fatty acids (SCFA)-producing bacteria, in a critically ill patient or an immunosuppressed patient, comprising administering at least 10 g/day of an inulin to the patient, wherein the critically ill patient is a patient undergoing intensive care therapy.

12. The method of claim 11, wherein the critically ill patient is in an intensive care unit (ICU).

13. The method of claim 11, wherein the pathogen colonization comprises gastrointestinal pathogen colonization.

14. The method of claim 11, wherein the pathogen colonization is multidrug-resistant (MDR) bacterial colonization.

15. The method of claim 11, wherein the pathogen colonization comprises colonization by antibiotic-resistant pathogens.

16. The method of claim 11, wherein the pathogen colonization comprises colonization by vancomycin-resistant Enterobacteriaceae (VRE), beta-lactamase (ESBL) producing Gram-negative bacteria, *Klebsiella pneumonia* carbapenemase (KPC)-producing bacteria, methicillin-resistant *Staphylococcus aureus* (MRSA), or combinations thereof.

17. The method of claim 11, wherein the pathogen colonization comprises colonization by Enterobacteriaceae, *Staphylococcus, Pseudomonas*, or combinations thereof.

18. The method of claim 11, wherein the SCFA-producing bacteria comprise Clostridial Clusters IV/XIVa selected from the group consisting of *Faecalibacterium prausnitzii, Eubacterium rectale, Ruminococcus, Blautia, Coprococcus, Roseburia*, or combinations thereof.

19. The method of claim 11, wherein the inulin is administered orally.

20. The method of claim 1, wherein the intensive care therapy comprises induction of homeostasis; ventilation; hemodialysis; vasopressor support; fluid support; parenteral nutrition; administration of large volumes of blood products; systemic antibiotic and/or antiviral and/or antifungal and/or antiprotozoic therapy; granulocyte infusion; T cell infusion; stem cell infusion; pulmonary artery catheter insertion; and/or arterial blood pressure catheter insertion.

\* \* \* \* \*